US011957114B2

(12) United States Patent
Premsrirut

(10) Patent No.: US 11,957,114 B2
(45) Date of Patent: Apr. 16, 2024

(54) METHODS OF GENETIC MEDIATED ENGINEERING OF RNAi MODELS

(71) Applicant: Mirimus, Inc., Brooklyn, NY (US)

(72) Inventor: Prem Premsrirut, Long Island City, NY (US)

(73) Assignee: Mirimus, Inc., Brooklyn, NY (US)

( * ) Notice: Subject to any disclaimer, the term of this patent is extended or adjusted under 35 U.S.C. 154(b) by 737 days.

(21) Appl. No.: 16/955,521

(22) PCT Filed: Nov. 28, 2018

(86) PCT No.: PCT/US2018/062836
§ 371 (c)(1),
(2) Date: Jun. 18, 2020

(87) PCT Pub. No.: WO2019/108644
PCT Pub. Date: Jun. 6, 2019

(65) Prior Publication Data

US 2021/0259218 A1 Aug. 26, 2021

Related U.S. Application Data

(60) Provisional application No. 62/591,479, filed on Nov. 28, 2017.

(51) Int. Cl.

| | |
|---|---|
| ***C12N 9/22*** | (2006.01) |
| ***A01K 67/0275*** | (2024.01) |
| ***C12N 15/11*** | (2006.01) |
| ***C12N 15/113*** | (2010.01) |

(52) U.S. Cl.
CPC ............ *A01K 67/0275* (2013.01); *C12N 9/22* (2013.01); *C12N 15/111* (2013.01); *C12N 15/113* (2013.01); *A01K 2207/05* (2013.01); *A01K 2217/072* (2013.01); *C12N 2310/141* (2013.01); *C12N 2310/20* (2017.05); *C12N 2310/531* (2013.01); *C12N 2320/50* (2013.01)

(58) Field of Classification Search
CPC .......... A01K 67/0275; A01K 2217/072; C12N 9/22; C12N 15/111; C12N 15/113; C12N 2310/141; C12N 2310/20; C12N 2310/531; C12N 2320/50
See application file for complete search history.

(56) References Cited

U.S. PATENT DOCUMENTS

| | | | |
|---|---|---|---|
| 5,139,941 | A | 8/1992 | Muzyczka et al. |
| 5,173,414 | A | 12/1992 | Lebkowski et al. |
| 5,436,146 | A | 7/1995 | Shenk et al. |
| 5,474,935 | A | 12/1995 | Chatterjee et al. |
| 5,478,745 | A | 12/1995 | Samulski et al. |
| 5,589,377 | A | 12/1996 | Lebkowski et al. |
| 5,593,874 | A | 1/1997 | Brown et al. |
| 5,698,425 | A | 12/1997 | Ligon et al. |
| 5,712,135 | A | 1/1998 | D'Halluin et al. |
| 5,789,214 | A | 8/1998 | Ryals et al. |
| 5,804,693 | A | 9/1998 | Gaffney et al. |
| 8,697,359 | B1 | 4/2014 | Zhang |
| 2015/0018539 | A1 | 1/2015 | Fellmann |

FOREIGN PATENT DOCUMENTS

| | | | | |
|---|---|---|---|---|
| WO | 1997032016 A1 | | 9/1997 | |
| WO | WO-2010124200 A2 | * | 10/2010 | ......... A01K 67/0276 |
| WO | 2017048995 A1 | | 3/2017 | |

OTHER PUBLICATIONS

Sun et al., "BET protein inhibition mitigates acute myocardial infarction damage in rats via the TLR4/TRAF6/NF-kappaB pathway" Experimental and Therapeutic Medicine, 10: 2319-2324 (2015).
Wang et al., "BET bromodomain blockade mitigates intimal hyperplasia in rat carotid arteries" EBioMedicine, 2: 1650-1661 (2015).
Pelossof et al., "Prediction of potent shRNAs with a sequential classification algorithm" Nature Biotechnology, 35: 350-353 (2017).
Fellmann et al., "Functional identification of optimized RNAi triggers using a massively parallel sensor assay" Molecular Cell, 41: 733-746 (2011).
Fellmann et al., "An optimized microRNA backbone for effective single-copy RNAi" Cell Reports, 5: 1704-1713 (2013).
Watanabe et al., "Quantitative evaluation of first, second, and third generation hairpin systems reveals the limit of mammalian vector-based RNAi" RNA biology, 13: 25-33 (2016).
Van Der Meer et al., "RNAi screen identifies a synthetic lethal interaction between PIM1 overexpression and PLK1 inhibition" Clinical Cancer Research, 20: 3211-3221 (2014).
Singleton et al., "Kinome RNAi screens reveal synergistic targeting of MTOR and FGFR1 pathways for treatment of lung cancer and HNSCC" Cancer Research, 75: 4398-4406 (2015).
Luo et al., "Repurposing endogenous type I CRISPR-Cas systems for programmable gene repression" Nucleic Acids Research, 43: 674-681 (2015).
Qi et al., "Repurposing CRISPR as an RNA-guided platform for sequence-specific control of gene expression" Cell, 152: 1173-1183 (2013).
Cheng et al., "Multiplexed activation of endogenous genes by CRISPR-on, an RNA-guided transcriptional activator system" Cell Research, 23: 1163-1171 (2013).
Gilbert et al., "CRISPR-mediated modular RNA-guided regulation of transcription in eukaryotes" Cell, 154: 442-451 (2013).
Andrieu et al., "Clinical trials for BET inhibitors run ahead of the science" Drug Discovery Today: Technologies, 19: 45-50 (2016).
Boi et al., "The BET bromodomain inhibitor OTX015 affects pathogenetic pathways in preclinical B-cell tumor models and synergizes with targeted drugs" Clinical Cancer Research, 21: 1628-1638 (2015).

(Continued)

*Primary Examiner* — J. E. Angell
(74) *Attorney, Agent, or Firm* — J. Peter Paredes; Amin Talati Wasserman LLP

(57) ABSTRACT

Provided herein are systems and methods for Inducible and conditional CRISPR/Cas9 and RNAi. From animal model creation and the efficiency of CRISPR-based targeting, the present invention comprises developing RNAi models that enable inducible and reversible gene silencing to simulate new therapeutic regimes.

7 Claims, 17 Drawing Sheets

Specification includes a Sequence Listing.

(56) References Cited

OTHER PUBLICATIONS

Henssen et al., "Targeting MYCN-driven transcription by BET-bromodomain inhibition" Clinical Cancer Research, 22: 2470-2481 (2016).
Li et al., "Heritable gene targeting in the mouse and rat using a CRISPR-Cas system" Nature Biotechnology, 31: 681-683 (2013).
Wang et al., "One-step generation of mice carrying mutations in multiple genes by CRISPR/Cas-mediated genome engineering" Cell, 153: 910-918 (2013).
Yang et al., "One-step generation of mice carrying reporter and conditional alleles by CRISPR/Cas-mediated genome engineering" Cell, 154: 1370-1379 (2013).
Schaefer et al., "Unexpected mutations after CRISPR-Cas9 editing in vivo" Nature Methods, 14: 547-548 (2017).
Hsu et al., "DNA targeting specificity of RNA-guided Cas9 nucleases" Nature Biotechnology, 31: 827-832 (2013).
Pattanayak et al., "High-throughput profiling of off-target DNA cleavage reveals RNA-programmed Cas9 nuclease specificity" Nature Biotechnology, 31: 839-843 (2013).
Remy et al., "Efficient gene targeting by homology-directed repair in rat zygotes using TALE nucleases" Genome Research, 24: 1371-1383 (2014).
Sheng et al., "Generation and characterization of a Tet-On (rtTA-M2) transgenic rat" BMC Developmental Biology, doi: 10.1186/1471-213X-10-17 (2010).
Van Der Lelij et al., "Synthetic lethality between the cohesion subunits STAG1 and STAG2 in diverse cancer contexts" Elife, doi: 10.7554/eLife.26980 (2017).
Burr et al., "CMTM6 maintains the expression of PD-L1 and regulates anti-tumor immunity" Nature, 549: 101-105 (2017).
Steinhart et al., "Genome-wide CRISPR screens reveal a Wnt-FZD5 signaling circuit as a druggable vulnerability of RNF43-mutant pancreatic tumors" Nature Medicine, 23: 60-68 (2017).
Maude et al., "Managing cytokine release syndrome associated with novel T cell-engaging therapies" The Cancer Journal, 20: 119-122 (2014).
Tschaharganeh et al., "Using CRISPR/Cas to study gene function and model disease in vivo" The FEBS Journal, 283: 3194-3203 (2016).
Herold et al., "Inducible and reversible gene silencing by stable integration of an shRNA-encoding lentivirus in transgenic rats" PNAS, 105: 18507-18512 (2008).
"International Search Report" issued in corresponding application PCT/US2018/062836, 2 pages, dated Nov. 28, 2018.
"Written opinion of the international searching authority" issued in corresponding application PCT/US2018/062836, 4 pages, dated Nov. 28, 2018.
"International Preliminary Report on Patentability" issued in corresponding foreign application PCT/US2018/062836, 5 pages, dated Nov. 28, 2018.
Goeddel, "Systems for heterologous gene expression" Methods in Enzymology, 185: 3-7 (1990).
Boshart et al., "A Very Strong Enhancer is Located Upstream of an Immediate Early Gene of Human Cytomegalovirus" Cell, 41: 521-530 (1985).
Takebe et al., "SRα Promoter: an Efficient and Versatile Mammalian cDNA Expression System Composed of the Simian Virus 40 Early Promoter and the R-U5 Segment of Human T-Cell Leukemia Virus Type 1 Long Terminal Repeat" Molecular and Cellular Biology, 8: 446-472 (1988).
Dierks et al., "DNA sequences preceding the rabbit β-globin gene are required for formation in mouse L cells of β-globin RNA with the correct 5' terminus" PNAS, 78: 1411-1415 (1981).
Dow et al., "Inducible in vivo genome editing with CRISPR-Cas9" Nature Biotechnology, 33: 390-397 (2015).
Siegel et al., "Using an in vivo phagemid system to identify non-compatible loxP sequences" FEBS Letters, 499: 147-153 (2001).
Matsuda et al., "Controlled expression of transgenes introduced by in vivo electroporation" PNAS, 104: 1027-1032 (2007).
Dickins et al., "Tissue-specific and reversible RNA interference in transgenic mice" Nature Genetics, 39: 914-921 (2007).
Premsrirut et al., "A rapid and scalable system for studying gene function in mice using conditional RNA interference" Cell, 145: 145-158 (2011).
Abe et al., "High levels of BRC4 induced by a Tet-On 3G system suppress DNA repair and impair cell proliferation in vertebrate cells" DNA Repair, 22: 153-164 (2014).
Gossen et al., "Tight control of gene expression in mammalian cells by tetracycline-responsive promoters" PNAS, 89: 5547-5551 (1992).
Loew et al., "Improved Tet-responsive promoters with minimized background expression" BMC Biotechnology, doi: 10.1186/1472-6750-10-81 (2010).
McJunkin et al., "Reversible suppression of an essential gene in adult mice using transgenic RNA interference" PNAS, 108: 7113-7118 (2011).
Dickins et al., "Probing tumor phenotypes using stable and regulated synthetic microRNA precursors" Nature Genetics, 37: 1289-1295 (2005).
Furth et al., "Temporal control of gene expression in transgenic mice by a tetracycline-responsive promoter" PNAS, 91: 9302-9306 (1994).
Boniface et al., "F1Ex-Based Transgenic Reporter Lines for Visualization of Cre and Flp Activity in Live Zebrafish" Genesis, 47: 484-491 (2009).
Branda et al., "Talking about a Revolution: The Impact of Site-Specific Recombinases on Genetic Analyses in Mice" Developmental Cell, 6: 7-28 (2004).
Nern et al., "Multiple new site-specific recombinases for use in manipulating animal genomes" PNAS, 108: 14198-14203 (2011).
Kim et al., "High Cleavage Efficiency of a 2A Peptide Derived from Porcine Teschovirus-1 in Human Cell Lines, Zebrafish and Mice" PLoS One, doi: 10.1371/journal.pone.0018556 (2011).
Jinek et al., "A Programmable Dual-RNA-Guided DNA Endonuclease in Adaptive Bacterial Immunity" Science, 337: 816-821 (2012).
Paddison et al., "Stable suppression of gene expression by RNAi in mammalian cells" PNAS, 99: 1443-1448 (2002).
Kawasaki et al., "Short hairpin type of dsRNAs that are controlled by tRNAVal promoter significantly induce RNAi-mediated gene silencing in the cytoplasm of human cells" Nucleic Acids Research, 31: 700-707 (2003).
Lee et al., "Expression of small interfering RNAs targeted against HIV-1 rev transcripts in human cells" Nature Biotechnology, 19: 500-505 (2002).
Miyagishi et al., "U6 promoter-driven siRNAs with four uridine 3' overhangs efficiently suppress targeted gene expression in mammalian cells" Nature Biotechnology, 19: 497-500 (2002).
Paul et al., "Effective expression of small interfering RNA in human cells" Nature Biotechnology, 19: 505-508 (2002).
Lois et al., "Germline Transmission and Tissue-Specific Expression of Transgenes Delivered by Lentiviral Vectors" Science, 295: 868-872 (2002).
Miller, Progress towards human gene therapy, Blood, 1: 5-14 (1990).
Muzyczka et al., "Use of Adeno-Associated Virus as a General Transduction Vector for Mammalian Cells" Current Topics in Microbiology and Immunology, 158: 97-129 (1992).
Gopalakrishnan et al., "Targeted disruption of Adamts16 gene in a rat genetic model of hypertension" PNAS, 109: 20555-20559 (2012).
Dimasi et al., "Innovation in the pharmaceutical industry: new estimates of R&D costs" Journal of Health Economics, 47: 20-33 (2016).
Harrison et al., "Phase II and phase III failures: 2013-2015" Nature Reviews Drug Discovery, 15: 817-818 (2016).
Abbott, "Return of the rat" Nature, 460: 788 (2009).
Aitman et al., "Progress and prospects in rat genetics: a community view" Nature Genetics, 40: 516-522 (2008).
Gill et al., "The rat as an experimental animal" Science, 245: 269-276 (1989).
Huang et al., "Genetic manipulations in the rat: progress and prospects" Current Opinions in Nephrology and Hypertension, 20: 391-399 (2011).

(56) References Cited

OTHER PUBLICATIONS

Jacob et al., "Gene targeting in the rat: advances and opportunities" Trends in Genetics, 26: 510-518 (2010).
Beard et al., "Efficient method to generate single-copy transgenic mice by site-specific integration in embryonic stem cells" Genesis, 44: 23-28 (2006).
Dow et al., "A pipeline for the generation of shRNA transgenic mice" Nature Protocols, 7:374-393 (2012).
Ebbesen et al., "Pten loss promotes MAPK pathway dependency in HER2/neu breast carcinomas" PNAS, 113: 3030-3035 (2016).
Brondfield et al., "Direct and indirect targeting of MYC to treat acute myeloid leukemia" Cancer Chemotherapy and Pharmacology, 76: 35-46 (2015).
Huang et al., "CDK9-mediated transcription elongation is required for MYC addiction in hepatocellular carcinomas" Genes & Development, 28: 1800-1814 (2014).
Bolden et al., "Inducible in vivo silencing of Brd4 identifies potential toxicities of sustained BET protein inhibition" Cell Reports, 8: 1919-1929 (2014).
Zaiss et al., "Reversible suppression of cyclooxygenase 2 (COX-2) expression in vivo by inducible RNA interference" PLoS One, doi: 10.1371/journal.pone.0101263 (2014).
Lin et al., "Targeting synthetic lethal interactions between myc and the elF4F complex impedes tumorigenesis" Cell Reports, 1: 325-333 (2012).
Lee et al., "Tumor cell survival dependence on the DHX9 DExH-box helicase" Oncogene, 35: 5093-5105 (2016).
Mullenders et al., "Cohesin loss alters adult hematopoietic stem cell homeostasis, leading to myeloproliferative neoplasms" Journal of Experimental Medicine, 212: 1833-1850 (2015).
Sakamaki et al., "Bromodomain Protein BDR4 Is a Transcriptional Repressor of Autophagy and Lysosomal Function" Molecular Cell, 66: 517-532 (2017).
Strikoudis et al., "Opposing functions of H2BK120 ubiquitylation and H3K79 methylation in the regulation of pluripotency by Paf1 complex" Cell Cycle, 16: 2315-2322 (2017).
Nakagawa et al., "Selective and reversible suppression of intestinal stem cell differentiation by pharmacological inhibition of BET bromodomains" Scientific Reports, doi: 10.1038/srep20390 (2016).
European Search Report and Written Opinion issued in corresponding application 18884152.2, 9 pages, dated Jul. 13, 2021.
Premsrirut, PK et al. "Creating Transgenic shRNA Mice by Recombinase-Mediated Cassette Exchange," Cold Spring Harbor Protocol. vol. 2013, No. 9, Sep. 1, 2013, pp. 835-842.
Ohtsuka, M. et al. "Pronuclear injection-based mouse targeted transgenesis for reproducible and highly efficient transgene expression," Nucleic Acids Research, vol. 38, No. 22, Dec. 1, 2010, e198, 11 pages.
Matreyek, K. et al. "A platform for functional assessment of large variant libraries in mammalian cells," Nucleic Acids Research, vol. 45 No. 11, Jun. 20, 2017, e102, 12 pages.
Ohtsuka, M. et al. "One-step generation of multiple transgenic mouse lines using an improved Pronuclear Injection-based Targeted Transgenesis (i-PITT)," BMC Genomics . Apr. 9, 2015;16(1):274; 14 pages.
Ohtsuka, M. et al. "PITT: Pronuclear Injection-Based Targeted Transgenesis, a Reliable Transgene Expression Method in Mice," Experimental Animals, Jan. 1, 2012;61(5):489-502.

* cited by examiner

SEQUENCE LISTING

```
<160> NUMBER OF SEQ ID NOS: 12

<210> SEQ ID NO 1
<211> LENGTH: 3852
<212> TYPE: DNA
<213> ORGANISM: Rattus norvegicus

<400> SEQUENCE: 1

gcttcgtgta aactccctcc atcccaatct ggttccctcc cacccagccc actttccccc      60

aaccctggaa acagaccaac aacccaaact caatttcccc aaaagccaaa aattgggaga     120

caatttcaca tggactttgg aaaacatttt tttcctttgc attcatctct caaacttagt     180

ttttatcttt gaccaactga acgtgaccaa aaaccaaaag tgcattcaac cttaccaaaa     240

agaaaaaaaa ataagaataa ataaataact ttttaaaaaa ggaagcttgg tcctcttgct     300

tgaagaccta tgtgggtata agtccctttc tgcccactgg gcttatgata ccccaaatgc     360

tgccttttct gttcctttct ccaccccctc ttggggcctc tcctccattg ctccccaaat     420

ttaagtctcc cccaaagaca caggaaataa tgcattgtct gcccagccag caaaggcaat     480

gctgaatcgt cccaccagcc cctcaacccc cagcctactt ccctacccag caccttcaaa     540

tcctgccggg acatggggtt ctcggactat tgaaggagcc taaccatctg gcatctccat     600

ggcctctgca acaaatcccc acacacactt tgtttttgag ggcctgtgct gggggagcca     660

cctgcccctc gcaggggttt ggagccaggc agggtcacag cagactggaa acatcggcca     720

cacatgtgca ggctgggtgg gagagactgt tctgttcctt gtgtaattgt gttgctgaaa     780

gactacctcg ttcttgtctt tgtgtgtcac cggggcaact gtgtgggggc ggggatgggg     840

gcagggtggc agcgcgccca gtttggtatc aaaggtgcta catctctgtg aaggggtggg     900

gtgggaagga atttctggtg ctatagaatc tgagatgctc ccctagacca gcaaatgttc     960

cttttgttca aagtattttt ttattctttt ttttttaatg gatagggact tgtgtgaatt    1020

ttcttttcct gacggtgcta tttaacaagg gaggagagag tgccaactcc agcctgctct    1080

ctctctaccc ccctcttcac tcttccagct cctgggccta tctgatgatc tctctctctt    1140

ctgaaaccct cccctcttgc tgctgctccc taccctcagc ttctctctct ctctgtcctg    1200

catcagggtt tcagagcacc attttccaaa gcacaaagca gtttttatcc ctggggtggg    1260
```

-continued

```
aggaagcaag agactctgta cctattttgt atgtgtataa taatttgaga tgtttttaat   1320
tattttgatt gctggaataa agcatgtgga aatgacccaa cgcatgttca gtggtctctg   1380
aatttccttc ctggaacttg gggaggtggg gatccaggga gaggctttgg gatgtgtgag   1440
gcagggagct tgtcttctac catcaccctt tatctctccc cccacttctc atccagatgc   1500
cgttgccttc ctcttgcctt tcttacgcct tagacccatt tttcttgcct cttttacctt   1560
ttccccttc aagtcctctt tgcacatccc caagtccccc aagtctccac cacagttcaa   1620
taccagacgc acagcatcac gggcaaactc gcacgcactt caaatcccgg accacccata   1680
cctcaggcca gaatcctaat ggtgtatcac tcttccatga tgtagacctg aggcctggcg   1740
aggtgttgcc tatgggtcct gagaggctca gggactctca aaaggatcca gagggaggga   1800
acagggactg agtcatggag gaccaggttt ctccctggtc aagcatggag gggtagttgg   1860
cttctcccca tctcttgccc aaagaaacaa gtgatttgat atagaagggg cctttttgagg   1920
ctggagtgcc accaggaggg taagaatgtt ctgaggtcac tcttgctctc accagaggga   1980
ggtgcccagc tcccaaaggg atctcctggg ggctcttaga gagctgtggt gaaggaactt   2040
ccagtgtgtc accagaaagg acaggacccc acaccacaga ggtgcgtggg tcactcctgg   2100
tcttcggcgt gcccagagag cgtgctggct cggtgcaggg ggcctgtgga atcatgccac   2160
ccttcctcct gcctcttctt ccctttgcct ttatctctac aactttttgc ttctttttcc   2220
tcctttttccc ccctccctcc ttccctccct tcctctgccg gtctgagaat ctgaggccct   2280
aggagagtgg taactgactg tcccccacat ctcagagaat ggggacatag tggaaggtct   2340
gagaatccag caggcaggag tctgcactga accggacact aaacataagg acacaggtga   2400
ccccattcag gggtcaggt ctcaaatttg aaaggaaggc acagactact tgtagcttcc   2460
ctttcttgtg ctaccagaga gaccaactaa tctactgcag tgtccactgg acacgatctt   2520
actgccactg agtactcgag actgttaatt atgaccttta ataatttatt actagcactt   2580
tacatgaggg caatgtaaaa agaaaattta tctagagagg aaaagaagtt gaggagtata   2640
aatgaagatc tatttagaca caaattaccc aaaattgcgt ggtcctgata gacccattga   2700
ttgatgcagt gattgggtga tacctttctc cccaggcatc cccagtcttg aggctcttcc   2760
tggcttagac cctatctctt cccatcctca cagggtccat ccttctgaac tcagcatctg   2820
agctgtacct ggccactact cacttgtcta agcttattgt ctcctccagg gcctacatct   2880
gtcatctcag tcaataggca tgattacaat ttatatatat aatatatata cacatatatt   2940
atatataata taaattcaca tacacacaca cacacacaca cacacacaca cacacacaca   3000
cacacacaca caagcccaag ctgacctcag ccctctgagg tcccaacaca ctgctagccc   3060
cttacccaga cgttacaggc ccctgtggtc atggtccacc atgttctttc tagtgtcaag   3120
gcctggaaat tctgtgcagg gctgggcaca gtcttcatag gtactaggga gagacaagat   3180
ggtgatagag gtcctctgga ggatgtgagt acagagtaca gagctgtgga aaggtgaagg   3240
tgaaggtgag aggaaggaga acaaacgaca gtttcctgac gtgacaggta gttgagccct   3300
taaaatgtgg ctccgtgata aaggactgca atcctcactt ttactactgc aatcactttc   3360
actaactgca aaagggctga aggaagcaag ctccaggcaa aggagcgaag agcgcctctc   3420
actgtgcata tgcaaatcta cacgggcgtc tgcatgcaca cgcatgttca catgtggata   3480
tatgcatgag catgtgcgtc ttgtggtagg ccttgtgtgc agcactcctc ggcggccatc   3540
acatggtgag ggctggtatg tgctctaagt gtgtgtacag agcagcaggg aagggggaca   3600
acaaagagag cattgtatca cactctgaac ccaagccctc ctttccgctg acatcattgc   3660
```

cgccttaaat acagatgcca ggccctgttc ccaagaccct cactgtcccc tgtgtgctaa 3720
cacagctctg ctgtgtggac ttcccgttca tctttatggg gaagactatc ctcctggagc 3780
cgatgtttcc atcaaatcca agtagaaaaa atctacaggg aaagaaggtt tggttttgat 3840
tttttactct tg 3852

<210> SEQ ID NO 2
<211> LENGTH: 20
<212> TYPE: DNA
<213> ORGANISM: Rattus norvegicus

<400> SEQUENCE: 2
caataccaga cgcacagcat 20

<210> SEQ ID NO 3
<211> LENGTH: 20
<212> TYPE: DNA
<213> ORGANISM: Rattus norvegicus

<400> SEQUENCE: 3
gtggggtcct gtcctttctg 20

<210> SEQ ID NO 4
<211> LENGTH: 23
<212> TYPE: DNA
<213> ORGANISM: Rattus norvegicus

<400> SEQUENCE: 4
aggctggagt gccaccagga ggg 23

<210> SEQ ID NO 5
<211> LENGTH: 4853
<212> TYPE: DNA
<213> ORGANISM: Rattus norvegicus

<400> SEQUENCE: 5
tattttgatt gctggaataa agcatgtgga aatgacccaa cgcatgttca gtggtctctg 60
aatttccttc ctggaacttg gggaggtggg gatccaggga gaggctttgg gatgtgtgag 120
gcagggagct tgtcttctac catcaccctt tatctctccc cccacttctc atccagatgc 180
cgttgccttc ctcttgcctt tcttacgcct tagacccatt tttcttgcct cttttacctt 240 ttccccttc aagtcctctt tgcacatccc caagtccccc aagtctccac cacagttcaa 300
taccagacgc acagcatcac gggcaaactc gcacgcactt caaatcccgg accacccata 360
cctcaggcca gaatcctaat ggtgtatcac tcttccatga tgtagacctg aggcctggcg 420
aggtgttgcc tatgggtcct gagaggctca gggactctca aaaggatcca gagggaggga 480
acagggactg agtcatggag gaccaggttt ctccctggtc aagcatggag gggtagttgg 540
cttctcccca tctcttgccc aaagaaacaa gtgatttgat atagaagggg cctttgagg 600 ctggagtgcc accgattgca tatctggggg atcgattcta gattcgagtt taccactccc 660
tatcagtgat agagaaaagt gaaagtcgag tttaccactc cctatcagtg atagagaaaa 720
gtgaaagtcg agtttaccac tccctatcag tgatagagaa aagtgaaagt cgagtttacc 780
actccctatc agtgatagag aaaagtgaaa gtcgagttta ccactcccta tcagtgatag 840
agaaaagtga aagtcgagtt taccactccc tatcagtgat agagaaaagt gaaagtcgag 900
tttaccactc cctatcagtg atagagaaaa gtgaaagtcg agctcggtac ccgggtcgag 960

-continued

```
gtaggcgtgt acggtgggag gcctatataa gcagagctcg tttagtgaac cgtcagatcg   1020
cctggagacg ccatccacgc tgttttgacc tccatagaag acaccgggac cgatccgtcg   1080
agcttgcgtt ggatccatgg tgagcaaggg cgaggagctg ttcaccgggg tggtgcccat   1140
cctggtcgag ctggacggcg acgtaaacgg ccacaagttc agcgtgtccg gcgagggcga   1200
gggcgatgcc acctacggca agctgaccct gaagttcatc tgcaccaccg gcaagctgcc   1260
cgtgccctgg cccaccctcg tgaccaccct gacctacggc gtgcagtgct tcagccgcta   1320
ccccgaccac atgaagcagc acgacttctt caagtccgcc atgcccgaag gctacgtcca   1380
ggagcgcacc atcttcttca aggacgacgg caactacaag acccgcgccg aggtgaagtt   1440
cgagggcgac accctggtga accgcatcga gctgaagggc atcgacttca aggaggacgg   1500
caacatcctg gggcacaagc tggagtacaa ctacaacagc cacaacgtct atatcatggc   1560
cgacaagcag aagaacggca tcaaggtgaa cttcaagatc cgccacaaca tcgaggacgg   1620
cagcgtgcag ctcgccgacc actaccagca gaacaccccc atcggcgacg gccccgtgct   1680
gctgcccgac aaccactacc tgagcaccca gtccgccctg agcaaagacc ccaacgagaa   1740
gcgcgatcac atggtcctgc tggagttcgt gaccgccgcc gggatcactc tcggcatgga   1800
cgagctgtac aagtaatgaa taacagggta attgtttgaa tgaggcttca gtactttaca   1860
gaatcgttgc ctgcacatct tggaaacact tgctgggatt acttcgactt cttaacccaa   1920
cagaaggctc gagaaggtat attgctgttg acagtgagcg cctcggactt caaggggcta   1980
gaattcgagc aattatcttg tttactaaaa ctgaatacct tgctatctct ttgatacatt   2040
tttacaaagc tgaattaaaa tggtataaat taaatcactt ttttcaattg acgcgttgag   2100
aacttcaggg tgagtttggg gacccttgat tgttctttct ttttcgctat tgtaaaattc   2160
atgttatatg gagggggcaa agttttcagg gtgttgttta gaatgggaag atgtcccttg   2220
tatcaccatg gaccctcatg ataattttgt ttctttcact ttctactctg ttgacaacca   2280
ttgtctcctc ttattttctt ttcattttct gtaacttttt cgttaaactt tagcttgcat   2340
ttgtaacgaa tttttaaatt cacttttgtt tatttgtcag attgtaagta ctttctctaa   2400
tcactttttt ttcaaggcaa tcagggtata ttatattgta cttcagcaca gttttagaga   2460
acaattgtta taattaaatg ataaggtaga atatttctgc atataaattc tggctggcgt   2520
ggaaatattc ttattggtag aaacaactac accctggtca tcatcctgcc tttctcttta   2580
tggttacaat gatatacact gtttgagatg aggataaaat actctgagtc caaaccgggc   2640
ccctctgcta accatgttca tgccttcttc tctttcctac agctcctggg caacgtgctg   2700
gttgttgtgc tgtctcatca ttttggcaaa ggattcactc ctcaggtgca ggctgcctat   2760
cagaaggtgg tggctggtgt ggccaatgcc ctggctcaca aataccactg agatcgtttt   2820
ccctctgcca aaaattatgg ggacatcatg aagccccttg agcatctgac ttctggctaa   2880
taaaggaaat ttattttcat tgcaatagtg tgttggaatt tctcgatcgc tagtacgacc   2940
gtaagaatgt tctgaggtca ctcttgctct caccagaggg aggtgcccag ctcccaaagg   3000
gatctcctgg gggctcttag agagctgtgg tgaaggaact tccagtgtgt caccagaaag   3060
gacaggaccc cacaccacag aggtgcgtgg gtcactcctg gtcttcggcg tgcccagaga   3120
gcgtgctggc tcggtgcagg gggcctgtgg aatcatgcca cccttcctcc tgcctcttct   3180
tccctttgcc tttatctcta caactttttg cttctttttc ctccttttcc cccctccctc   3240
cttccctccc ttcctctgcc ggtctgagaa tctgaggccc taggagagtg gtaactgact   3300
gtcccccaca tctcagagaa tggggacata gtggaaggtc tgagaatcca gcaggcagga   3360
```

-continued

```
gtctgcactg aaccggacac taaacataag gacacaggtg accccattca gggggtcagg   3420

tctcaaattt gaaaggaagg cacagactac ttgtagcttc cctttcttgt gctaccagag   3480

agaccaacta atctactgca gtgtccactg gacacgatct tactgccact gagtactcga   3540

gactgttaat tatgaccttt aataatttat tactagcact ttacatgagg gcaatgtaaa   3600

aagaaaattt atctagagag gaaaagaagt tgaggagtat aaatgaagat ctatttagac   3660

acaaattacc caaaattgcg tggtcctgat agacccattg attgatgcag tgattgggtg   3720

ataccttttct ccccaggcat ccccagtctt gaggctcttc ctggcttaga ccctatctct   3780

tcccatcctc acagggtcca tccttctgaa ctcagcatct gagctgtacc tggccactac   3840

tcacttgtct aagcttattg tctcctccag ggcctacatc tgtcatctca gtcaataggc   3900

atgattacaa tttatatata taatatatat acacatatat tatatataat ataaattcac   3960

atacacacac acacacacac acacacacac acacacacac acacacacac acaagcccaa   4020

gctgacctca gccctctgag gtcccaacac actgctagcc ccttacccag acgttacagg   4080

cccctgtggt catggtccac catgttcttt ctagtgtcaa ggcctggaaa ttctgtgcag   4140

ggctgggcac agtcttcata ggtactaggg agagacaaga tggtgataga ggtcctctgg   4200

aggatgtgag tacagagtac agagctgtgg aaaggtgaag gtgaaggtga gaggaaggag   4260

aacaaacgac agtttcctga cgtgacaggt agttgagccc ttaaaatgtg gctccgtgat   4320

aaaggactgc aatcctcact tttactactg caatcacttt cactaactgc aaaagggctg   4380

aaggaagcaa gctccaggca aaggagcgaa gagcgcctct cactgtgcat atgcaaatct   4440

acacgggcgt ctgcatgcac acgcatgttc acatgtggat atatgcatga gcatgtgcgt   4500

cttgtggtag gccttgtgtg cagcactcct cggcggccat cacatggtga gggctggtat   4560

gtgctctaag tgtgtgtaca gagcagcagg gaagggggac aacaaagaga gcattgtatc   4620

acactctgaa cccaagccct cctttccgct gacatcattg ccgccttaaa tacagatgcc   4680

aggccctgtt cccaagaccc tcactgtccc ctgtgtgcta acacagctct gctgtgtgga   4740

cttcccgttc atctttatgg ggaagactat cctcctggag ccgatgtttc catcaaatcc   4800

aagtagaaaa aatctacagg gaaagaaggt ttggttttga ttttttactc ttg          4853


<210> SEQ ID NO 6
<211> LENGTH: 20
<212> TYPE: DNA
<213> ORGANISM: Rattus norvegicus

<400> SEQUENCE: 6

caataccaga cgcacagcat                                                 20


<210> SEQ ID NO 7
<211> LENGTH: 16
<212> TYPE: DNA
<213> ORGANISM: Rattus norvegicus

<400> SEQUENCE: 7

cgtcgccgtc cagctc                                                     16


<210> SEQ ID NO 8
<211> LENGTH: 20
<212> TYPE: DNA
<213> ORGANISM: Rattus norvegicus

<400> SEQUENCE: 8
```

gggcaaagt tttcagggtg 20

<210> SEQ ID NO 9
<211> LENGTH: 20
<212> TYPE: DNA
<213> ORGANISM: Rattus norvegicus

<400> SEQUENCE: 9
gtggggtcct gtcctttctg 20

<210> SEQ ID NO 10
<211> LENGTH: 23
<212> TYPE: DNA
<213> ORGANISM: Rattus norvegicus

<400> SEQUENCE: 10
gctgttgaca gtgagcgcct cgg 23

<210> SEQ ID NO 11
<211> LENGTH: 870
<212> TYPE: DNA
<213> ORGANISM: Rattus norvegicus

<400> SEQUENCE: 11
caataccaga cgcacagcat yycacgggca aactcgcacg cacttcaaat cccggaccac 60
ccatacctca ggccagaatc ctaatggtgt atcactcttc catgatgtag acctgaggcc 120
tggcgaggtg ttgcctatgg gtcctgagag gctcagggac tctcaaaagg atccagaggg 180
agggaacagg gactgagtca tggaggacca ggtttctccc tggtcaagca tggaggggta 240
gttggcttct ccccatctct tgcccaaaga aacaagtgat ttgatataga aggggccttt 300
tgaggctgga gtgccaccga ttgcatatct gggggatcga ttctagattc gagtttacca 360
ctccctatca gtgatagaga aaagtgaaag tcgagtttac cactccctat cagtgataga 420
gaaaagtgaa agtcgagttt accactccct atcagtgata gagaaaagtg aaagtcgagt 480
ttaccactcc ctatcagtga tagagaaaag tgaaagtcga gtttaccact ccctatcagt 540
gatagagaaa agtgaaagtc gagtttacca ctccctatca gtgatagaga aaagtgaaag 600
tcgagtttac cactccctat cagtgataga gaaaagtgaa agtcgagctc ggtacccggg 660
tcgaggtagg cgtgtacggt gggaggccta tataagcaga gctcgtttag tgaaccgtca 720
gatcgcctgg agacgccatc cacgctgttt tgacctccat agaagacacc gggaccgatc 780
cgtcgagctt gcgttggatc catggtgagc aagggcgagg agctgttcac cggggtggtg 840
cccatcctgg tcgagctgga cggcgacgyy 870

<210> SEQ ID NO 12
<211> LENGTH: 904
<212> TYPE: DNA
<213> ORGANISM: Rattus norvegicus

<400> SEQUENCE: 12
ggggcaaagt tttcagggtg yyttgtttag aatgggaaga tgtcccttgt atcaccatgg 60
accctcatga taattttgtt tctttcactt tctactctgt tgacaaccat tgtctcctct 120
tattttcttt tcattttctg taactttttc gttaaacttt agcttgcatt tgtaacgaat 180
ttttaaattc acttttgttt atttgtcaga ttgtaagtac tttctctaat cacttttttt 240
tcaaggcaat cagggtatat tatattgtac ttcagcacag ttttagagaa caattgttat 300
aattaaatga taaggtagaa tatttctgca tataaattct ggctggcgtg gaaatattct 360

-continued

```
tattggtaga aacaactaca ccctggtcat catcctgcct ttctctttat ggttacaatg    420
atatacactg tttgagatga ggataaaata ctctgagtcc aaaccgggcc cctctgctaa    480
ccatgttcat gccttcttct ctttcctaca gctcctgggc aacgtgctgg ttgttgtgct    540
gtctcatcat tttggcaaag gattcactcc tcaggtgcag gctgcctatc agaaggtggt    600
ggctggtgtg gccaatgccc tggctcacaa ataccactga gatcgttttc cctctgccaa    660
aaattatggg gacatcatga agccccttga gcatctgact tctggctaat aaaggaaatt    720
tattttcatt gcaatagtgt gttggaattt ctcgatcgct agtacgaccg taagaatgtt    780
ctgaggtcac tcttgctctc accagaggga ggtgcccagc tcccaaaggg atctcctggg    840
ggctcttaga gagctgtggt gaaggaactt ccagtgtgtc accagaaagg acaggacccc    900
acyy                                                                  904
```

METHODS OF GENETIC MEDIATED ENGINEERING OF RNAi MODELS

CROSS-REFERENCE TO RELATED APPLICATIONS

The present application claims priority to and is a national phase of PCT/US18/62836 filed Nov. 28, 2018; which claims priority to U.S. Provisional Application Ser. No. 62/591,479 filed Nov. 28, 2017, herein incorporated by references in their entireties.

SEQUENCE LISTING

The present application contains a Sequence Listing which is submitted electronically in ASCII format and is incorporated by reference in its entirety. Said ASCII copy, created on Feb. 5, 2021, is named Sequence Listing and 16 KB in size.

BACKGROUND

This invention relates to methods and systems for gene targeting genome editing and transient gene silencing in the field of molecular biology and genetic engineering. More specifically, the invention describes the use of CRISPR-associated nuclease to specifically and efficiently edit DNA sequences coupled with RNA interference to mimic drug therapy.

"RNA interference", "post-transcriptional gene silencing", "quelling"—these different names describe similar effects that result from the overexpression of transgenes encoding double-stranded RNA precursors, or from the deliberate introduction of double-stranded RNA into cells.

Animal models are the gold standard for dissecting disease mechanisms; however, the cost and long lead time to develop them has prevented their routine use in the drug discovery process. The advent of CRISPR/Cas9 genome editing, together with major advances in RNA interference technologies enables one to genetically engineer and study human diseases in mice. Beyond investigating disease development, inducible loss-of-function genetic tools provide a powerful and scalable system to probe candidate therapeutic targets prior to drug development. Despite the utility of mouse models, for many scientists, the rat still remains the preferred rodent due to their larger size for surgical manipulation, repeat blood sampling, and their cognitive and physiological characteristics that more closely resemble humans than their mouse counterparts3. For neurobiology, cardiobiology, immunology and toxicology, they are still the dominant rodent model in research[4-7]. Although technologies in manipulating and culturing mouse embryonic stem cells enabled mice to become the standard for genetically altered models, CRISPR/Cas9 technology now provides a path for manipulating the rat genome. Current approaches enable the derivation of permanent gene knockout alleles, but do not allow temporal gene regulation that we have shown is important for exploring therapeutic efficacy and toxicity of new drug targets. RNAi rat models will transform the preclinical validation process with in vivo assessment of potential drug response and resistance mechanisms in vivo, ultimately guiding the development of safer and more effective drugs.

Pharmaceutical companies often require that most toxicology studies of their compounds are still done in rats prior to Phase I. Rats will gain popularity once again as the premier rodent model in drug discovery. RNAi rats will better mimic the dynamics of small molecule inhibition than permanent genetic knockouts.

The present invention attempts to address issues with gene targeting and genome editing.

SUMMARY OF THE INVENTION

Provided herein are systems and methods for Inducible and conditional CRISPR/Cas9 and RNAi. From mouse model creation and the efficiency of CRISPR-based targeting, the present invention comprises developing RNAi rat models that enable inducible and reversible gene silencing to simulate new therapeutic regimes.

A method of establishing founder knock-in strains is disclosed, and generally comprises: creating a founder strain with a nucleotide sequence comprising a promoter, a reporting sequence, and a miRNA backbone; and using the founder strain to knockin a variable shRNA sequence for a subsequent strain to be produced.

The methods and systems are set forth in part in the description which follows, and in part will be obvious from the description, or can be learned by practice of the methods and systems. The advantages of the methods and systems will be realized and attained by means of the elements and combinations particularly pointed out in the appended claims. It is to be understood that both the foregoing general description and the following detailed description are exemplary and explanatory only and are not restrictive of the methods and systems, as claimed.

BRIEF DESCRIPTION OF THE DRAWINGS

In the accompanying figures, like elements are identified by like reference numerals among the several preferred embodiments of the present invention.

DETAILED DESCRIPTION OF THE INVENTION

Figure 1A:
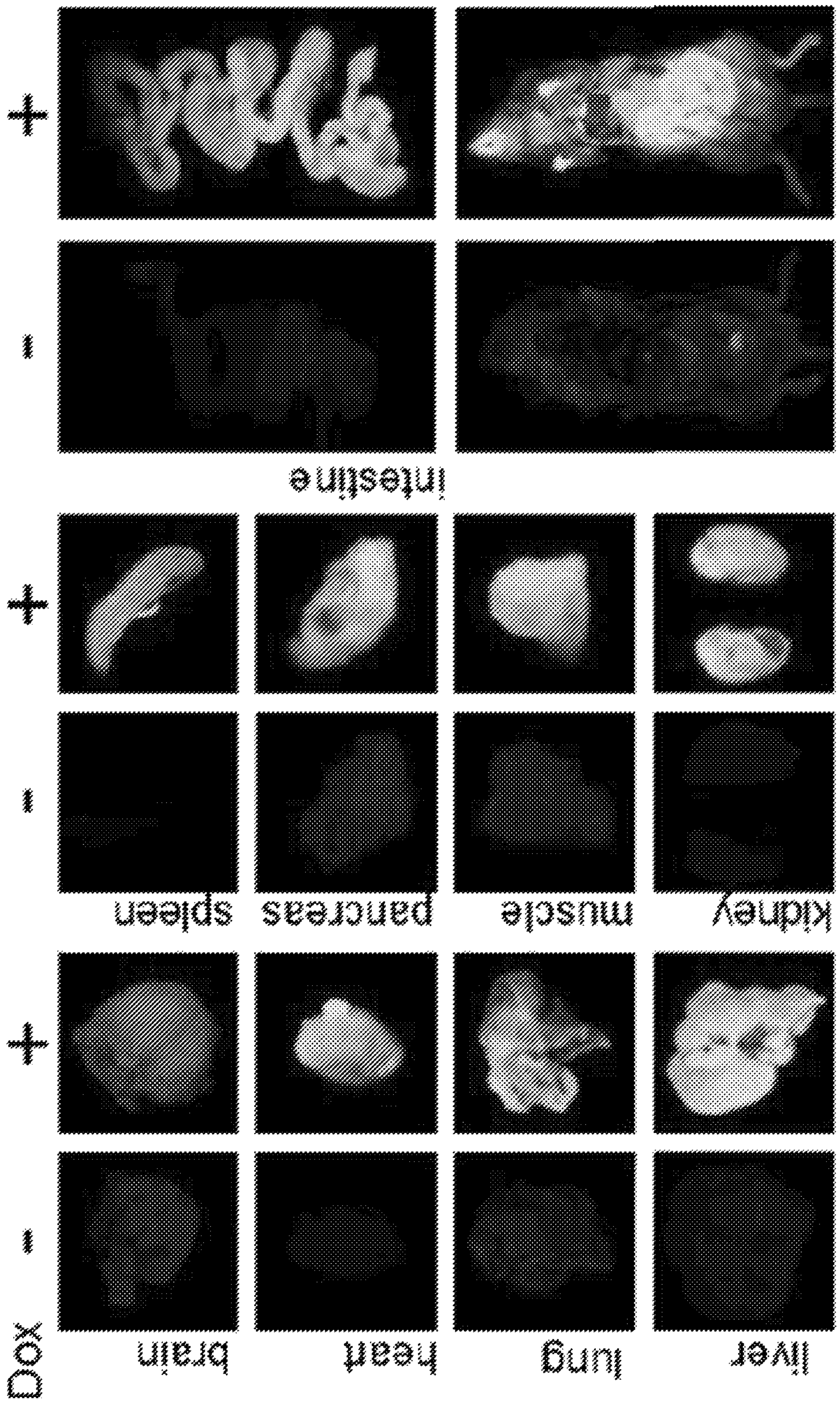
FIG. 1A are micrograph images of GFP expression in tissues harvested from bitransgenic shMkk4/CAG-rtTA3 treated with dox for 3 days.

The foregoing and other features and advantages of the invention are apparent from the following detailed description of exemplary embodiments, read in conjunction with the accompanying drawings. The detailed description and drawings are merely illustrative of the invention rather than limiting, the scope of the invention being defined by the appended claims and equivalents thereof.

Recitation of ranges of values herein are merely intended to serve as a shorthand method of referring individually to each separate value falling within the range, unless otherwise indicated herein, and each separate value is incorporated into the specification as if it were individually recited herein. The word "about," when accompanying a numerical value, is to be construed as indicating a deviation of up to and inclusive of 10% from the stated numerical value. The use of any and all examples, or exemplary language ("e.g." or "such as") provided herein, is intended merely to better illuminate the invention and does not pose a limitation on the scope of the invention unless otherwise claimed. No language in the specification should be construed as indicating any nonclaimed element as essential to the practice of the invention.

The terms "polynucleotide", "nucleotide", "nucleotide sequence", "nucleic acid" and "oligonucleotide" are used interchangeably. They refer to a polymeric form of nucleotides of any length, either deoxyribonucleotides or ribonucleotides, or analogs thereof. Polynucleotides may have any three dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

In aspects of the invention the terms "chimeric RNA", "chimeric guide RNA", "guide RNA", "single guide RNA" and "synthetic guide RNA" are used interchangeably and refer to the polynucleotide sequence comprising the guide sequence, the tracr sequence and the tracr mate sequence. The term "guide sequence" refers to the about 20 bp sequence within the guide RNA that specifies the target site and may be used interchangeably with the terms "guide" or "spacer". The term "tracr mate sequence" may also be used interchangeably with the term "direct repeat(s)". An exemplary CRISPR-Cas system is indicated below.

As used herein the term "wild type" is a term of the art understood by skilled persons and means the typical form of an organism, strain, gene or characteristic as it occurs in nature as distinguished from mutant or variant forms.

As used herein the term "variant" should be taken to mean the exhibition of qualities that have a pattern that deviates from what occurs in nature.

The terms "non-naturally occurring" or "engineered" are used interchangeably and indicate the involvement of the hand of man. The terms, when referring to nucleic acid molecules or polypeptides mean that the nucleic acid molecule or the polypeptide is at least substantially free from at least one other component with which they are naturally associated in nature and as found in nature.

"Complementarity" refers to the ability of a nucleic acid to form hydrogen bond(s) with another nucleic acid sequence by either traditional Watson-Crick or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%. 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

As used herein, "stringent conditions" for hybridization refer to conditions under which a nucleic acid having complementarity to a target sequence predominantly hybridizes with the target sequence, and substantially does not hybridize to non-target sequences. Stringent conditions are generally sequence-dependent, and vary depending on a number of factors. In general, the longer the sequence, the higher the temperature at which the sequence specifically hybridizes to its target sequence. Non-limiting examples of stringent conditions are described in detail in Tijssen (1993), Laboratory Techniques In Biochemistry And Molecular Biology-Hybridization With Nucleic Acid Probes Part 1, Second Chapter "Overview of principles of hybridization and the strategy of nucleic acid probe assay", Elsevier, N.Y.

"Hybridization" refers to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi stranded complex, a single self 17 hybridizing strand, or any combination of these. A hybridization reaction may constitute a step in a more extensive process, such as the initiation of PCR, or the cleavage of a polynucleotide by an enzyme. A sequence capable of hybridizing with a given sequence is referred to as the "complement" of the given sequence.

As used herein, "expression" refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

The terms "polypeptide", "peptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" includes natural and/or unnatural or synthetic amino acids, including glycine and both the D or L optical isomers, and amino acid analogs and peptidomimetics.

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed.

The terms "therapeutic agent", "therapeutic capable agent" or "treatment agent" are used interchangeably and refer to a molecule or compound that confers some beneficial effect upon administration to a subject. The beneficial effect includes enablement of diagnostic determinations; amelioration of a disease, symptom, disorder, or pathological condition; reducing or preventing the onset of a disease, symptom, disorder or condition; and generally counteracting a disease, symptom, disorder or pathological condition.

As used herein, "species" are used interchangeably herein to refer to a vertebrate, preferably a mammal. Mammals include, but are not limited to, murines, simians, humans, farm animals, sport animals, and pets.

As used herein, "treatment" or "treating," or "palliating" or "ameliorating" are used interchangeably. These terms refer to an approach for obtaining beneficial or desired results including but not limited to a therapeutic benefit and/or a prophylactic benefit. By therapeutic benefit is meant any therapeutically relevant improvement in or effect on one or more diseases, conditions, or symptoms under treatment. For prophylactic benefit, the compositions may be administered to a subject at risk of developing a particular disease, condition, or symptom, or to a subject reporting one or more of the physiological symptoms of a disease, even though the disease, condition, or symptom may not have yet been manifested.

The term "effective amount" or "therapeutically effective amount" refers to the amount of an agent that is sufficient to effect beneficial or desired results. The therapeutically effective amount may vary depending upon one or more of: the subject and disease condition being treated, the weight and age of the subject, the severity of the disease condition, the manner of administration and the like, which can readily be determined by one of ordinary skill in the art. The term also applies to a dose that will provide an image for detection by any one of the imaging methods described herein. The specific dose may vary depending on one or more of: the particular agent chosen, the dosing regimen to be followed, whether it is administered in combination with other compounds, timing of administration, the tissue to be imaged, and the physical delivery system in which it is carried.

"Recombination" refers to a process of exchange of genetic information between two polynucleotides. For the purposes of this disclosure, "homologous recombination (HR)" refers to the specialized form of such exchange that takes place, for example, during repair of double-strand breaks in cells. This process requires nucleotide sequence homology, uses a "donor" molecule to template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to resynthesize genetic information that will become part of the target, and/or related processes. Such specialized HR often results in an alteration of the sequence of the target molecule such that part or all of the sequence of the donor polynucleotide is incorporated into the target polynucleotide.

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "cleavage domain" comprises one or more polypeptide sequences which possesses catalytic activity for DNA cleavage. A cleavage domain can be contained in a single polypeptide chain or cleavage activity can result from the association of two (or more) polypeptides.

The term "regulatory element" is intended to include promoters, enhancers, internal ribosomal entry sites (IRES), and other expression control elements (e.g. transcription termination signals, such as polyadenylation signals and poly-U sequences). Such regulatory elements are described, for example, in Goeddel, GENE EXPRESSION TECHNOLOGY: METHODS IN ENZYMOLOGY 185, Academic Press, San Diego, Calif. (1990). IRES may be substituted for P2A. Regulatory elements include those that direct constitutive expression of a nucleotide sequence in many types of host cell and those that direct expression of the nucleotide sequence only in certain host cells (e.g., tissue-specific regulatory sequences). A tissue-specific promoter may direct expression primarily in a desired tissue of interest, such as muscle, neuron, bone, skin, blood, specific organs (e.g. liver, pancreas), or particular cell types (e.g. lymphocytes). Regulatory elements may also direct expression in a temporal-dependent manner, such as in a cell-cycle dependent or developmental stage-dependent manner, which may or may not also be tissue or cell-type specific. In some embodiments, a vector comprises one or more pol III promoter (e.g. 1, 2, 3, 4, 5, or more pol I promoters), one or more pol II promoters (e.g. 1, 2, 3, 4, 5, or more pol II promoters), one or more pol I promoters (e.g. 1, 2, 3, 4, 5, or more pol I promoters), or combinations thereof. Examples of pol III promoters include, but are not limited to, U6 and H1 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the β-actin promoter, the phosphoglycerol kinase (PGK) promoter, and the EF1a promoter. Also encompassed by the term "regulatory element" are enhancer elements, such as WPRE; CMV enhancers; the R-U5' segment in LTR of HTLV-I (Mol. Cell. Biol., Vol. 8(1), p. 466-472, 1988);

SV40 enhancer; and the intron sequence between exons 2 and 3 of rabbit β-globin (Proc. Natl. Acad. Sci. USA., Vol. 78(3), p. 1527-31, 1981). It will be appreciated by those skilled in the art that the design of the expression vector can depend on such factors as the choice of the host cell to be transformed, the level of expression desired, etc. A vector can be introduced into host cells to thereby produce transcripts, proteins, or peptides, including fusion proteins or peptides, encoded by nucleic acids as described herein (e.g., clustered regularly interspersed short palindromic repeats (CRISPR) transcripts, proteins, enzymes, mutant forms thereof, fusion proteins thereof, etc.).

Promoters/enhancers which may be used to control the expression of a shRNA construct in vivo include, but are not limited to, the PolIII human or murine U6 and H1 systems, the cytomegalovirus (CMV) promoter/enhancer, the human β-actin promoter, the glucocorticoid-inducible promoter present in the rat and mouse mammary tumor virus long terminal repeat (MMTV LTR), the long terminal repeat sequences of Moloney murine leukemia virus (MuLV LTR), the SV40 early or late region promoter, the promoter contained in the 3' long terminal repeat of Rous sarcoma virus (RSV), the herpes simplex virus (HSV) thymidine kinase promoter/enhancer, and the herpes simplex virus LAT promoter. Transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., an immunoglobulin promoter, and from heat-shock promoters, provided such promoters are compatible with the host cell systems. Inducible systems, such as Tet promoters may be employed. In addition, recombinase systems, such as Cre/lox may be used to allow excision of shRNA constructs at desired times. The Cre may be responsive (transcriptionally or post-transcriptionally) to an external signal, such as tamoxifen.

"Inhibition of gene expression" refers to the absence or observable decrease in the level of protein and/or mRNA product from a target gene. "Specificity" refers to the ability to inhibit the target gene without manifest effects on other genes of the cell. The consequences of inhibition can be confirmed by examination of the outward properties of the cell or organism (as presented below in the examples) or by biochemical techniques such as RNA solution hybridization, nuclease protection, Northern hybridization, reverse transcription, gene expression monitoring with a microarray, antibody binding, enzyme linked immunosorbent assay (ELISA), Western blotting, radioimmunoassay (MA), other immunoassays, and fluorescence activated cell analysis (FACS). For RNA-mediated inhibition in a cell line or whole organism, gene expression is conveniently assayed by use of a reporter or drug resistance gene whose protein product is easily assayed. Such reporter genes include acetohydroxyacid synthase (AHAS), alkaline phosphatase (AP), beta galactosidase (LacZ), beta glucoronidase (GUS), chloramphenicol acetyltransferase (CAT), green fluorescent protein (GFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentamycin, hygromycin, kanamycin, lincomycin, methotrexate, phosphinothricin, puromycin, and tetracyclin.

The practice of the present invention employs, unless otherwise indicated, conventional techniques of immunology, biochemistry, chemistry, molecular biology, microbiology, cell biology, genomics and recombinant DNA, which are within the skill of the art. See Sambrook, Fritsch and Maniatis, MOLECULAR CLONING: A LABORATORY MANUAL, 2nd edition (1989); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)).

"Recombinase Mediated Cassette Exchange" (RMCE) is based on the features of site-specific recombination processes (SSRs), the procedure permits the systematic, repeated modification of higher eukaryotic genomes by targeted integration. For RMCE, this is achieved by the clean exchange of a preexisting gene cassette for an analogous cassette carrying the "gene of interest" (GOI). The exchange of genetic cassettes ('flip' step) is enabled by a recombinase (Tip') from yeast. Part B shows mutants (Fn) of the naturally occurring 48 bp FRT-site (F). If a gene cassette is flanked by a set of these sites (F and Fn, for example) it can change places, by double-reciprocal recombination, with a second cassette that is part of an exchange plasmid. A model experiment is shown in part C, in which an 'empty' cell is modified by either a standard transfection approach or by RMCE. Please note that in the first case multiple genomic sites are hit, each giving raise to a different expression level (cf. the broad distribution of green dots). If a pre-defined genomic address is used to introduce the same gene reporter, each clone derived from such an event shows comparable expression characteristics.

"Recombinases" are genetic recombination enzymes. DNA recombinases are widely used in multicellular organisms to manipulate the structure of genomes, and to control gene expression. These enzymes, derived from bacteria and fungi, catalyze directionally sensitive DNA exchange reactions between short (30-40 nucleotides) target site sequences that are specific to each recombinase. These reactions enable four basic functional modules, excision/insertion, inversion, translocation and cassette exchange, which have been used individually or combined in a wide range of configurations to control gene expression.

The "tet inducible system" is a method of inducible gene expression where transcription is reversibly turned on or off in the presence of the antibiotic tetracycline or one of its derivatives (e.g. doxycycline). In nature, the Ptet promoter expresses TetR, the repressor, and TetA, the protein that pumps tetracycline antibiotic out of the cell. The difference between Tet-On and Tet-Off is not whether the transactivator turns a gene on or off, as the name might suggest; rather, both proteins activate expression. The difference relates to their respective response to doxycycline (Dox, a more stable tetracycline analogue); Tet-Off activates expression in the absence of Dox, whereas Tet-On activates in the presence of Dox. The Tet-On Advanced transactivator (also known as rtTA2S-M2) is an alternative version of Tet-On that shows reduced basal expression, and functions at a 10-fold lower Dox concentration than Tet-Off. In addition, its expression is considered to be more stable in eukaryotic cells due to being human codon optimized and utilizing 3 minimal transcriptional activation domains. Tet-On 3G (also known as rtTA-V16[Clontech Laboratories, Inc.]) is similar to Tet-On Advanced but was derived from rtTA2S-S2 rather than rtTA2S-M2. It is also human codon optimized and composed of 3 minimal VP16 activation domains. However, the Tet-On 3G protein has 5 amino acid differences compared to Tet-On Advanced which appear to increase its sensitivity to Dox even further. Tet-On 3G is sensitive to 100-fold less Dox and is 7-fold more active than the original Tet-On. Other systems such as the T-REx system by Life Technologies work in a different fashion. The gene of interest is flanked by an upstream CMV promoter and two TetO2 sites. Expression of the gene of interest is repressed by the high affinity binding of TetR homodimers to each TetO2 sequences in the absence of tetracycline. Introduction of tetracycline results in binding of one tetracycline on each TetR homodimer followed by release of TetO2 by the TetR homodimers. Unbinding of TetR homodimers and TetO2 result in derepression of the gene of interest.

"Transduction of foreign DNA material" is the process by which genetic material, e.g. DNA or siRNA, is inserted into a cell by a virus. Common techniques in molecular biology are the use of viral vectors (including bacteriophages), electroporation, or chemical reagents that increase cell permeability. Transfection and transformation are also common ways to insert DNA into a cell.

"Blastocyst injection" generate of chimeric rat, i.e. mixtures of ES cell-derived and host blastocyst-derived tissues. The goal is a chimera with high contribution of ES cell-derived tissue, including the germline. ES cells for injection can be prepared. Blastocysts (from strain C57BL/6 for 129-derived ES cells; from strain albino C57BL/6 for C57BL/6-derived ES cells) may be injected with gene-modified ES cells and implanted into recipient dams. Chimeric males may then be used for experimentation.

A variety of cells isolated or obtained from other sources (e.g., commercial sources or cell banks), can be used in accordance with the invention. Non-limiting examples of such cells include somatic cells such as immune cells (T-cells, B-cells, Natural Killer (NK) cells), blood cells (erythrocytes and leukocytes), endothelial cells, epithelial cells, neuronal cells (from the central or peripheral nervous systems), muscle cells (including myocytes and myoblasts from skeletal, smooth or cardiac muscle), connective tissue cells (including fibroblasts, adipocytes, chondrocytes, chondroblasts, osteocytes and osteoblasts) and other stromal cells (e.g., macrophages, dendritic cells, thymic nurse cells, Schwann cells, etc.). Eukaryotic germ cells (spermatocytes and oocytes) can also be used in accordance with the invention, as can the progenitors, precursors and stem cells that give rise to the above-described somatic and germ cells. These cells, tissues and organs can be normal, or they can be pathological such as those involved in diseases or physical disorders, including but not limited to immune related diseases, chronic inflammation, autoimmune responses, infectious diseases (caused by bacteria, fungi or yeast, viruses (including HIV) or parasites), in genetic or biochemical pathologies (e.g., cystic fibrosis, hemophilia, Alzheimer's disease, schizophrenia, muscular dystrophy, multiple sclerosis, etc.), or in carcinogenesis and other cancer-related processes. Rat pluripotent cells, including embryonic cells, spermatogonial stem cells, embryonic stein cells, and iPS cells are envisioned. Rat somatic cells are also envisioned.

Inducible CRISPR/Cas9 and RNAi Methods

The Inducible CRISPR/Cas9 and RNAi method 100 described in PCT application serial no. PCT/US2016/051992, herein incorporated by reference in its entirety, is the novel combination of specific gene editing events (via CRISPR/Cas9, zinc fingers, TALENs, etc.) and RNA interference to be used sequentially and/or in combination in the same biological system (or organism or animal model). The first method is the CRISPR/Cas9 genome editing tool, which initiates DNA cleavage at precise genomic locations to induce DNA repair by one of two mechanisms: NHEJ (non-homologous end joining) or HDR (homology directed repair). In the case of NHEJ, these gene editing events are used to generate gene mutations by random insertion or deletions of nucleotides (INDELS) at desired genomic regions that may predispose the biological system or animal model to disease pathogenesis or expression of a desired phenotype. In the case of HDR, a donor template containing homologous regions along with the desired mutation is also delivered to induce a homologous recombination event and incorporation of the donor template into the genome. The donor template may contain any number of transgene cassettes to alter the genomic DNA including but not limited to cDNAs, point mutation sequences, reporters, miRNAs, etc. Cas9-mediated DNA cleavage can be induced at a precise time by expressing Cas9 from an inducible promoter, such as a TRE (tet-responsive element) promoter. This configuration will drive Cas9 expression by the addition of doxycycline (a tetracycline analog) to the system or food or drinking water of an animal (Dow, L. E., Fisher, J., O'Rourke, K. P., Muley, A., Kastenhuber, E. R., Livshits, G., Tschaharganeh, D. F., Socci, N. D., and Lowe, S. W. (2015). Inducible in vivo genome editing with CRISPR-Cas9. Nat Biotechnol 33, 390-394). In contrast, the tGFP-shRNA construct is in the opposite orientation (as shown in FIG. 1 described in PCT application serial no. PCT/US2016/051992) and not in frame with the promoter, so its expression will not be induced initially following doxycycline treatment. Once the CRISPR/Cas9-induced gene editing process has occurred, the second method to be applied is a recombination system, such as CRE/Lox or FLP/FRT or DRE/Rox, whereby inverted repeats flank the Cas9-CRE ERT2 construct (as shown in FIG. 1 described in PCT application serial no. PCT/US2016/051992) and enable precise recombination to occur following the addition of tamoxifen (or estrogen analog) (Siegel, R. W., Jain, R., and Bradbury, A. (2001). Using an in vivo phagemid system to identify non-compatible loxP sequences. FEBS Lett 499, 147-153.). A number of configurations of the inverted repeats or recombination sequeneces may be used Depending on the location and orientation of the loxP sequences, specific recombination events can occur (as shown in FIGS. 1-4 described in PCT application serial no. PCT/US2016/051992) (Matsuda, T., and Cepko, C. L. (2007). Controlled expression of transgenes introduced by in vivo electroporation. Proc Natl Acad Sci USA 104, 1027-1032.; Siegel, R. W., Jain, R., and Bradbury, A. (2001). Using an in vivo phagemid system to identify non-compatible loxP sequences. FEBS Lett 499, 147-153). As depicted in FIG. 2 described in PCT application serial no. PCT/US2016/051992, recombination of the loxP sites by CRE will cause excision and/or inversion of the DNA construct such that the tGFP-shRNA construct will be oriented in the appropriate 5' to 3' direction to enable the functionality of the third method, inducible RNA interference. loxP and 1ox2272 may be substituted for additional inverted repeats and recombination systems (ie. Flp/FRT, PhiC3 1/a ttP/B systems/Dre/Rox). Tamoxifen may be replaced by other estrogen or hormone molecules depending on the recombinase selected. tGFP may be substituted for any reporter or DNA sequence to monitor inhibition of gene expression. Finally, after the inversion has occurred, treatment with doxycycline will activate expression of a GFP-tagged shRNA construct that will induce RNAi-mediated gene silencing of the specific gene of interest (Dickins, R. A., McJunkin, K., Hernando, E., Premsrirut, P. K., Krizhanovsky, V., Burgess, D. J., Kim, S. Y., Cordon-Cardo, C., Zender, L., Hannon, G. J., et al. (2007). Tissue-specific and reversible RNA interference in transgenic mice. Nat Genet 39, 914-921; Premsrirut, P. K., Dow, L. E., Kim, S. Y., Camiolo, M., Malone, C. D., Miething, C., Scuoppo, C., Zuber, J., Dickins, R. A., Kogan, S. C., et al. (2011). A rapid and scalable system for studying gene function in mice using conditional RNA interference. Cell 145, 145-158.).

The Inducible CRISPR/Cas9 and RNAi 100 method enables delivery of a single DNA construct into a biological system to facilitate efficient CRISPR/Cas9 mediated gene editing and RNAi interference-mediated gene silencing in combination. Such a system would enable, for example, the induction of a specific disease or phenotype in a biological system or animal model, followed by RNAi-mediated gene silencing, which can effectively model therapeutic intervention. The simplicity of the all-in-one design enables rapid generation of animal models of disease such that only 2 alleles are required for activation of the system: (1) the all-in-one FLEx system (FIG. 1 described in PCT application serial no. PCT/US2016/051992), and (2) a tet-transactivator (either Tet-off; tTA or Tet-on; rtTA).

The Inducible CRISPR/Cas9 and RNAi method is unique in that it enables both inducible CRISPR/Cas9 and inducible RNAi to be used in the same system with expression from the same TRE promoter. It is conceivable that inducible CRISPR/Cas9 and inducible RNAi in combination could be achieved by combining two unique inducible expression systems, such as the SparQTM cumate switch (System Biosciences, Inc.) or the RheoSwitch inducible expression system (New England BioLabs), however, these systems have not been thoroughly tested in vivo animal models and are not as routinely utilized as the Tet-inducible system (Abe, T., and Branzei, D. (2014). High levels of BRC4 induced by a Tet-On 3G system suppress DNA repair and impair cell proliferation in vertebrate cells. DNA Repair (Amst) 22, 153-164; Gossen and Bujard, 1992; Loew, R., Heinz, N., Hampf, M., Bujard, H., and Gossen, M. (2010). Improved Tet-responsive promoters with minimized background expression. BMC Biotechnol 10, 81.) and characterization of their expression patterns in vivo have yet to be determined. Furthermore, whether or not two independent inducible expression systems can be combined into an all-in-one expression vector is unknown, as promoter interference may hinder this possibility. Therefore, the Inducible CRISPR/Cas9 and RNAi method uses Cas9 and shRNA expression to be induced sequentially rather than simultaneously. The purpose of this is to allow mutagenesis to occur initially and reserving the induction of shRNA expression following disease pathogenesis or phenotype manifestation.

The Inducible CRISPR/Cas9 and RNAi system may also include a novel shRNA targeting Cas9 (shCas9) to prevent high levels of Cas9 expression from the TRE promoter (FIG. 1). It has been shown that high and/or continuous levels of Cas9 can be detrimental to cells, and therefore to limit its expression, the Inducible CRISPR/Cas9 and RNAi method may include an shRNA on the 3' UTR of the Cas9 expression cassette. In addition to controlling the abundant overexpression from the TRE promoter, the shCas9 also serves to control any leaky expression from the TRE promoter itself in the absence of doxycycline (for the Tet-on system) (McJunkin, K., Mazurek, A., Premsrirut, P. K., Zuber, J., Dow, L. E., Simon, J., Stillman, B., and Lowe, S. W. (2011). Reversible suppression of an essential gene in adult mice using transgenic RNA interference. Proc. Natl. Acad. Sci. USA 108, 7113-7118). In a number of cases, the original TRE promoter has been demonstrated to be leaky, such that minimal expression does occur in the absence of doxycycline, and therefore multiple newer generations of promoters (TREtight and TRE3G) have been developed (Abe and Branzei, 2014; Loew et al., 2010). Unfortunately, while these promoters serve to control leakiness, there regulation can be too tight in some cases, such that expression becomes restricted in specific tissues in animal models (McJunkin et al., 2011). Nonetheless, TRE can be replaced with any promoter including the newer TREtight and TRE3G promoters.

The Inducible CRISPR/Cas9 and RNAi system is also unique in that it is highly adaptable. A number of versions can be utilized but the system is not limited to only what has been depicted. For example, a number of U6-gRNA cassettes may be expressed upstream of the TRE promoter. U6-RNAs may be cloned in tandem, such as U6-gRNA-gRNA—U6-gRNA-gRNA—U6-gRNA-gRNA. U6 may be substituted by other pol III promoters or regulatory elements, as described previously. The gRNAs may be directed to multiple genes (Dow, L. E., Fisher, J., O'Rourke, K. P., Muley, A., Kastenhuber, E. R., Livshits, G., Tschaharganeh, D. F., Socci, N. D., and Lowe, S. W. (2015). Inducible in vivo genome editing with CRISPR-Cas9. Nat Biotechnol 33, 390-394). The TRE promoter may be replaced by a TREtight (Clontech Laboratories, Mountain View, CA) or TRE3G (Clontech Laboratories, Mountain View, CA) promoter as shown in FIGS. 5-6 described in PCT application serial no. PCT/US2016/051992, or ultimately another inducible promoter once tested and characterized. The TRE promoter may be replaced with a tissue-specific or ubiquitous promoter or regulatory element. The shCas9 may or may not be present depending on the promoter and whether abundant overexpression and/or leakiness is a concern. In some cases, CRE or CRE ERT2 may be delivered ectopically, for example, in the form of adenoviruses or lentiviruses containing CRE. In normal cells, CreER T2 is cytoplasmic and inactive, however addition of tamoxifen activates the recombinase activity of the fusion protein.

The tetracycline (tet)-regulated system controls expression of RNAi constructs from tetracycline-responsive promoters (TRE) (Dickins, R. A., Hemann, M. T., Zilfou, J. T., Simpson, D. R., Ibarra, I., Hannon, G. J., & Lowe, S. W. Probing tumor phenotypes using stable and regulated synthetic microRNA precursors. Nature Genetics. 37 (2005) 1289-95). Briefly, the tet-based system requires the additional expression of a tet-transactivator protein (tTA or rtTA) (Furth, P. A., St. Onge, L., Boger, H., Gruss, P., Gossen, M., Kistner, A., Bujard, H. & Hennighausen, L. Temporal control of gene expression in transgenic mice by a tetracycline-responsive promoter. Proc. Natl. Acad. Sci. 27 (1994) 9302-9306). In the presence of tTA (tet-off), TRE driven expression is active, but is shutdown once doxycycline (a tetracycline derivative) is administered. The reverse is true for rtTA (tet-on), where transcription is active only in the presence of doxycycline. In mice, tTA or rtTA expression can be limited with use of tissue-specific promoters, making it possible to restrict knockdown to particular tissues.

Other features that may be adapted are the recombination systems. Both CRE/loxP and Flp/FRT systems have been thoroughly described and tested both in vitro and in vivo (Boniface, E. J., Lu, J., Victoroff, T., Zhu, M., and Chen, W. (2009). FlEx-based transgenic reporter lines for visualization of Cre and Flp activity in live zebrafish. Genesis 47, 484-491; Branda, C. S., and Dymecki, S. M. (2004). Talking about a revolution: The impact of site-specific recombinases on genetic analyses in mice. Dev Cell 6, 7-28) and may be substituted for one another. Additional efficient recombination systems (KD, R, B2, B3 or DRE recombinases) may be discovered in the near future and may be used in place of CRE/loxP (Nern, A., Pfeiffer, B. D., Svoboda, K., and Rubin, G. M. (2011). Multiple new site-specific recombinases for use in manipulating animal genomes. Proc Natl Acad Sci U SA 108, 14198-14203). The IRES sequence may also be interchangeable with P2A (Kim, J. H., Lee, S. R., Li, L. H., Park, H. J., Park, J. H., Lee, K. Y., Kim, M. K., Shin, B. A., and Choi, S. Y. (2011). High cleavage efficiency of a 2A peptide derived from porcine teschovirus-1 in human cell lines, zebrafish and mice. PLoS One 6, e18556) or any other ribosomal entry sequence. The turboGFP (tGFP) depicted maybe substituted for any other reporter such as an antibiotic resistance cassette, fluorescence reporter, or even another cDNA. In fact, it may be replaced by random DNA sequence so long as it provides a spacer element between the promoter and the shRNA to induce increased RNAi efficiency (Premsrirut et al., 2011).

CRISPR/Cas9-Mediated Engineering of RNAi Models

Figure 2B:
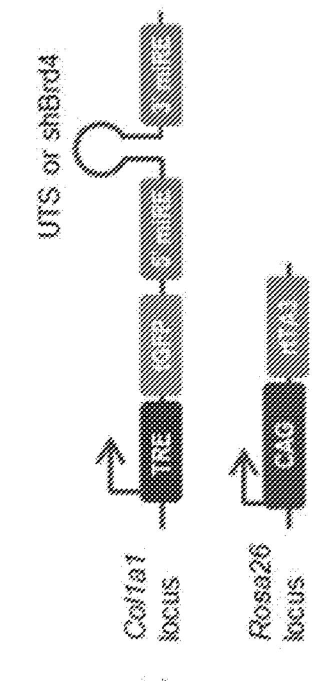
FIG. 2B is a schematic diagram of founder strains to be generated according to one embodiment.
Figure 2A:
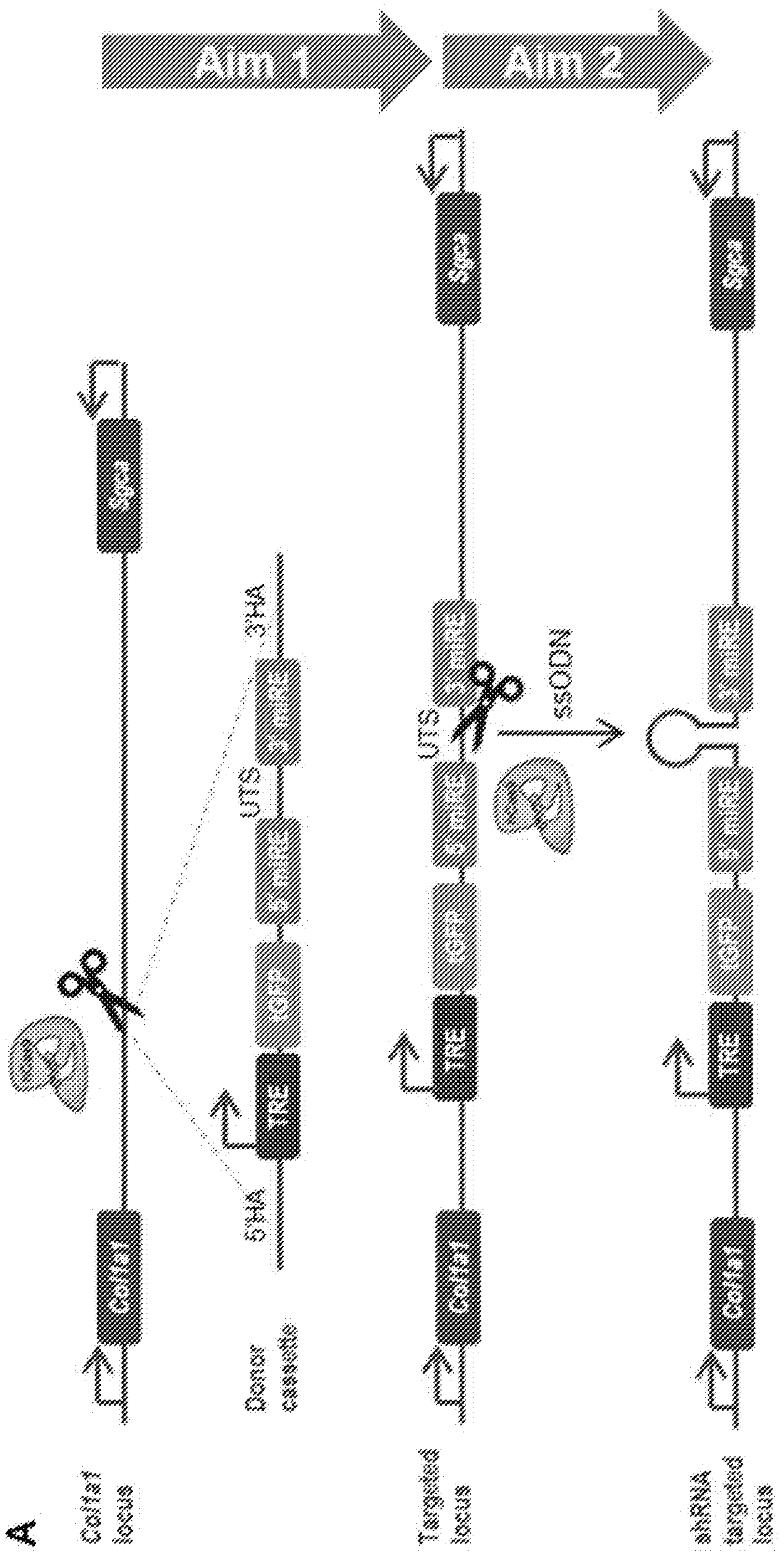
FIG. 2A is a diagram of the two step approach to RNAi model creation using CRISPR/Cas9, where founder animals are first created by knock-in of the donor cassette and in a second targeting event, CRISPR-mediated HDR of ssODN is used to facilitate insertion of a unique shRNA sequence.

The present invention incorporates CRISPR/Cas9 genome engineering, identified pitfalls and developed new methods and standardized protocols to facilitate the creation of nearly any desired model. The present invention develops a transformative platform technology for the creation of CRISPR/Cas9-RNAi rat, where CRISPR rapidly induces complex mutation patterns found in human tumors and RNAi evaluates novel targets in the same animal. The RNAi rat pipeline may be transformed and use Cas9-mediated insertion of small donor templates harboring only the unique shRNA sequence (FIG. 2A). By doing so, the traditional ESC targeting platform is substituted and direct injections into embryos is performed, thus decreasing both the time and costs of production dramatically. The present invention comprises CRISPR/Cas9 methodologies for RNAi rat production and the reversible gene-silencing technology is applied to the rat system. By doing so, research in areas where rat is the preferred rodent model will be transformed. The ability to better model clinical disorders and evaluate genetic and environmental stimuli in the more relevant model organism will increase the reliability of animal models for predicting drug responses in humans and push drug discovery research beyond its current limitations.

1. CRISPR

Synergizing CRISPR/Cas9 and RNAi Toolbox for Model Creation

The present invention may employ new CRISPR/Cas9 tools, including CRISPR interference (CRISPRi)[32,33], CRISPR activators (CRISPRa)[34], and other Cas9 fusions to enable modulation of chromatin[35]. The present invention synergizes emerging CRISPR technologies with established and optimized RNAi tools, harnessing the strengths of each system, and applying them in parallel to create new powerful CRISPR-RNAi mouse models for gene target evaluation. More than 100 new models using CRISPR/Cas9-mediated gene editing have been generated by the present invention, which in several cases involved the engineering of sophisticated alleles such as large insertions (>10 kb), the introduction of multiple reporters or loxP sites at different genomic loci, and the direct construction of specific point mutations and regulatable shRNA cassettes. The present invention comprises model creation beyond mice and into other species, including, but not limited to rats. The present invention comprises CRISPR/Cas9 genetic engineering, molecular biology, RNAi technologies, embryo manipulation and animal model creation. The requirements for rat models will be established and a pipeline for rapid RNAi rat model creation. The present invention comprises validating shRNAs and selecting potent shRNAs targeting rat genes that can be easily inserted into the pre-engineered rat embryos that are designed for systematic insertion, mirroring the mouse model system (FIG. 2A). The present invention will define a new paradigm to not only accelerate the creation of novel rat models for drug discovery research, but also open a new avenue to study gene function in broader disease contexts.

Most recently, a new gene targeting tool has been developed in microbial and mammalian systems based on the cluster regularly interspaced short palindromic repeats (CRISPR)-associated nuclease system. The CRISPR-associated nuclease is part of adaptive immunity in bacteria and archaea. The Cas9 endonuclease, a component of *Streptococcus pyogenes* type II CRISPR/Cas system, forms a complex with two short RNA molecules called CRISPR RNA (crRNA) and transactivating crRNA (transcrRNA), which guide the nuclease to cleave non-self DNA on both strands at a specific site. The crRNA-transcrRNA heteroduplex could be replaced by one chimeric RNA (so-called guide RNA (gRNA)), which can then be programmed to targeted specific sites. The minimal constrains to program gRNA-Cas9 is at least 15-base-pairing between engineered 5"-RNA and targeted DNA without mismatch, and an NGG motif (so-called protospacer adjacent motif or PAM) follows the base-pairing region in the targeted DNA sequence. Generally, 15-22 nt in the 5"-end of the gRNA region is used to direct Cas9 nuclease to generate DSBs at the specific site. The CRISPR/Cas system has been demonstrated for genome editing in human, mice, zebrafish, yeast and bacteria.

The said method may comprise gene editing and expressing DNA molecules encoding the one or more gene products an engineered, non-naturally occurring vector system comprising one or more vectors comprising: a) a first regulatory element operably linked to one or more Clustered Regularly Interspaced Short Palindromic Repeats (CRISPR)-CRISPR associated (Cas) system guide RNAs that hybridize with target sequences in genomic loci of the DNA molecules encoding the one or more gene products, b) a second regulatory element operably linked to a Type-II Cas9 protein, wherein components (a) and (b) are located on same or different vectors of the system, whereby the guide RNAs target the genomic loci of the DNA molecules encoding the one or more gene products and the Cas9 protein cleaves the genomic loci of the DNA molecules encoding the one or more gene products, whereby expression of the one or more gene products is altered; and, wherein the Cas9 protein and the guide RNAs do not naturally occur together.

The CRISPR/Cas-like sequence can be derived from a CRISPR/Cas type I, type II, or type III system. Non-limiting examples of suitable CRISPR/Cas proteins include Cas3, Cas4, Cas5, Cas5e (or CasD), Cash, Cas6e, Cas6f, Cas7, Cas8a1, Cas8a2, Cas8b, Cas8c, Cas9, Cas10, Cas10d, CasF, CasG, CasH, Csy1, Csy2, Csy3, Cse1 (or CasA), Cse2 (or CasB), Cse3 (or CasE), Cse4 (or CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csz1, Csx15, Csf1, Csf2, Csf3, Csf4, and Cu1966.

In one embodiment, the CRISPR/Cas-like protein of the fusion protein is derived from a type II CRISPR/Cas system. In exemplary embodiments, the CRISPR/Cas-like protein of the fusion protein is derived from a Cas9 protein. The Cas9 protein can be from *Streptococcus pyogenes, Streptococcus thermophilus, Streptococcus* sp., Nocardiopsis dassonvillei, *Streptomyces* pristinaespiralis, *Streptomyces viridochromo-*

*genes, Streptomyces viridochromogenes, Streptosporangium roseum, Streptosporangium roseum, Alicyclobacillus acidocaldarius, Bacillus pseudomycoides, Bacillus selenitireducens, Exiguobacterium sibiricum, Lactobacillus delbrueckii, Lactobacillus salivarius*, Microscilla marina, Burkholderiales bacterium, *Polaromonas naphthalenivorans, Polaromonas* sp., Crocosphaera *watsonii*, Cyanothece sp., Microcystis *aeruginosa*, Synechococcus sp., Acetohalobium arabaticum, Ammonifex degensii, Caldicelulosiruptor becscii, Candidatus Desulforudis, *Clostridium botulinum, Clostridium difficile, Finegoldia magna, Natranaerobius thermophilus*, Pelotomaculum the rmopropionicum, Acidithiobacillus caldus, Acidithiobacillus ferrooxidans, Allochromatium *vinosum, Marinobacter* sp., Nitrosococcus *halophilus, Nitrosococcus watsoni, Pseudoalteromonas haloplanktis*, Ktedonobacter racemifer, Methanohalobium evestigatum, *Anabaena variabilis, Nodularia spumigena, Nostoc* sp., Arthrospira maxima, Arthrospira *platensis*, Arthrospira sp., Lyngbya sp., Microcoleus chthonoplastes, Oscillatoria sp., Petrotoga *mobilis, Thermosipho africanus*, or Acaryochloris marina.

In general, CRISPR/Cas proteins comprise at least one RNA recognition and/or RNA binding domain. RNA recognition and/or RNA binding domains interact with the guiding RNA. CRISPR/Cas proteins can also comprise nuclease domains (i.e., DNase or RNase domains), DNA binding domains, helicase domains, RNAse domains, protein-protein interaction domains, dimerization domains, as well as other domains.

The CRISPR/Cas-like protein can be a wild type CRISPR/Cas protein, a modified CRISPR/Cas protein, or a fragment of a wild type or modified CRISPR/Cas protein. The CRISPR/Cas protein can be modified to increase nucleic acid binding affinity and/or specificity, alter an enzymatic activity, and/or change another property of the protein. For example, nuclease (i.e., DNase, RNase) domains of the CRISPR/Cas protein can be modified, deleted, or inactivated. Alternatively, the CRISPR/Cas protein can be truncated to remove domains that are not essential for the function of the fusion protein. The CRISPR/Cas protein can also be truncated or modified to optimize the activity of the effector domain of the fusion protein.

In some embodiments, the CRISPR/Cas-like protein of the fusion protein can be derived from a wild type Cas9 protein or fragment thereof. In other embodiments, the CRISPR/Cas-like protein of the fusion protein can be derived from modified Cas9 protein. For example, the amino acid sequence of the Cas9 protein can be modified to alter one or more properties (e.g., nuclease activity, affinity, stability, etc.) of the protein. Alternatively, domains of the Cas9 protein not involved in RNA-guided cleavage can be eliminated from the protein such that the modified Cas9 protein is smaller than the wild type Cas9 protein.

In general, a Cas9 protein comprises at least two nuclease (i.e., DNase) domains. For example, a Cas9 protein can comprise a RuvC-like nuclease domain and a HNH-like nuclease domain. The RuvC and HNH domains work together to cut single strands to make a double-stranded break in DNA. (Jinek et al., Science, 337: 816-821). In some embodiments, the Cas9-derived protein can be modified to contain only one functional nuclease domain (either a RuvC-like or a HNH-like nuclease domain). For example, the Cas9-derived protein can be modified such that one of the nuclease domains is deleted or mutated such that it is no longer functional (i.e., the nuclease activity is absent). In some embodiments in which one of the nuclease domains is inactive, the Cas9-derived protein is able to introduce a nick into a double-stranded nucleic acid (such protein is termed a "nickase"), but not cleave the double-stranded DNA. For example, an aspartate to alanine (D10A) conversion in a RuvC-like domain converts the Cas9-derived protein into a nickase. Likewise, a histidine to alanine (H840A) conversion in a HNH domain converts the Cas9-derived protein into a nickase.

In other embodiments, both of the RuvC-like nuclease domain and the HNH-like nuclease domain can be modified or eliminated such that the Cas9-derived protein is unable to nick or cleave double stranded nucleic acid. In still other embodiments, all nuclease domains of the Cas9-derived protein can be modified or eliminated such that the Cas9-derived protein lacks all nuclease activity.

In any of the above-described embodiments, any or all of the nuclease domains can be inactivated by one or more deletion mutations, insertion mutations, and/or substitution mutations using well-known methods, such as site-directed mutagenesis, PCR-mediated mutagenesis, and total gene synthesis, as well as other methods known in the art. In an exemplary embodiment, the CRISPR/Cas-like protein of the fusion protein is derived from a Cas9 protein in which all the nuclease domains have been inactivated or deleted.

Compositions and methods for making and using CRISPR-Cas systems are described in U.S. Pat. No. 8,697,359, entitled "CRISPR-CAS SYSTEMS AND METHODS FOR ALTERING EXPRESSION OF GENE PRODUCTS," which is incorporated herein in its entirety.

In recent years, sequence-specific nucleases have been developed to increase the efficiency of gene targeting or genome editing in animal and plant systems. Among them, zinc finger nucleases (ZFNs) and transcription activator-like effector nucleases (TALENs) are the two most commonly used sequence-specific chimeric proteins. Once the ZFN or TALEN constructs are introduced into and expressed in cells, the programmable DNA binding domain can specifically bind to a corresponding sequence and guide the chimeric nuclease (e.g., the Fokl nuclease) to make a specific DNA strand cleavage. A pair of ZFNs or TALENs can be introduced to generate double strand breaks (DSBs), which activate the DNA repair systems and significantly increase the frequency of both nonhomologous end joining (NHEJ) and homologous recombination (HR).

In general, single zinc-finger motif specifically recognizes 3 bp, and engineered zinc-finger with tandem repeats can recognize up to 9-36 bp. However, it is quite tedious and time-consuming to screen and identify a desirable ZFN. Despite its drawbacks, ZFN has been used in plants to introduce small mutations, gene deletion, or foreign DNA integration (gene replacement/knock-in) at the specific genomic site. In contrast with the zinc finger protein, TALEs are derived from the plant pathogenic bacteria *Xanthomonas* and contain 34 amino acid tandem repeats in which repeat-variable diresidues (RVDs) at positions 12 and 13 determine the DNA-binding specificity. As a result, TALENs with 16-24 tandem repeats can specifically recognize 16-24 by genomic sequences and the chimeric nuclease can generate DSBs at specific genomic sites. TALEN-mediated genome editing has already been demonstrated in many organisms including yeast, animals, and plants.

Engineered meganucleases may also be used as the gene editing system. Engineered meganucleases are enzymes in the endonuclease family which are characterized by their capacity to recognize and cut large DNA sequences (from 14 to 40 base pairs). The most widespread and best known meganucleases are the proteins in the LAGLIDADG family, which owe their name to a conserved amino acid sequence.

2. Recombination System

This example describes a system for creating genetically defined RNAi using Cre-mediated recombination to stably invert an integrated a single RNAi expression cassette into the desired orientation at a defined locus in the rat genome. This technique will minimize clonal variation due to random integration events seen in other studies and should allow for the efficient creation of "epi-allelic" series of RNAi constructs, as well as an inducible RNAi system. Applicants have adapted a system developed for chromosomal engineering in mice to mediate the integration of a single short hairpin RNA (shRNA) expression cassette in rat ES cells. This strategy relies on the ability to integrate a "donor" plasmid, containing a shRNA expression construct, into an "acceptor" locus and through the transient expression of Cre recombinase, reorient the cassette in frame with the promoter.

ERT2-CRE-ERT2 may or may not be present; tamoxifen may be replaced for CRE when ERT2-CRE-ERT2 is not present—TRE may be substituted for any promoter or inducible promoter.

loxP and lox2272 may be substituted for additional inverted repeats and recombination systems (i.e. Flp/FRT, PhiC31/attP/B, Dre/Rox systems); tamoxifen may be replaced when using a non-ERT2 system.

3. RNAi

The RNAi of Today is not the RNAi of the Past

We have continued to demonstrate the power of RNAi in vivo, showcasing its ability to model small molecule inhibition of specific gene targets and pinpoint potential toxicities associated with gene silencing13,15-18. From decades of innovation and step-wise improvements, we have brought RNAi to its highest peak thus far, now with a new SplashRNA algorithm26, validation methods27 and the optimized miRE backbone28 at our disposal, we are able to identify the most potent shRNA sequences to target any gene and incorporate them into the most effective scaffold for RNAi-mediated gene silencing. Of note, the superiority of our miRE design has also been confirmed in a recent technical report by Genentech, which revealed vast performance differences between RNAi platforms, as well as some major design flaws in commonly used RNAi reagents29. Recently, we developed a new tandem shRNA approach, we call multEmiR, that enables potent inhibition of multiple targets simultaneously in vivo and mirror drugs that inhibit protein families rather than single enzymes. To this end, MultEmiR mice provide an avenue for critical preclinical evaluation of multi-target inhibition or combination therapies. We and others have successfully employed RNAi in combination with drug therapy to provide evidence for combination treatments and/or identify potential synthetic lethal interactions18.

In certain aspects, the invention provides systems which use RNA interference to stably, conditionally (e.g., with spatial, temporal, and/or reversible control) and specifically target and decrease the expression of one or more target genes in cells. Recent work has shown that the RNA interference effects of exogenously provided dsRNAs can be recapitulated in mammalian cells by the expression of single RNA molecules which fold into stable "hairpin" structures (Paddison, P. J., A. A. Caudy, and G. J. Hannon, Stable suppression of gene expression by RNAi in mammalian cells. Proc Natl Acad Sci USA, 2002. 99(3): p. 1443-8). Transient transfection of plasmids encoding small "hairpin" RNAs (shRNAs) can achieve a near complete reduction in the levels of a specific protein in a cell. Applicants have now demonstrated that shRNAs can be stably introduced into mammalian cells, preferably in a site-specific manner, introduced into a living organism and propagated without significant loss of the RNA interference effect. Furthermore, the stably integrated RNAi constructs may be conditionally expressed (e.g., expression may be turned on or off in a tissue-specific or reversible manner). A variety of experiments substantiating the discovery are presented in detail in the Examples below.

Many embodiments of the invention employ single-stranded RNA molecules containing an inverted repeat region that causes the RNA to self-hybridize, forming a hairpin structure. shRNA molecules of this type may be encoded in RNA or DNA vectors. The term "encoded" is used to indicate that the vector, when acted upon by an appropriate enzyme, such as an RNA polymerase, will give rise to the desired shRNA molecules (although additional processing enzymes may also be involved in producing the encoded shRNA molecules). As described herein, vectors comprising one or more encoded shRNAs may be transfected into cells ex vivo, and the cells may be introduced into mammals. The expression of shRNAs may be constitutive or regulated in a desired manner. Other technologies for achieving RNA interference in vivo were unreliable; certain constructs were expressible in stem cells but not in differentiated cells, or vice versa. Technology described herein makes it possible to achieve either constitutive or highly regulated expression of shRNAs in vivo across the spectrum of cell types, thereby permitting tightly controlled regulation of target genes in vivo.

A double-stranded structure of an shRNA is formed by a single self-complementary RNA strand. RNA duplex formation may be initiated either inside or outside the cell. Inhibition is sequence-specific in that nucleotide sequences corresponding to the duplex region of the RNA are targeted for genetic inhibition. shRNA constructs containing a nucleotide sequence identical to a portion, of either coding or non-coding sequence, of the target gene are preferred for inhibition. RNA sequences with insertions, deletions, and single point mutations relative to the target sequence have also been found to be effective for inhibition. Because 100% sequence identity between the RNA and the target gene is not required to practice the present invention, the invention has the advantage of being able to tolerate sequence variations that might be expected due to genetic mutation, strain polymorphism, or evolutionary divergence. Sequence identity may be optimized by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). Greater than 90% sequence identity, or even 100% sequence identity, between the inhibitory RNA and the portion of the target gene is preferred. Alternatively, the duplex region of the RNA may be defined functionally as a nucleotide sequence that is capable of hybridizing with a portion of the target gene transcript (e.g., 400 mM NaCl, 40 mM PIPES pH 6.4, 1 mM EDTA, 50° C. or 70° C. hybridization for 12-16 hours; followed by washing). In certain preferred embodiments, the length of the duplex-forming portion of an shRNA is at least 20, 21 or 22 nucleotides in length, e.g., corresponding in size to RNA products produced by Dicer-dependent cleavage. In certain embodiments, the shRNA construct is at least 25, 50, 100, 200, 300 or 400 bases in length. In certain embodiments, the shRNA construct is 400-800 bases in length. shRNA constructs are highly tolerant of variation in loop sequence and loop size.

An endogenous RNA polymerase of the cell may mediate transcription of an shRNA encoded in a nucleic acid construct. The shRNA construct may also be synthesized by a bacteriophage RNA polymerase (e.g., T3, T7, SP6) that is expressed in the cell. In preferred embodiments, expression of an shRNA is regulated by an RNA polymerase III promoters; such promoters are known to produce efficient silencing. While essentially any PolII promoters may be used, desirable examples include the human U6 snRNA promoter, the mouse U6 snRNA promoter, the human and mouse H1 RNA promoter and the human tRNA-val promoter. A U6 snRNA leader sequence may be appended to the primary transcript; such leader sequences tend to increase the efficiency of sub-optimal shRNAs while generally having little or no effect on efficient shRNAs. For transcription from a transgene in vivo, a regulatory region (e.g., promoter, enhancer, silencer, splice donor and acceptor, polyadenylation) may be used to regulate expression of the shRNA strand (or strands). Inhibition may be controlled by specific transcription in an organ, tissue, or cell type; stimulation of an environmental condition (e.g., infection, stress, temperature, chemical inducers); and/or engineering transcription at a developmental stage or age. The RNA strands may or may not be polyadenylated; the RNA strands may or may not be capable of being translated into a polypeptide by a cell's translational apparatus. The use and production of an expression construct are known in the art (see also WO 97/32016; U.S. Pat. Nos. 5,593,874, 5,698,425, 5,712,135, 5,789,214, and 5,804,693; and the references cited therein).

In a preferred embodiment, a shRNA construct is designed with 29 bp helices following a U6 snRNA leader sequence with the transcript being produced by the human U6 snRNA promoter. This transcription unit may be delivered via a Murine Stem Cell Virus (MSCV)-based retrovirus, with the expression cassette inserted downstream of the packaging signal. Further information on the optimization of shRNA constructs may be found, for example, in the following references: Paddison, P. J., A. A. Caudy, and G. J. Hannon, Stable suppression of gene expression by RNAi in mammalian cells. Proc Natl Acad Sci USA, 2002. 99(3): p. 1443-8; 13.Brummelkamp, T. R., R. Bernards, and R. Agami, A System for Stable Expression of Short Interfering RNAs in Mammalian Cells. Science, 2002. 21: p. 21; Kawasaki, H. and K. Taira, Short hairpin type of dsRNAs that are controlled by tRNA(Val) promoter significantly induce RNAi-mediated gene silencing in the cytoplasm of human cells. Nucleic Acids Res, 2003. 31(2): p. 700-7; Lee, N. S., et al., Expression of small interfering RNAs targeted against HIV-1 rev transcripts in human cells. Nat Biotechnol, 2002. 20(5): p. 500-5; Miyagishi, M. and K. Taira, U6 promoter-driven siRNAs with four uridine 3' overhangs efficiently suppress targeted gene expression in mammalian cells. Nat Biotechnol, 2002. 20(5): p. 497-500; Paul, C. P., et al., Effective expression of small interfering RNA in human cells. Nat Biotechnol, 2002. 20(5): p. 505-8.

An shRNA will generally be designed to have partial or complete complementarity with one or more target genes (i.e., complementarity with one or more transcripts of one or more target genes). The target gene may be a gene derived from the cell, an endogenous gene, a transgene, or a gene of a pathogen which is present in the cell after infection thereof. Depending on the particular target gene, the nature of the shRNA and the level of expression of shRNA (e.g. depending on copy number, promoter strength) the procedure may provide partial or complete loss of function for the target gene. Quantitation of gene expression in a cell may show similar amounts of inhibition at the level of accumulation of target mRNA or translation of target protein.

"Inhibition of gene expression" refers to the absence or observable decrease in the level of protein and/or mRNA product from a target gene. "Specificity" refers to the ability to inhibit the target gene without manifest effects on other genes of the cell. The consequences of inhibition can be confirmed by examination of the outward properties of the cell or organism (as presented below in the examples) or by biochemical techniques such as RNA solution hybridization, nuclease protection, Northern hybridization, reverse transcription, gene expression monitoring with a microarray, antibody binding, enzyme linked immunosorbent assay (ELISA), Western blotting, radioimmunoassay (MA), other immunoassays, and fluorescence activated cell analysis (FACS). For RNA-mediated inhibition in a cell line or whole organism, gene expression is conveniently assayed by use of a reporter or drug resistance gene whose protein product is easily assayed. Such reporter genes include acetohydroxyacid synthase (AHAS), alkaline phosphatase (AP), beta galactosidase (LacZ), beta glucoronidase (GUS), chloramphenicol acetyltransferase (CAT), green fluorescent protein (GFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentamycin, hygromycin, kanamycin, lincomycin, methotrexate, phosphinothricin, puromycin, and tetracyclin.

Depending on the assay, quantitation of the amount of gene expression allows one to determine a degree of inhibition which is greater than 10%, 33%, 50%, 90%, 95% or 99% as compared to a cell not treated according to the present invention. As an example, the efficiency of inhibition may be determined by assessing the amount of gene product in the cell: mRNA may be detected with a hybridization probe having a nucleotide sequence outside the region used for the inhibitory double-stranded RNA, or translated polypeptide may be detected with an antibody raised against the polypeptide sequence of that region.

As shown in FIGS. 1-6 as described in PCT application PCT/US2016/051992, shGOI=shRNA targeting a gene of interest, may also be an shRNA within a miRNA backbone, such as miR30.

As disclosed herein, the present invention is not limited to any type of target gene or nucleotide sequence. The following classes of possible target genes are listed for illustrative purposes: developmental genes (e.g., adhesion molecules, cyclin kinase inhibitors, Writ family members, Pax family members, Winged helix family members, Hox family members, cytokines/lymphokines and their receptors, growth/differentiation factors and their receptors, neurotransmitters and their receptors); oncogenes (e.g., ABLI, BCLI, BCL2, BCL6, CBFA2, CBL, CSFIR, ERBA, ERBB, EBRB2, ETSI, ETS1, ETV6, FGR, FOS, FYN, HCR, HRAS, JUN, KRAS, LCK, LYN, MDM2, MLL, MYB, MYC, MYCLI, MYCN, NRAS, PIM 1, PML, RET, SRC, TALI, TCL3, and YES); tumor suppressor genes (e.g., APC, BRCA1, BRCA2, MADH4, MCC, NF1, NF2, RB1, p53, BIM, PUMA and WTI); and enzymes (e.g., ACC synthases and oxidases, ACP desaturases and hydroxylases, ADP-glucose pyrophorylases, ATPases, alcohol dehydrogenases, amylases, amyloglucosidases, catalases, cellulases, chalcone synthases, chitinases, cyclooxygenases, decarboxylases, dextrinases, DNA and RNA polymerases, galactosidases, glucanases, glucose oxidases, granule-bound starch synthases, GTPases, helicases, hemicellulases, integrases, inulinases, invertases, isomerases, kinases, lactases, lipases, lipoxygenases, lysozymes, nopaline synthases, octopine synthases, pectinesterases, peroxidases, phosphatases, phospholipases, phosphorylases, phytases, plant growth regulator synthases, polygalacturonases, proteinases and peptidases, pullanases, recombinases, reverse transcriptases, RUBISCOs, topoisomerases, and xylanases).

Promoters/enhancers which may be used to control the expression of a shRNA construct in vivo include, but are not limited to, the PolIII human or murine U6 and H1 systems, the cytomegalovirus (CMV) promoter/enhancer, the human β-actin promoter, the glucocorticoid-inducible promoter present in the mouse mammary tumor virus long terminal repeat (MMTV LTR), the long terminal repeat sequences of Moloney murine leukemia virus (MuLV LTR), the SV40 early or late region promoter, the promoter contained in the 3' long terminal repeat of Rous sarcoma virus (RSV), the herpes simplex virus (HSV) thymidine kinase promoter/enhancer, and the herpes simplex virus LAT promoter. Transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., an immunoglobulin promoter, and from heat-shock promoters, provided such promoters are compatible with the host cell systems. Inducible systems, such as Tet promoters may be employed. In addition, recombinase systems, such as Cre/lox may be used to allow excision of shRNA constructs at desired times. The Cre may be responsive (transcriptionally or post-transcriptionally) to an external signal, such as tamoxifen.

In certain embodiments, a vector system for introducing shRNA constructs into cells are retroviral vector systems, such as lentiviral vector systems. Lentiviral systems permit the delivery and expression of shRNA constructs to both dividing and non-dividing cell populations in vitro and in vivo. Examples of Lentiviral vectors are those based on HIV, FIV and EIAV. See, e.g., Lois, C., et al., Germline transmission and tissue-specific expression of transgenes delivered by lentiviral vectors. Science, 2002. 295(5556): p. 868-72. Most viral systems contain cis-acting elements necessary for packaging, while trans-acting factors are supplied by a separate plasmid that is co-transfected with the vector into a packaging cell line. In certain embodiments, a highly transfectable 293 cell line may be used for packaging vectors, and viruses may be pseudotyped with a VSV-G envelope glycoprotein for enhanced stability and to provide broad host range for infection. In certain aspects, the invention provides novel vectors adapted for use with shRNA expression cassettes. For example, a Gateway recipient sequence may be inserted downstream of the packaging signal to facilitate movement of the shRNA construct to and from different vector backbones by simple recombination. As another example, recombination signals may be inserted to facilitate in vivo transfer of shRNAs from, e.g., a genome-wide shRNA library.

The type of vector and promoters to be employed should be selected, in part, depending on the organism and cell type to be affected. In the case of ex vivo stem cell therapy for human patients, a vector and promoter that are capable of transfection and expression in human cells should be selected.

In certain embodiments, retroviruses from which the retroviral plasmid vectors may be derived include, but are not limited to, Moloney Murine Leukemia Virus, spleen necrosis virus, Rous sarcoma Virus, Harvey Sarcoma Virus, avian leukosis virus, gibbon ape leukemia virus, human immunodeficiency virus, Myeloproliferative Sarcoma Virus, and mammary tumor virus. A retroviral plasmid vector may be employed to transduce packaging cell lines to form producer cell lines. Examples of packaging cells which may be transfected include, but are not limited to, the PE501, PA317, R-2, R-AM, PA12, T19-14.times., VT-19-17-H2, RCRE, RCRIP, GP+E-86, GP+envAml2, and DAN cell lines as described in Miller, Human Gene Therapy 1:5-14 (1990), which is incorporated herein by reference in its entirety. The vector may transduce the packaging cells through any means known in the art. A producer cell line generates infectious retroviral vector particles which include polynucleotide encoding a polypeptide of the present invention. Such retroviral vector particles then may be employed, to transduce eukaryotic cells, either in vitro or in vivo. The transduced eukaryotic cells will express a polypeptide of the present invention.

In certain embodiments, cells are engineered using an adeno-associated virus (AAV). AAVs are naturally occurring defective viruses that require helper viruses to produce infectious particles (Muzyczka, N., Curr. Topics in Microbiol. Immunol. 158:97 (1992)). It is also one of the few viruses that may integrate its DNA into non-dividing cells. Vectors containing as little as 300 base pairs of AAV can be packaged and can integrate, but space for exogenous DNA is limited to about 4.5 kb. Methods for producing and using such AAVs are known in the art. See, for example, U.S. Pat. Nos. 5,139,941, 5,173,414, 5,354,678, 5,436,146, 5,474,935, 5,478,745, and 5,589,377. For example, an AAV vector may include all the sequences necessary for DNA replication, encapsidation, and host-cell integration. The recombinant AAV vector may be transfected into packaging cells which are infected with a helper virus, using any standard technique, including lipofection, electroporation, calcium phosphate precipitation, etc. Appropriate helper viruses include adenoviruses, cytomegaloviruses, vaccinia viruses, or herpes viruses. Once the packaging cells are transfected and infected, they will produce infectious AAV viral particles which contain the polynucleotide construct. These viral particles are then used to transduce eukaryotic cells.

Essentially any method for introducing a nucleic acid construct into cells may be employed. Physical methods of introducing nucleic acids include injection of a solution containing the construct, bombardment by particles covered by the construct, soaking a cell, tissue sample or organism in a solution of the nucleic acid, or electroporation of cell membranes in the presence of the construct. A viral construct packaged into a viral particle may be used to accomplish both efficient introduction of an expression construct into the cell and transcription of the encoded shRNA. Other methods known in the art for introducing nucleic acids to cells may be used, such as lipid-mediated carrier transport, chemical mediated transport, such as calcium phosphate, and the like. Thus the shRNA-encoding nucleic acid construct may be introduced along with components that perform one or more of the following activities: enhance RNA uptake by the cell, promote annealing of the duplex strands, stabilize the annealed strands, or otherwise increase inhibition of the target gene.

Further methods for shRNA and transfecting mice may be found in US Publication No. 2009/0217404.

Approach

Figure 1B:
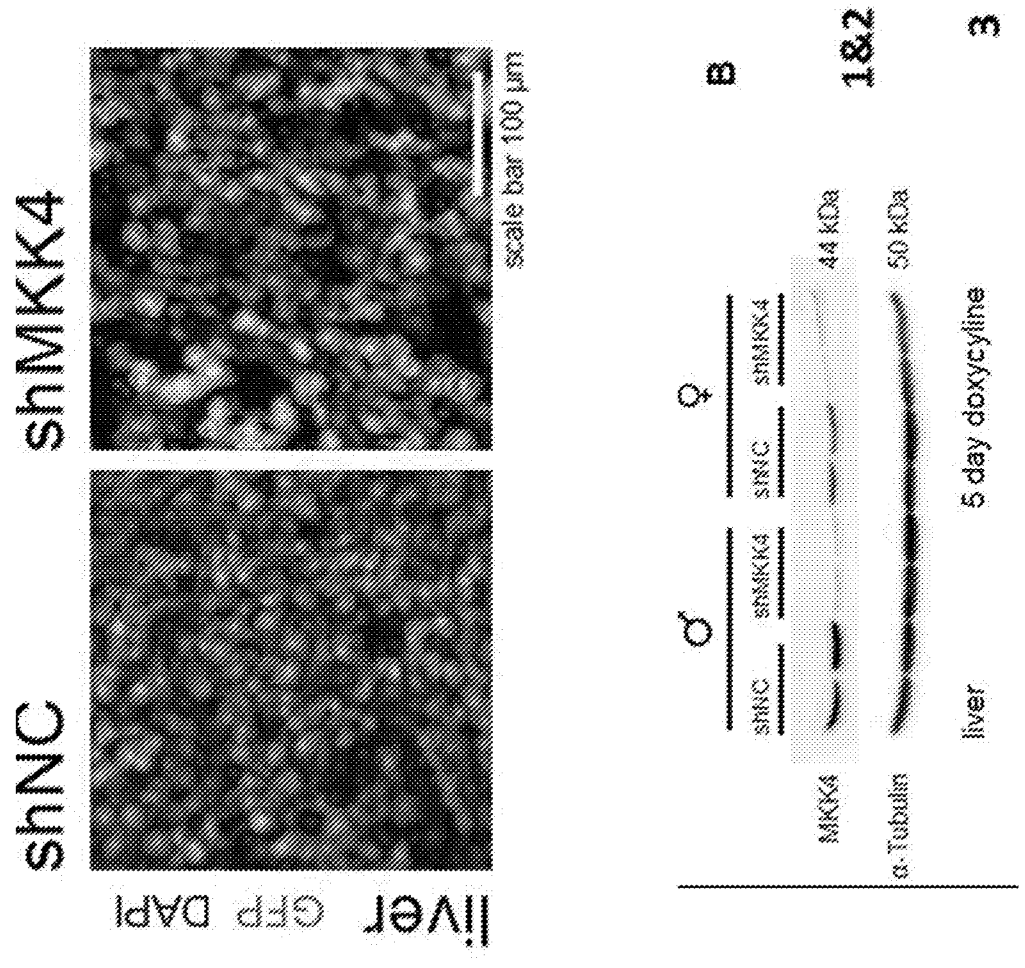
FIG. 1B is a micrograph and protein expression of GFP and Mkk4 expression in isolated hepatocytes.
Figure 1C:
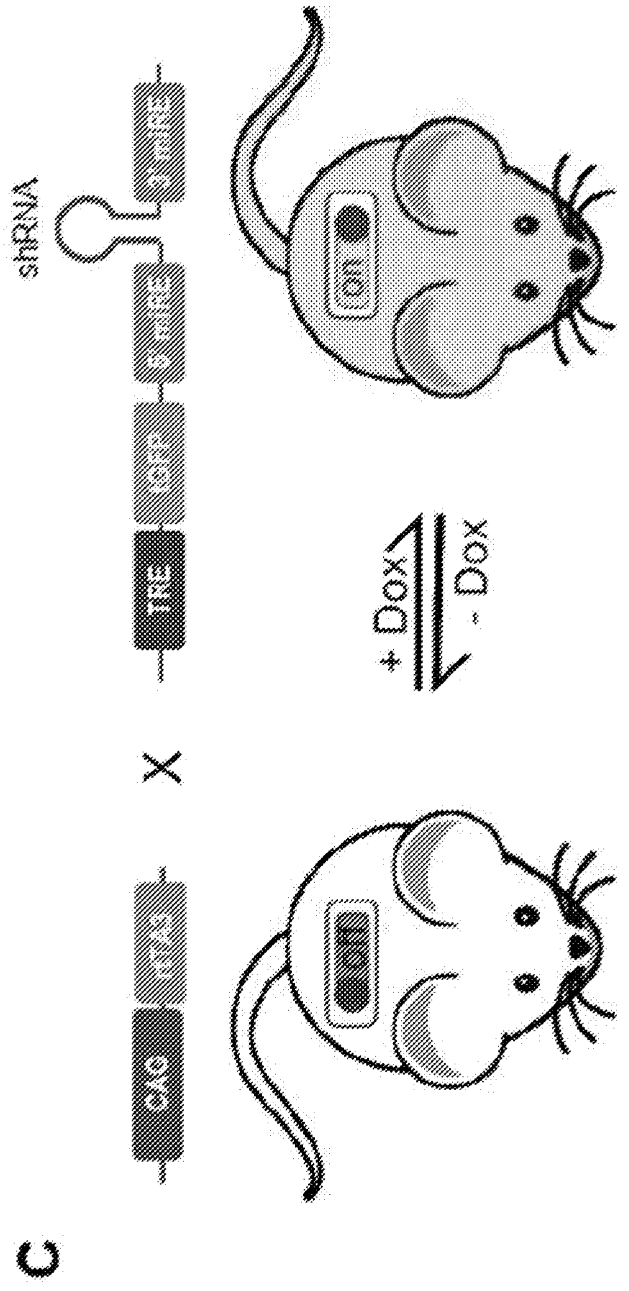
FIG. 1C is a schematic diagram of the transgenic alleles in RNAi mice.

The present inventors have shown that gene suppression by RNAi can mimic loss of gene function in mice' and developed a rapid and efficient approach to introduce doxycycline (dox) responsive, GFP-tagged shRNAs into embryonic stem cells (ESCs) at a defined genomic locus 9-11. Using this system, the present inventors have created more than 200 mouse strains to explore gene function and test the therapeutic potential of systemic gene silencing in vivo (FIGS. 1A-1C). For example, the present inventors have shown that transgenic shRNAs targeting several tumor suppressor genes including Trp53, INK4a/ARF, APC and PTEN not only recapitulate the phenotypes of corresponding knockout animals, but also provide a means to assess the consequences of gene restoration on disease progression[10-12]. The present inventors also demonstrated that RNAi-mediated silencing of Myc[13], Cdk9[14], Rpa3[15], Brd4[16], Ptgs2[17], elF4F[18], NuakI (in press), and others in mice enabled the evaluation of novel candidate therapeutic targets.

Figure 3:
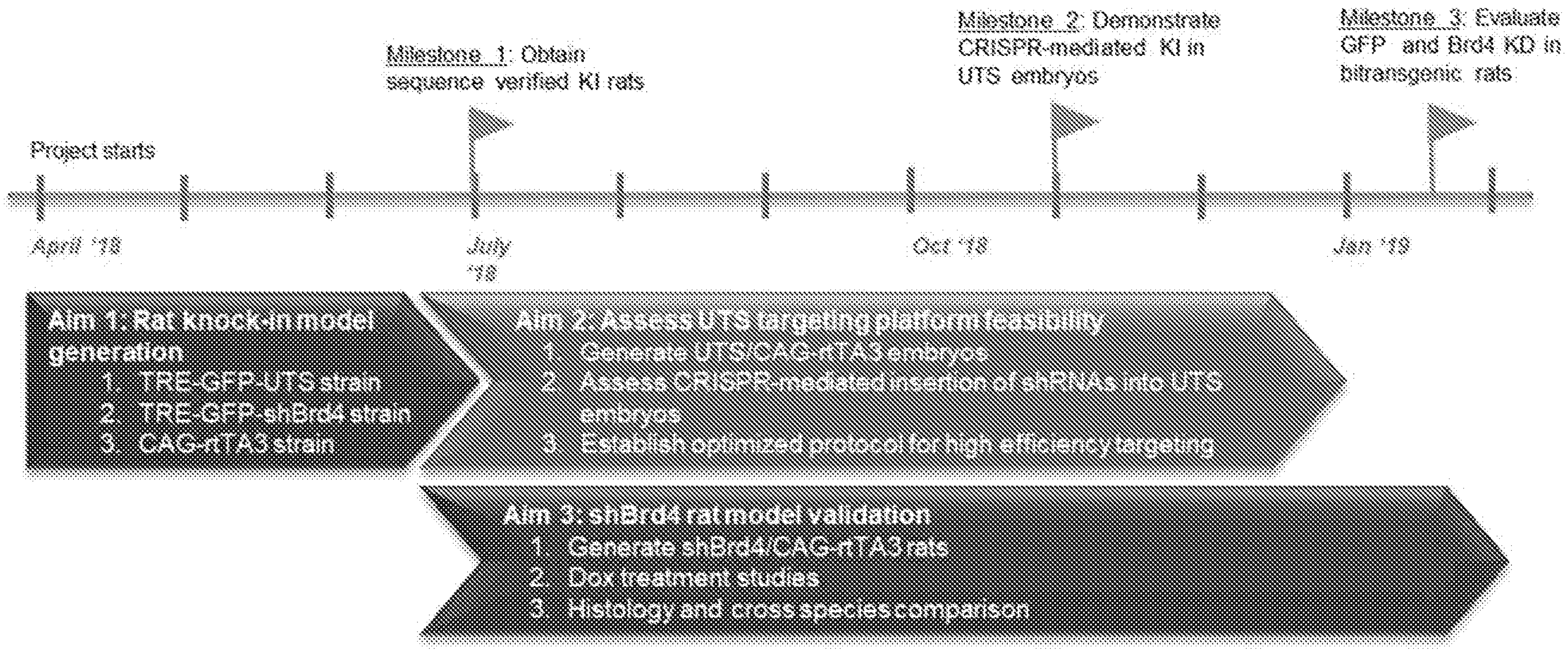
FIG. 3 is a diagram of alternative embodiments of the invention.

The present invention comprises a platform for streamlined production of transgenic RNAi rat models and showcases their reversible gene silencing capabilities (FIG. 3). In a first embodiment, the present invention uses CRISPR/Cas9 to establish key components of the system in rats (FIG. 2B). The present invention comprises new rat strains that will serve as the foundation for future high-efficiency editing to transfer RNAi technology to the rat model. In a second embodiment, the present invention further comprises integrating small inducible shRNAs into pre-engineered embryos and determining the best practices for efficiency and scalability. In a third embodiment, the present invention comprises using an RNAi platform with a rat harboring an shRNA targeting Brd4 and mimic drug intervention using RNAi-mediated gene silencing in rats. Validation studies on Brd4 are performed in order to compare our results to our Brd4 RNAi mice and identify potential organism variances, as well as generate valuable data that may inform early clinical trial studies that have already been initiated using BET inhibitors'". The present invention provides RNAi-mediated gene suppression in rats and also develops a platform for large scale production of RNAi rats and other species in the future.

Establish Founder Knock-In Rats Using CRISPR/Cas9

In the first embodiment, the present invention comprises using CRISPR/Cas9 genome editing, including generating at least three rat strains harboring: (1) a 2.5 kb "homing cassette" that contains a TRE promoter, GFP reporter and a Unique Target Site (TRE-GFP-UTS or UTS) for rapid and efficient insertion of shRNAs in subsequent rat generations (FIG. 2A); (2) a tet-inducible GFP-coupled shRNA targeting the rat Brd4 gene (TRE-GFP-shBrd4) and (3) a CAG-rtTA3 tet-transactivator cassette for dox-inducible expression (FIG. 2B). CRISPR systems knock-in foreign DNA elements to a precise genomic location using homology directed repair (HDR) 39-41 more efficiently than traditional homologous recombination; however, the efficiency rate of HDR decreases as the size of the insertion increases. In mice, a success rate of –30-50% when using insertions <1.5 kb has been achieved; however this rate decreases substantially to <10% when using templates >2 kb. Therefore, although the present inventors have successfully generated mice with insertions up to 10 kb using direct injection methods, it would be commercially unfeasible to routinely insert the entire TRE- GFP-shRNA cassette to generate each new RNAi rat model. To facilitate high efficiency rates, the present invention comprises inserting a 2.5 kb insert containing common elements used in each RNAi model (i.e. TRE-GFP-miRE) plus a unique gRNA target sequence (UTS) that will serve as a common "landing pad" for the subsequent introduction of specific shRNAs (FIG. 2A). The present invention comprises using the region downstream of the Col1a1 gene on chromosome 10 for insertion, as this region has been shown to be a safe harbor for widespread transgene expression in the mice. In parallel, the present invention comprises generating a model containing the entire TRE-GFP-shBrd4 cassette to obtain a rat that can be used immediately for validation while simultaneously establishing the high efficiency targeting platform. Lastly, the present invention comprises generating a CAG-rtTA3 rat strain by insertion at the Rosa26 locus. The present invention comprises generating each rat strain by direct injections of CRISPR reagents (Cas9 protein+gRNA+donor template) into Sprague Dawley (SD) embryos. At least 2 founders from each strain will be subjected to whole genome sequencing alongside of SD control animals to identify any off-target effects. In one embodiment, the SD strain is chosen however other strains may be selected. In other embodiments, an in-bred strain may be engineered as well. Other strains include, but are not limited to the following: Brown Norway rat, Buffalo rat, Copenhagen Rat, Dahl/Salt sensitive rat, F344 Rat, FHH rat, Fischer Rat, Goto-Kakizaki rat, Lewis Rat, Lister Hooded Rat, Long-Evans Rat, Obese Prone CD Rat, Obese Resistant CD rat, OFA Rat, SHR Rat, SHHF Rat, Wistar Rats, ZDF Rat, Zucker Rat.

In one embodiment, the UTS sequences may be selected from the following in Table 1:

TABLE 1

| | Rat CTE UTS |
|---|---|
| Target Sequence | GCTTCGTGTAAACTCCCTCCATCCCAATCTGGTTCCC |
| SEQ ID NO: 1 | TCCCACCCAGCCCACTTTCCCCCAACCCTGGAAACA |
| Legend: | GACCAACAACCCAAACTCAATTTCCCCAAAAGCCAA |
| Rat Col1a1-201 Exon 51 | AAATTGGGAGACAATTTCACATGGACTTTGGAAAAC |
| | ATTTTTTTCCTTTGCATTCATCTCTCAAACTTAGTTTT |
| | TATCTTTGACCAACTGAACGTGACCAAAAACCAAAA |
| | GTGCATTCAACCTTACCAAAAAGAAAAAAAAATAA |
| | GAATAAATAAATAACTTTTTAAAAAAGGAAGCTTGG |
| | TCCTCTTGCTTGAAGACCTATGTGGGTATAAGTCCCT |
| | TTCTGCCCACTGGGCTTATGATACCCCAAATGCTGCC |
| | TTTTCTGTTCCTTTCTCCACCCCCTCTTGGGGCCTCTC |
| | CTCCATTGCTCCCCAAATTTAAGTCTCCCCCAAAGAC |
| | ACAGGAAATAATGCATTGTCTGCCCAGCCAGCAAAG |
| | GCAATGCTGAATCGTCCCACCAGCCCCTCAACCCCC |
| | AGCCTACTTCCCTACCCAGCACCTTCAAATCCTGCCG |
| | GGACATGGGGTTCTCGGACTATTGAAGGAGCCTAAC |
| | CATCTGGCATCTCCATGGCCTCTGCAACAAATCCCC |
| | ACACACACTTTGTTTTTGAGGGCCTGTGCTGGGGGA |

TABLE 1-continued

| Rat CTE UTS |
|---|
| GCCACCTGCCCCTCGCAGGGGTTTGGAGCCAGGCAG |
| GGTCACAGCAGACTGGAAACATCGGCCACACATGTG |
| CAGGCTGGGTGGGAGAGACTGTTCTGTTCCTTGTGT |
| AATTGTGTTGCTGAAAGACTACCTCGTTCTTGTCTTT |
| GTGTGTCACCGGGGCAACTGTGTGGGGGCGGGGATG |
| GGGGCAGGGTGGCAGCGCGCCCAGTTTGGTATCAAA |
| GGTGCTACATCTCTGTGAAGGGGTGGGGTGGGAAGG |
| AATTTCTGGTGCTATAGAATCTGAGATGCTCCCCTAG |
| ACCAGCAAATGTTCCTTTTGTTCAAAGTATTTTTTTA |
| TTCTTTTTTTTTTTAATGGATAGGGACTTGTGTGAATT |
| TTCTTTTCCTGACGGTGCTATTTAACAAGGGAGGAG |
| AGAGTGCCAACTCCAGCCTGCTCTCTCTCTACCCCCC |
| TCTTCACTCTTCCAGCTCCTGGGCCTATCTGATGATC |
| TCTCTCTCTTCTGAAACCCTCCCCTCTTGCTGCTGCTC |
| CCTACCCTCAGCTTCTCTCTCTCTCTGTCCTGCATCA |
| GGGTTTCAGAGCACCATTTTCCAAAGCACAAAGCAG |
| TTTTTATCCCTGGGGTGGGAGGAAGCAAGAGACTCT |
| GTACCTATTTTGTATGTGTATAATAATTTGAGATGTT |
| TTTAATTATTTTGATTGCTGGAATAAAGCATGTGGAA |
| ATGACCCAACGCATGTTCAGTGGTCTCTGAATTTCCT |
| TCCTGGAACTTGGGGAGGTGGGGATCCAGGGAGAG |
| GCTTTGGGATGTGTGAGGCAGGGAGCTTGTCTTCTA |
| CCATCACCCTTTATCTCTCCCCCCACTTCTCATCCAG |
| ATGCCGTTGCCTTCCTCTTGCCTTTCTTACGCCTTAG |
| ACCCATTTTTCTTGCCTCTTTTACCTTTTCCCCTTTCA |
| AGTCCTCTTTGCACATCCCCAAGTCCCCCAAGTCTCC |
| ACCACAGTT**CAATACCAGACGCACAGCAT**CACGGG |
| CAAACTCGCACGCACTTCAAATCCCGGACCACCCAT |
| ACCTCAGGCCAGAATCCTAATGGTGTATCACTCTTCC |
| ATGATGTAGACCTGAGGCCTGGCGAGGTGTTGCCTA |
| TGGGTCCTGAGAGGCTCAGGGACTCTCAAAAGGATC |
| CAGAGGGAGGGAACAGGGACTGAGTCATGGAGGAC |
| CAGGTTTCTCCCTGGTCAAGCATGGAGGGGTAGTTG |
| GCTTCTCCCCATCTCTTGCCCAAAGAAACAAGTGATT |
| TGATATAGAAGGGGCCTTTTGAGGCTGGAGTGCCAC |
| CAGGAGGGTAAGAATGTTCTGAGGTCACTCTTGCTC |
| TCACCAGAGGGAGGTGCCCAGCTCCCAAAGGGATCT |
| CCTGGGGGCTCTTAGAGAGCTGTGGTGAAGGAACTT |
| CCAGTGTGTCAC**CAGAAAGGACAGGACCCCAC**ACC |
| ACAGAGGTGCGTGGGTCACTCCTGGTCTTCGGCGTG |
| CCCAGAGAGCGTGCTGGCTCGGTGCAGGGGGCCTGT |
| GGAATCATGCCACCCTTCCTCCTGCCTCTTCTTCCCT |
| TTGCCTTTATCTCTACAACTTTTTGCTTCTTTTTCCTC |
| CTTTTCCCCCCTCCCTCCTTCCCTCCCTTCCTCTGCCG |
| GTCTGAGAATCTGAGGCCCTAGGAGAGTGGTAACTG |
| ACTGTCCCCCACATCTCAGAGAATGGGGACATAGTG |
| GAAGGTCTGAGAATCCAGCAGGCAGGAGTCTGCACT |
| GAACCGGACACTAAACATAAGGACACAGGTGACCC |
| CATTCAGGGGGTCAGGTCTCAAATTTGAAAGGAAGG |
| CACAGACTACTTGTAGCTTCCCTTTCTTGTGCTACCA |
| GAGAGACCAACTAATCTACTGCAGTGTCCACTGGAC |
| ACGATCTTACTGCCACTGAGTACTCGAGACTGTTAA |
| TTATGACCTTTAATAATTTATTACTAGCACTTTACAT |
| GAGGGCAATGTAAAAAGAAAATTTATCTAGAGAGG |
| AAAAGAAGTTGAGGAGTATAAATGAAGATCTATTTA |
| GACACAAATTACCCAAAATTGCGTGGTCCTGATAGA |
| CCCATTGATTGATGCAGTGATTGGGTGATACCTTTCT |
| CCCCAGGCATCCCCAGTCTTGAGGCTCTTCCTGGCTT |
| AGACCCTATCTCTTCCCATCCTCACAGGGTCCATCCT |
| TCTGAACTCAGCATCTGAGCTGTACCTGGCCACTACT |
| CACTTGTCTAAGCTTATTGTCTCCTCCAGGGCCTACA |
| TCTGTCATCTCAGTCAATAGGCATGATTACAATTTAT |
| ATATATAATATATATACACATATATTATATATAATAT |
| AAATTCACATACACACACACACACACACACACACAC |
| ACACACACACACACACACACACACAAGCCCAAGCT |
| GACCTCAGCCCTCTGAGGTCCCAACACACTGCTAGC |
| CCCTTACCCAGACGTTACAGGCCCCTGTGGTCATGG |
| TCCACCATGTTCTTTCTAGTGTCAAGGCCTGGAAATT |
| CTGTGCAGGGCTGGGCACAGTCTTCATAGGTACTAG |
| GGAGAGACAAGATGGTGATAGAGGTCCTCTGGAGG |
| ATGTGAGTACAGAGTACAGAGCTGTGGAAAGGTGA |
| AGGTGAAGGTGAGAGGAAGGAGAACAAACGACAGT |
| TTCCTGACGTGACAGGTAGTTGAGCCCTTAAAATGT |
| GGCTCCGTGATAAAGGACTGCAATCCTCACTTTTACT |
| ACTGCAATCACTTTCACTAACTGCAAAAGGGCTGAA |
| GGAAGCAAGCTCCAGGCAAAGGAGCGAAGAGCGCC |
| TCTCACTGTGCATATGCAAATCTACACGGGCGTCTG |
| CATGCACACGCATGTTCACATGTGGATATATGCATG |

TABLE 1-continued

| Rat CTE UTS | |
|---|---|
| | AGCATGTGCGTCTTGTGGTAGGCCTTGTGTGCAGCA<br>CTCCTCGGCGGCCATCACATGGTGAGGGCTGGTATG<br>TGCTCTAAGTGTGTGTACAGAGCAGCAGGGAAGGGG<br>GACAACAAAGAGAGCATTGTATCACACTCTGAACCC<br>AAGCCCTCCTTTCCGCTGACATCATTGCCGCCTTAAA<br>TACAGATGCCAGGCCCTGTTCCCAAGACCCTCACTG<br>TCCCCTGTGTGCTAACACAGCTCTGCTGTGTGGACTT<br>CCCGTTCATCTTTATGGGGAAGACTATCCTCCTGGAG<br>CCGATGTTTCCATCAAATCCAAGTAGAAAAAATCTA<br>CAGGGAAAGAAGGTTTGGTTTTGATTTTTTACTCTTG |
| gpRat Col1a1 F1<br>SEQ ID NO: 2 | 5' **CAATACCAGACGCACAGCAT** 3' |
| gpRat Col1a1 R1<br>SEQ ID NO: 3 | 5' **GTGGGGTCCTGTCCTTTCTG** 3' |
| gRNA guide sequence<br>SEQ ID NO: 4 | AGGCTGGAGTGCCACCAGGAGGG |
| Donor sequence<br>SEQ ID NO: 5<br>Legend:<br>Rat Col1a1-201 Exon 51<br>TRE promoter<br>EGFP<br>miRE recipient sequence<br>RGB pA | GCTTCGTGTAAACTCCCTCCATCCCAATCTGGTTCCC<br>TCCCACCCAGCCCACTTTCCCCCAACCCTGGAAACA<br>GACCAACAACCCAAACTCAATTTCCCCAAAAGCCAA<br>AAATTGGGAGACAATTTCACATGGACTTTGGAAAAC<br>ATTTTTTTCCTTTGCATTCATCTCTCAAACTTAGTTTT<br>TATCTTTGACCAACTGAACGTGACCAAAAACCAAAA<br>GTGCATTCAACCTTACCAAAAAGAAAAAAAAATAA<br>GAATAAATAAATAACTTTTTAAAAAAGGAAGCTTGG<br>TCCTCTTGCTTGAAGACCTATGTGGGTATAAGTCCCT<br>TTCTGCCCACTGGGCTTATGATACCCCAAATGCTGCC<br>TTTTCTGTTCCTTTCTCCACCCCCTCTTGGGGCCTCTC<br>CTCCATTGCTCCCCAAATTTAAGTCTCCCCCAAAGAC<br>ACAGGAAATAATGCATTGTCTGCCCAGCCAGCAAAG<br>GCAATGCTGAATCGTCCCACCAGCCCCTCAACCCCC<br>AGCCTACTTCCCTACCCAGCACCTTCAAATCCTGCCG<br>GGACATGGGGTTCTCGGACTATTGAAGGAGCCTAAC<br>CATCTGGCATCTCCATGGCCTCTGCAACAAATCCCC<br>ACACACACTTTGTTTTTGAGGGCCTGTGCTGGGGGA<br>GCCACCTGCCCCTCGCAGGGGTTTGGAGCCAGGCAG<br>GGTCACAGCAGACTGGAAACATCGGCCACACATGTG<br>CAGGCTGGGTGGGAGAGACTGTTCTGTTCCTTGTGT<br>AATTGTGTTGCTGAAAGACTACCTCGTTCTTGTCTTT<br>GTGTGTCACCGGGGCAACTGTGTGGGGGCGGGGATG<br>GGGGCAGGGTGGCAGCGCGCCCAGTTTGGTATCAAA<br>GGTGCTACATCTCTGTGAAGGGGTGGGGTGGGAAGG<br>AATTTCTGGTGCTATAGAATCTGAGATGCTCCCCTAG<br>ACCAGCAAATGTTCCTTTTGTTCAAAGTATTTTTTTA<br>TTCTTTTTTTTTTAATGGATAGGGACTTGTGTGAATT<br>TTCTTTTCCTGACGGTGCTATTTAACAAGGGAGGAG<br>AGAGTGCCAACTCCAGCCTGCTCTCTCTCTACCCCCC<br>TCTTCACTCTTCCAGCTCCTGGGCCTATCTGATGATC<br>TCTCTCTCTTCTGAAACCCTCCCCTCTTGCTGCTGCTC<br>CCTACCCTCAGCTTCTCTCTCTCTCTGTCCTGCATCA<br>GGGTTTCAGAGCACCATTTTCCAAAGCACAAAGCAG<br>TTTTTATCCCTGGGGTGGGAGGAAGCAAGAGACTCT<br>GTACCTATTTTGTATGTGTATAATAATTTGAGATGTT<br>TTTAATTATTTTGATTGCTGGAATAAAGCATGTGGAA<br>ATGACCCAACGCATGTTCAGTGGTCTCTGAATTTCCT<br>TCCTGGAACTTGGGGAGGTGGGGATCCAGGGAGAG<br>GCTTTGGGATGTGTGAGGCAGGGAGCTTGTCTTCTA<br>CCATCACCCTTTATCTCTCCCCCCACTTCTCATCCAG<br>ATGCCGTTGCCTTCCTCTTGCCTTTCTTACGCCTTAG<br>ACCCATTTTTCTTGCCTCTTTTACCTTTTCCCCTTTCA<br>AGTCCTCTTTGCACATCCCCAAGTCCCCCAAGTCTCC<br>ACCACAGTT**CAATACCAGACGCACAGCAT**CACGGG<br>CAAACTCGCACGCACTTCAAATCCCGGACCACCCAT<br>ACCTCAGGCCAGAATCCTAATGGTGTATCACTCTTCC<br>ATGATGTAGACCTGAGGCCTGGCGAGGTGTTGCCTA<br>TGGGTCCTGAGAGGCTCAGGGACTCTCAAAAGGATC<br>CAGAGGGAGGGAACAGGGACTGAGTCATGGAGGAC<br>CAGGTTTCTCCCTGGTCAAGCATGGAGGGGTAGTTG<br>GCTTCTCCCCATCTCTTGCCCAAAGAAACAAGTGATT<br>TGATATAGAAGGGGCCTTTTGAGGCTGGAGTGCCAC<br>Cgattgcatatctgggggatcgattctagattcgagtttaccactccctatcagtgataga<br>gaaaagtgaaagtcgagtttaccactccctatcagtgatagagaaaagtgaaagtcga<br>gtttaccactccctatcagtgatagagaaaagtgaaagtcgagtttaccactccctatca<br>gtgatagagaaaagtgaaagtcgagtttaccactccctatcagtgatagagaaaagtga<br>aagtcgagtttaccactccctatcagtgatagagaaaagtgaaagtcgagtttaccactc |

TABLE 1-continued

| Rat CTE UTS |
| --- |
| cctatcagtgatagagaaaagtgaaagtcgagctcggtacccgggtcgaggtaggcg |
| tgtacggtgggaggcctatataagcagagctcgtttagtgaaccgtcagatcgcctgga |
| gacgccatccacgctgttttgacctccatagaagacaccgggaccgatccgtcgagctt |
| gcgttggatccatggtgagcaagggcgaggagctgttcaccggggggtgcccatcc |
| tggtc**GAGCTGGACGGCGACG**taaacggccacaagttcagcgtgtc |
| cggcgagggcgagggcgatgccacctacggcaagctgaccctgaagttcatctgca |
| ccaccggcaagctgcccgtgccctggcccaccctcgtgaccaccctgacctacggcg |
| tgcagtgcttcagccgctaccccgaccacatgaagcagcacgacttcttcaagtccgc |
| catgcccgaaggctacgtccaggagcgcaccatcttcttcaaggacgacggcaacta |
| caagacccgcgccgaggtgaagttcgagggcgacaccctggtgaaccgcatcgagc |
| tgaagggcatcgacttcaaggaggacggcaacatcctggggcacaagctggagtac |
| aactacaacagccacaacgtctatatcatggccgacaagcagaagaacggcatcaag |
| gtgaacttcaagatccgccacaacatcgaggacggcagcgtgcagctcgccgaccac |
| taccagcagaacacccccatcggcgacggccccgtgctgctgcccgacaaccactac |
| ctgagcacccagtccgccctgagcaaagaccccaacgagaagcgcgatcacatggt |
| cctgctggagttcgtgaccgccgccgggatcactctcggcatggacgagctgtacaag |
| taatgaataacagggtaattgtttgaatgaggcttcagtactttacagaatcgttgcctgca |
| catcttggaaacacttgctgggattacttcgacttcttaacccaacagaaggctcgagaa |
| ggtatatt**gctgttgacagtgagcgcctcgg**acttcaaggggctagaatt |
| cgagcaattatcttgtttactaaaactgaataccttgctatctctttgatacatttttacaaag |
| ctgaattaaaatggtataaattaaatcactttttcaattgacgcgttgagaacttcagggtg |
| agtttggggacccttgattgttctttctttttcgctattgtaaaattcatgttatatggag**GG** |
| **GGCAAAGTTTTCAGGGTG**tgtttagaatgggaagatgtcccttgtat |
| caccatggaccctcatgataattttgtttctttcactttctactctgttgacaaccattgtctcc |
| tcttattttcttttcattttctgtaacttttttcgttaaactttagcttgcatttgtaacgaatttttaa |
| attcacttttgtttatttgtcagattgtaagtactttctctaatcacttttttttcaaggcaatcag |
| ggtatattatattgtacttcagcacagttttagagaacaattgttataattaaatgataaggt |
| agaatatttctgcatataaattctggctggcgtggaaatattcttattggtagaaacaacta |
| caccctggtcatcatcctgcctttctctttatggttacaatgatatacactgtttgagatgag |
| gataaaatactctgagtccaaaccgggcccctctgctaaccatgttcatgccttcttctctt |
| tcctacagctcctgggcaacgtgctggttgttgtgctgtctcatcattttggcaaaggattc |
| actcctcaggtgcaggctgcctatcagaaggtggtggctggtgtggccaatgccctgg |
| ctcacaaataccactgagatcgttttccctctgccaaaaattatggggacatcatgaagc |
| cccttgagcatctgacttctggctaataaaggaaatttattttcattgcaatagtgtgttgga |
| atttctcgatcgctagtAcGAccGTAAGAATGTTCTGAGGTCAC |
| TCTTGCTCTCACCAGAGGGAGGTGCCCAGCTCCCAA |
| AGGGATCTCCTGGGGGCTCTTAGAGAGCTGTGGTGA |
| AGGAACTTCCAGTGTGTCAC**CAGAAAGGACAGGAC** |
| **CCCAC**ACCACAGAGGTGCGTGGGTCACTCCTGGTCT |
| TCGGCGTGCCCAGAGAGCGTGCTGGCTCGGTGCAGG |
| GGGCCTGTGGAATCATGCCACCCTTCCTCCTGCCTCT |
| TCTTCCCTTTGCCTTTATCTCTACAACTTTTTGCTTCT |
| TTTTCCTCCTTTTCCCCCCTCCCTCCTTCCCTCCCTTC |
| CTCTGCCGGTCTGAGAATCTGAGGCCCTAGGAGAGT |
| GGTAACTGACTGTCCCCCACATCTCAGAGAATGGGG |
| ACATAGTGGAAGGTCTGAGAATCCAGCAGGCAGGA |
| GTCTGCACTGAACCGGACACTAAACATAAGGACACA |
| GGTGACCCCATTCAGGGGGTCAGGTCTCAAATTTGA |
| AAGGAAGGCACAGACTACTTGTAGCTTCCCTTTCTT |
| GTGCTACCAGAGAGACCAACTAATCTACTGCAGTGT |
| CCACTGGACACGATCTTACTGCCACTGAGTACTCGA |
| GACTGTTAATTATGACCTTTAATAATTTATTACTAGC |
| ACTTTACATGAGGGCAATGTAAAAAGAAAATTTATC |
| TAGAGAGGAAAAGAAGTTGAGGAGTATAAATGAAG |
| ATCTATTTAGACACAAATTACCCAAAATTGCGTGGT |
| CCTGATAGACCCATTGATTGATGCAGTGATTGGGTG |
| ATACCTTTCTCCCCAGGCATCCCCAGTCTTGAGGCTC |
| TTCCTGGCTTAGACCCTATCTCTTCCCATCCTCACAG |
| GGTCCATCCTTCTGAACTCAGCATCTGAGCTGTACCT |
| GGCCACTACTCACTTGTCTAAGCTTATTGTCTCCTCC |
| AGGGCCTACATCTGTCATCTCAGTCAATAGGCATGA |
| TTACAATTTATATATATAATATATATACACATATATT |
| ATATATAATATAAATTCACATACACACACACACACA |
| CACACACACACACACACACACACACACACACACAC |
| AAGCCCAAGCTGACCTCAGCCCTCTGAGGTCCCAAC |
| ACACTGCTAGCCCCTTACCCAGACGTTACAGGCCCC |
| TGTGGTCATGGTCCACCATGTTCTTTCTAGTGTCAAG |
| GCCTGGAAATTCTGTGCAGGGCTGGGCACAGTCTTC |
| ATAGGTACTAGGGAGAGACAAGATGGTGATAGAGG |
| TCCTCTGGAGGATGTGAGTACAGAGTACAGAGCTGT |
| GGAAAGGTGAAGGTGAAGGTGAGAGGAAGGAGAAC |
| AAACGACAGTTTCCTGACGTGACAGGTAGTTGAGCC |
| CTTAAAATGTGGCTCCGTGATAAAGGACTGCAATCC |
| TCACTTTTACTACTGCAATCACTTTCACTAACTGCAA |
| AAGGGCTGAAGGAAGCAAGCTCCAGGCAAAGGAGC |
| GAAGAGCGCCTCTCACTGTGCATATGCAAATCTACA |
| CGGGCGTCTGCATGCACACGCATGTTCACATGTGGA |
| TATATGCATGAGCATGTGCGTCTTGTGGTAGGCCTTG |

TABLE 1-continued

| Rat CTE UTS | |
|---|---|
| | TGTGCAGCACTCCTCGGCGGCCATCACATGGTGAGG GCTGGTATGTGCTCTAAGTGTGTGTACAGAGCAGCA GGGAAGGGGGACAACAAAGAGAGCATTGTATCACA CTCTGAACCCAAGCCCTCCTTTCCGCTGACATCATTG CCGCCTTAAATACAGATGCCAGGCCCTGTTCCCAAG ACCCTCACTGTCCCCTGTGTGCTAACACAGCTCTGCT GTGTGGACTTCCCGTTCATCTTTATGGGGAAGACTAT CCTCCTGGAGCCGATGTTTCCATCAAATCCAAGTAG AAAAAATCTACAGGGAAAGAAGGTTTGGTTTTGATT TTTTACTCTTG |
| gpRat Col1a1 F1<br>SEQ ID NO: 6 | 5' CAATACCAGACGCACAGCAT 3' |
| gp EGFP NR<br>SEQ ID NO: 7 | 5' CGTCGCCGTCCAGCTC 3' |
| gpRGB F1<br>SEQ ID NO: 8 | 5' GGGGCAAAGTTTTCAGGGTG 3' |
| gpRat Col1a1 R1<br>SEQ ID NO: 9 | 5' GTGGGGTCCTGTCCTTTCTG 3' |
| gRNA UTS (unique target sequence) guide<br>SEQ ID NO: 10 | gctgttgacagtgagcgcctcgg |

The first embodiment provides a high-efficiency platform for the second embodiment, and provides a validation of our RNAi platform in the third embodiment. The present invention comprises the generation of three independent rat strains harboring the alleles outlined in FIG. 2B. The present invention comprises whole genome sequencing of the 2-3 founders from each strain to identify potential off-target effects and eliminate founders with undesired mutagenesis.

Dr. Thom Saunders (University of Michigan) has successfully generated >400 knock-in rats using CRISPR/Cas9, as disclosed in Gopalakrishnan K, Kumarasamy S, Abdul-Majeed S, Kalinoski A L, Morgan E E, Gohara A F, Nauli S M, Filipiak W E, Saunders T L, Joe B. Targeted disruption of Adamts16 gene in a rat genetic model of hypertension. Proc Natl Acad Sci USA, 2012 Dec 11; 109(50):20555-20559. (PMID 23185005) PMC 3528556.

Genotyping PCR for 5' ColA1 is shown below as SEQ ID NO: 11:

caataccagacgcacagcat[YY1] cacgggcaaactcgcacgcacttcaaatcccggaccacccatacctcaggccagaa tcctaatggtgtatcactcttccatgatgtagacctgaggcc Tggcgaggtgttgcctatgggtcctgagaggctcagggactctcaaaaggatccagagggagggaacagggactgagtcat ggaggaccaggtttctccctggtcaagcatggaggggtagtt Ggatctccccatctcttgcccaaagaaacaagtgatttgatatagaaggggccttttgaggctuagtgccaccgattgcatat ctgggggatcgattctagattcgagtttaccactccctatca Gtgatagagaaaagtgaaagtcgagtttaccactccctatcagtgatagagaaaagtgaaagtcgagtttaccactccctatcagt gatagagaaaagtgaaagtcgagtttaccactccctatc Agtgatagagaaaagtgaaagtcgagtttaccactccctatcagtgatagagaaaagtgaaagtcgagtttaccactccctatca gtgatagagaaaagtgaaagtcgagtttaccactccctat Cagtgatagagaaaagtgaaagtcgagctcggtacccgggtcgaggtaggcgtgtacggtgggaggcctatataagcagag ctcgtttagtgaaccgtcagatcgcctggagacgccatccacg ctgttttgacctccatagaagacaccgggaccgatccgtcgagcttgcgttggatccatggtgagcaagggcgaggagctgttc accggggtggtgcccatcctggtcgagctggacggcgacg[YY3]

Where [YY1] is Col F1 and [YY3] is EGFP NR. The PCR product size: including WT: No PCR product and the Col1A1 cassette KI is 866 bps.

Genotyping PCR for 3' ColA1 is shown below as SEQ ID NO:12:

ggggcaaagttttcagggtglYY]jttgtttagaatgggaagatgtccatgtatcaccatggaccctcatgataattttgificttt cactttctactctgttgacaaccattgtctcctcttattttctttt Cattttctgtaactifitcgttaaactttagettgcatttgtaacgaatttttaaattcactifigtttatttgtcagattgtaagtactttctcta atcacttttttttcaaggcaatcagggtatattatattgt Acttcagcacagttttagagaacaattgttataattaaatgataaggtagaatatttctgcatataaattctggctggcgtggaaatat tcttattggtagaaacaactacaccctggtcatcatcctg Cctttctctttatggttacaatgatatacactgtttgagatgaggataaaatactctgagtccaaaccgggcccctctgctaaccatgt tcatgccttcttctctttcctacagctcctgggcaacgtgct Ggttgttgtgctgtctcatcattttggcaaaggattcactcctcaggtgcaggctgcctatcagaaggtggtggctggtgtggcca atgccctggctcacaaataccactgagatcgttttccctctgcc Aaaaattatggggacatcatgaagccccttgagcatctgacttctggctaataaaggaaatttattttcattgcaatagtgtgttgga atttctcgatcgctagtacgaccgtaagaatgttctgaggtc actcttgctctcaccagagggaggtgcccagctcccaaagggatctcctgggggctcttagagagctgtggtgaaggaacttcc agtgtgtcaccagaaaggacaggaccccac[YY2]

Where [YY1] is RGB F1 and [YY2] is Col R1. The PCR product size includes WT: No PCR product and Col1A1 cassette KI: 900 bps.

Col1A1 cassette positive animals ID: 274, 278, 283, 284, 285, 291 and 294. The Genotyping PCR products sequence summary is displayed in Table 2.

TABLE 2

Genotyping PCR products sequence summary

| Label Name | Sample Name | Results | Primers Used | Primers Used |
|---|---|---|---|---|
| DC121 | 5' 274 | 5 mixmatch | Forward Rat Col F1 (5' ColAl F) | Reverse EGFP-NR (5' ColAl R) |

TABLE 2-continued

Genotyping PCR products sequence summary

| Label Name | Sample Name | Results | Primers Used | Primers Used |
|---|---|---|---|---|
| DC122 | 5' 278 | 5 mixmatch | Forward Rat Col F1 (5' ColAl F) | Reverse EGFP-NR (5' ColAl R) |
| DC123 | 5' 283 | mixmatch | Forward Rat Col F1 (5' ColAl F) | Reverse EGFP-NR (5' ColAl R) |
| DC124 | 5' 284 | 2 mixmatch | Forward Rat Col F1 (5' ColAl F) | Reverse EGFP-NR (5' ColAl R) |
| DC125 | 5' 285 | 16 mixmatch | Forward Rat Col F1 (5' ColAl F) | Reverse EGFP-NR (5' ColAl R) |
| DC126 | 5' 291 | 15 mixmatch | Forward Rat Col F1 (5' ColAl F) | Reverse EGFP-NR (5' ColAl R) |
| DC127 | 5' 294 | mixmatch | Forward Rat Col F1 (5' ColAl F) | Reverse EGFP-NR (5' ColAl R) |
| DC128 | 5' 736 | mixmatch | Forward Rat Col F1 (5' ColAl F) | Reverse EGFP-NR (5' ColAl R) |
| DC129 | 3' 274 | OK | Forward RGB F1 (3' ColAl F) | Reverse Rat Col R1 (3' ColAl R) |
| DC130 | 3' 278 | OK | Forward RGB F1 (3' ColAl F) | Reverse Rat Col R1 (3' ColAl R) |
| DC131 | 3' 283 | Reverse 2 mixmatch | Forward RGB F1 (3' ColAl F) | Reverse Rat Col R1 (3' ColAl R) |
| DC132 | 3' 284 | 1 mixmatch | Forward RGB F1 (3' ColAl F) | Reverse Rat Col R1 (3' ColAl R) |
| DC133 | 3' 285 | Reverse 1 mixmatch | Forward RGB F1 (3' ColAl F) | Reverse Rat Col R1 (3' ColAl R) |
| DC134 | 3' 291 | OK - 1 mixmatch? | Forward RGB F1 (3' ColAl F) | Reverse Rat Col R1 (3' ColAl R) |
| DC135 | 3' 294 | 2 mixmatch | Forward RGB F1 (3' ColAl F) | Reverse Rat Col R1 (3' ColAl R) |
| DC136 | 3' 736 | OK | Forward RGB F1 (3' ColAl F) | Reverse Rat Col R1 (3' ColAl R) |

Note:
most of mismatches are located in a space region or nonessential region.

Figure 5A:
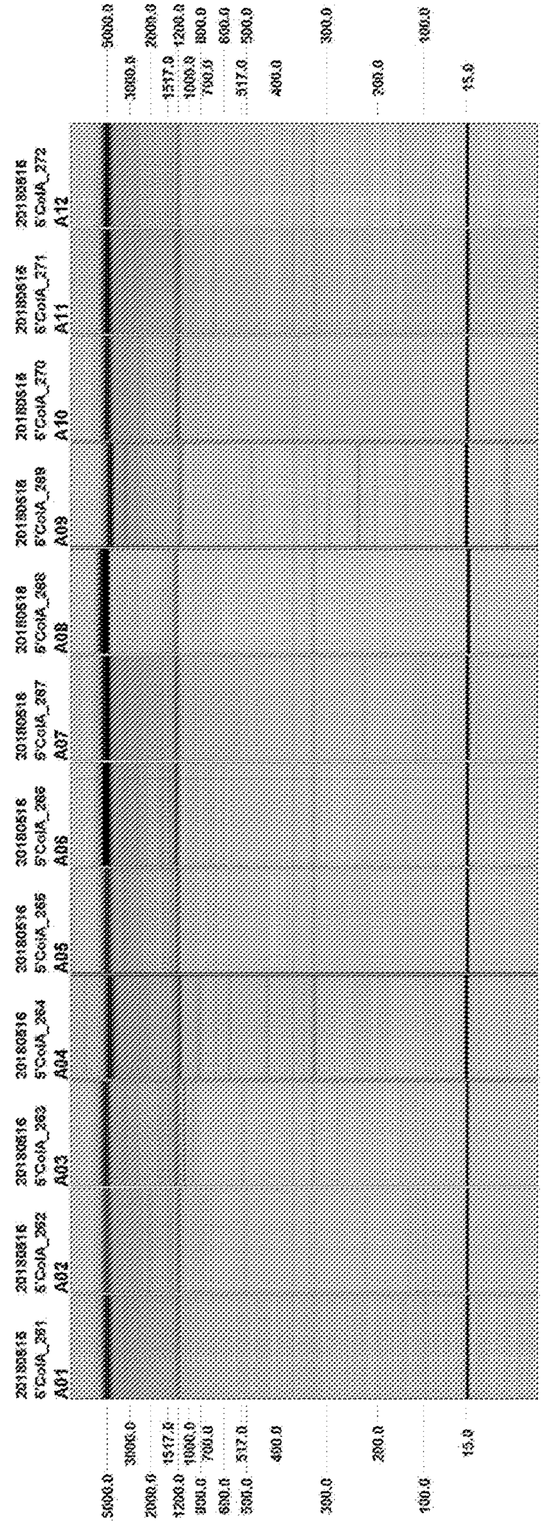
FIGS. 5A-5B are graphs displaying the PCR results for 5' ColA1 #261-284.
Figure 5B:
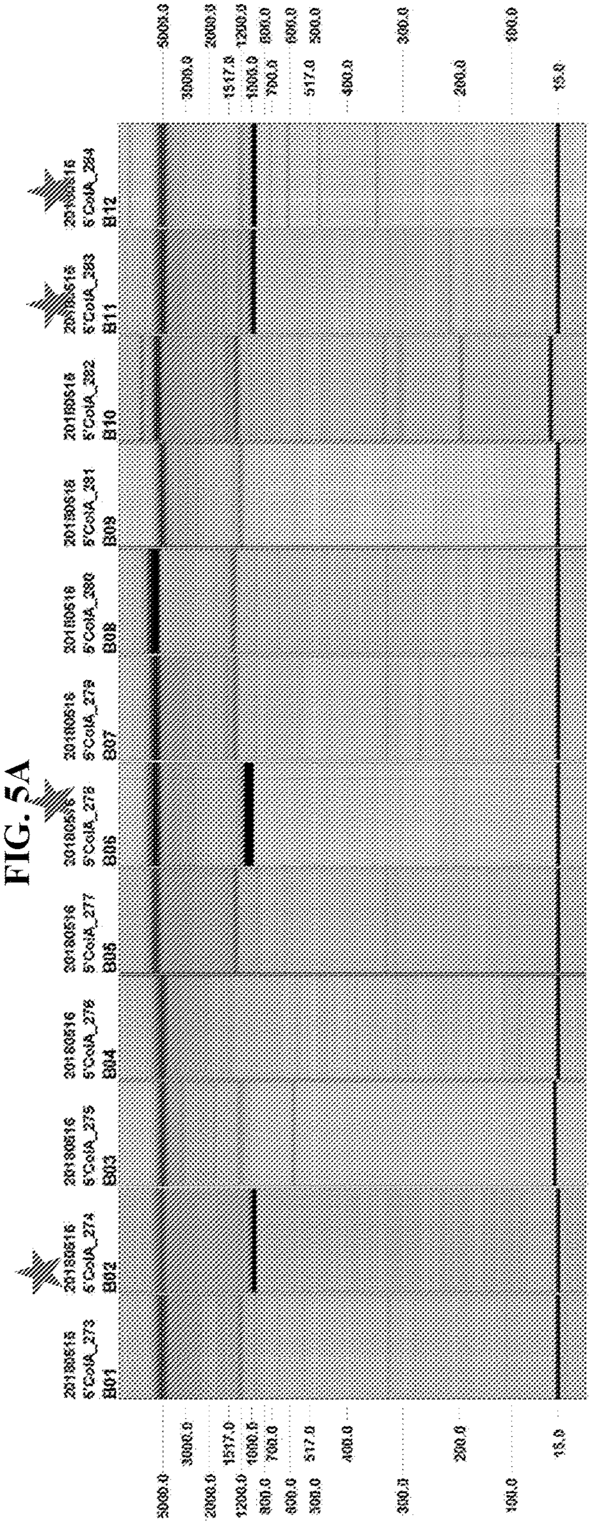
Figure 5C:
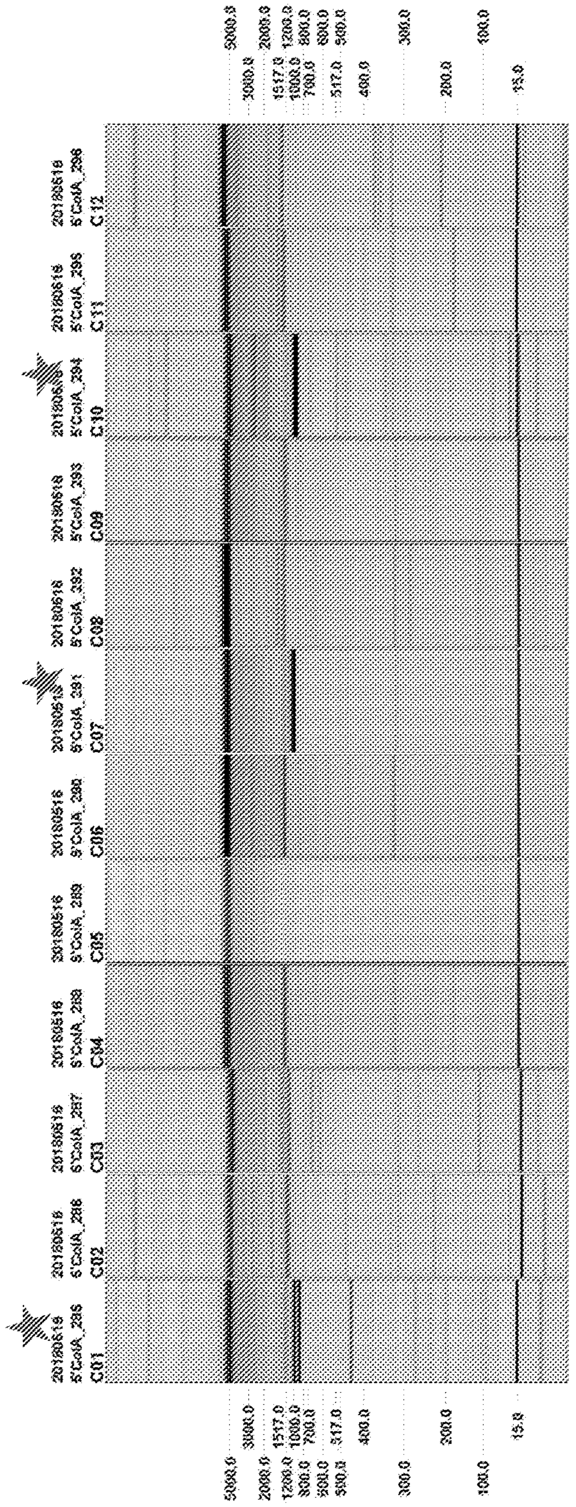
FIGS. 5C-5D is a graph displaying the PCR results for 5' ColA1 #285-300.
Figure 5D:
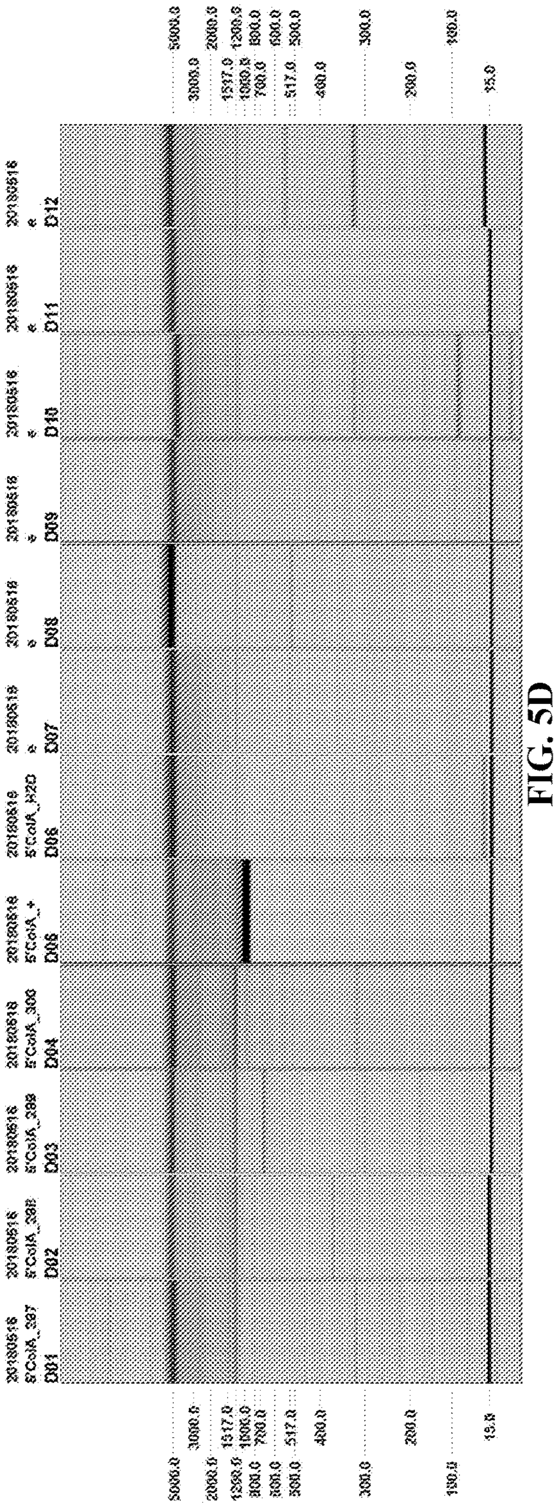

FIGS. 5A-5B displays the PCR results for 5' ColA1 #261-284; FIGS. 5C-5D displays the PCR results for 5' ColA1 #285-300.

Figure 6A:
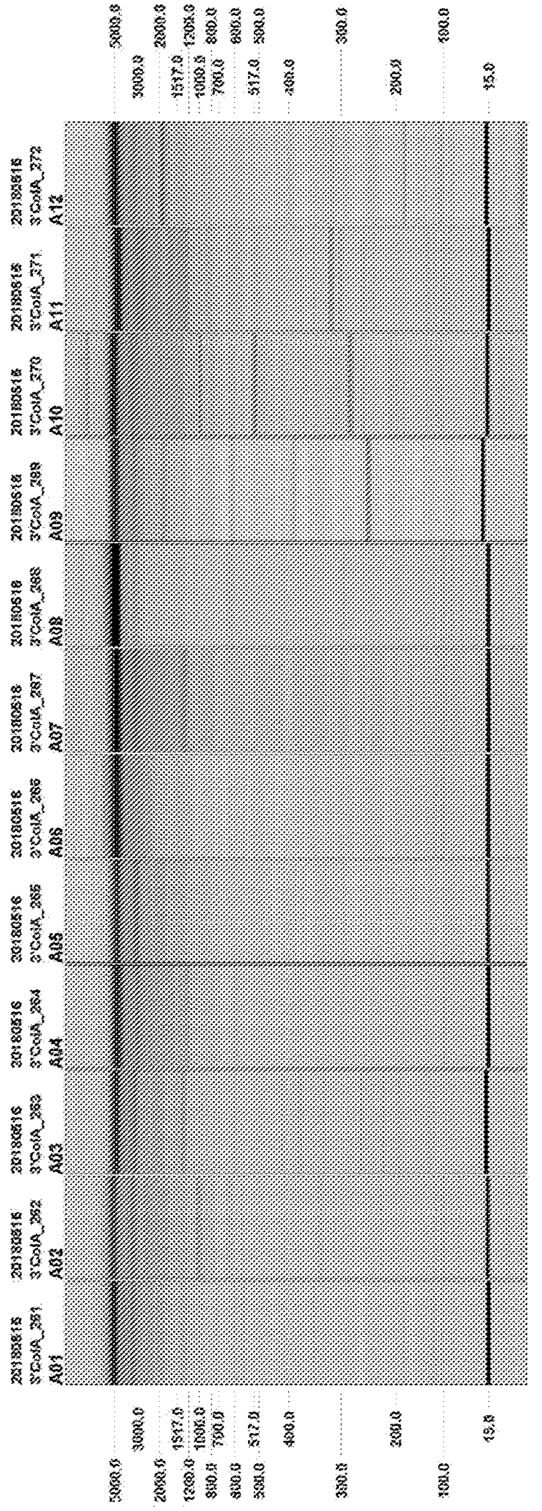
FIGS. 6A-6B are graphs displaying the PCR results for 3' ColA1 #261-284.
Figure 6B:
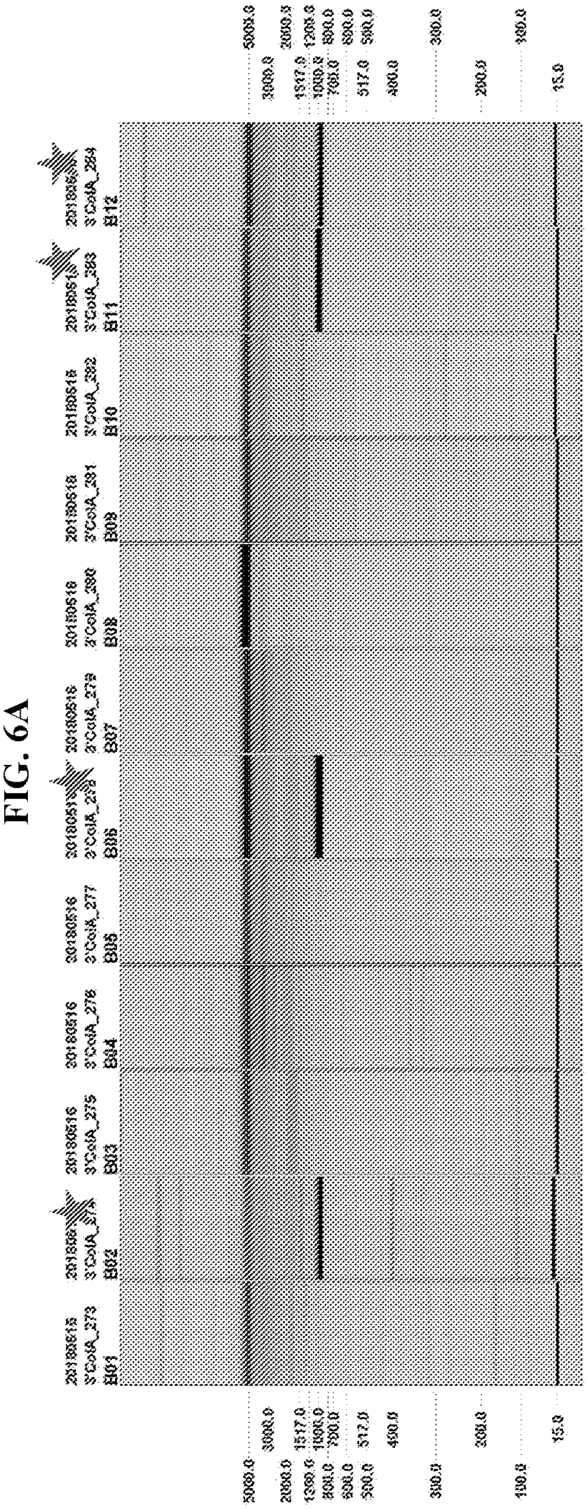
Figure 6C:
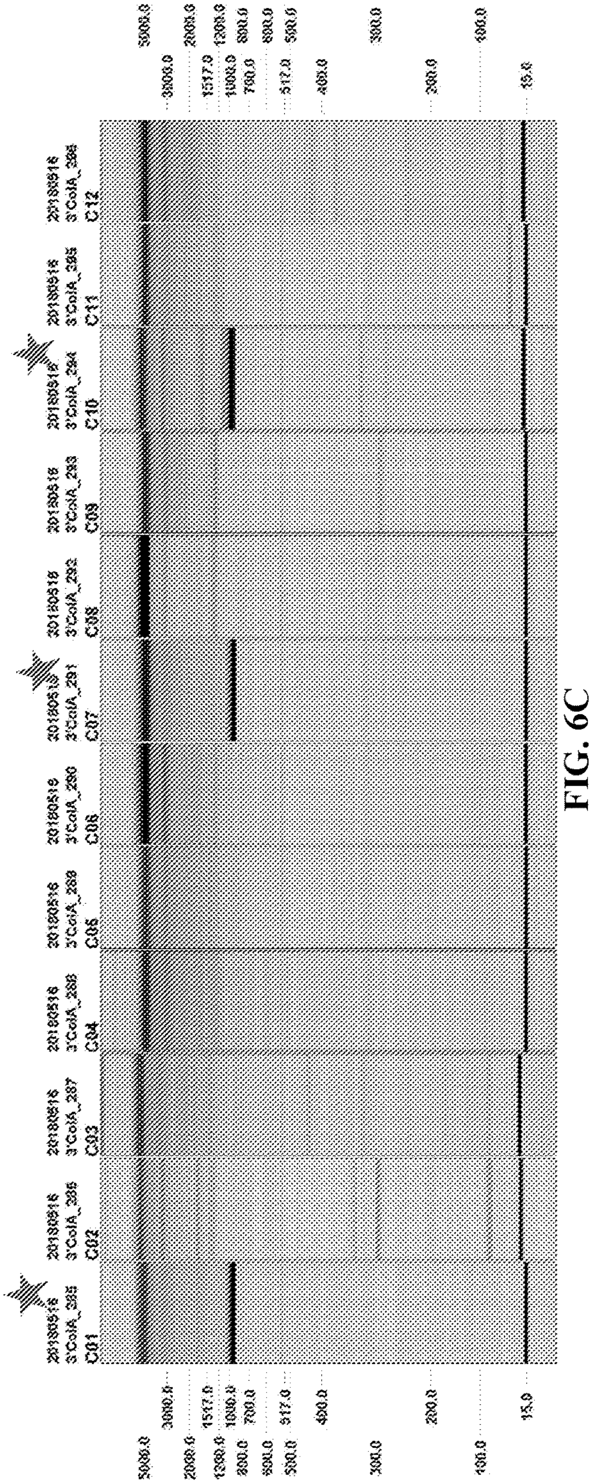
FIGS. 6C-6D are graphs displaying the PCR results for 3' ColA1 #258-300.
Figure 6D:
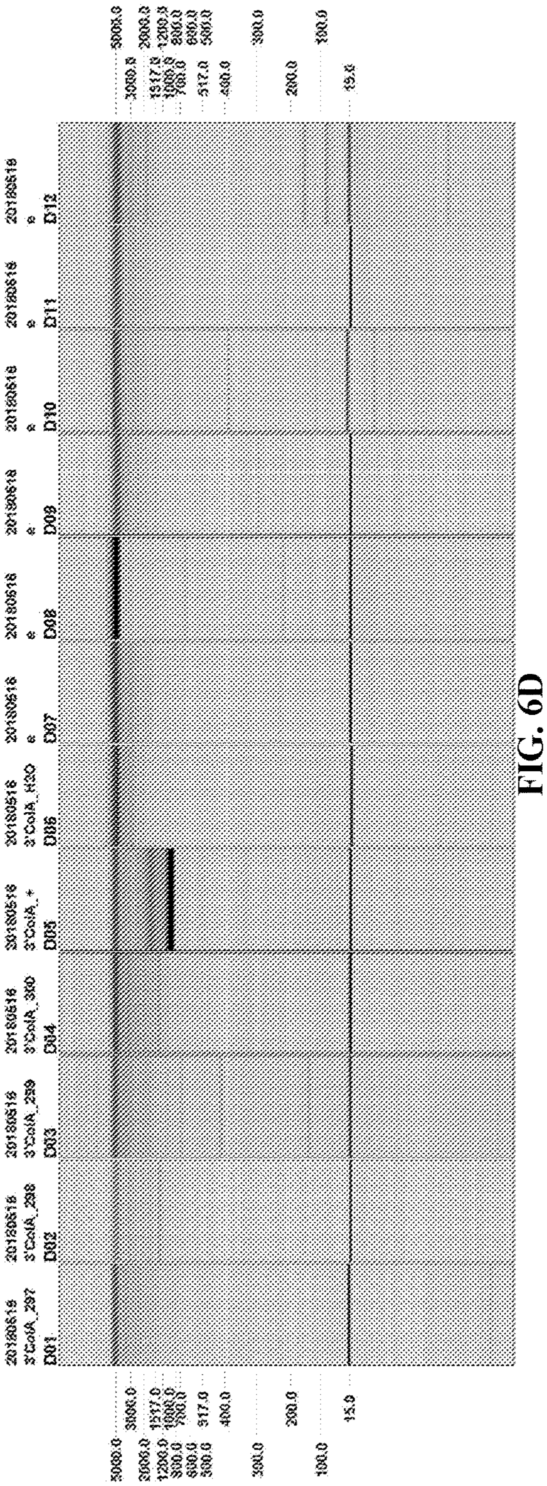

FIGS. 6A-6B displays the PCR results for 3' ColA1 #261-284; FIGS. 6C-6D displays the PCR results for 3' ColA1 #258-300.

Figure 7A:
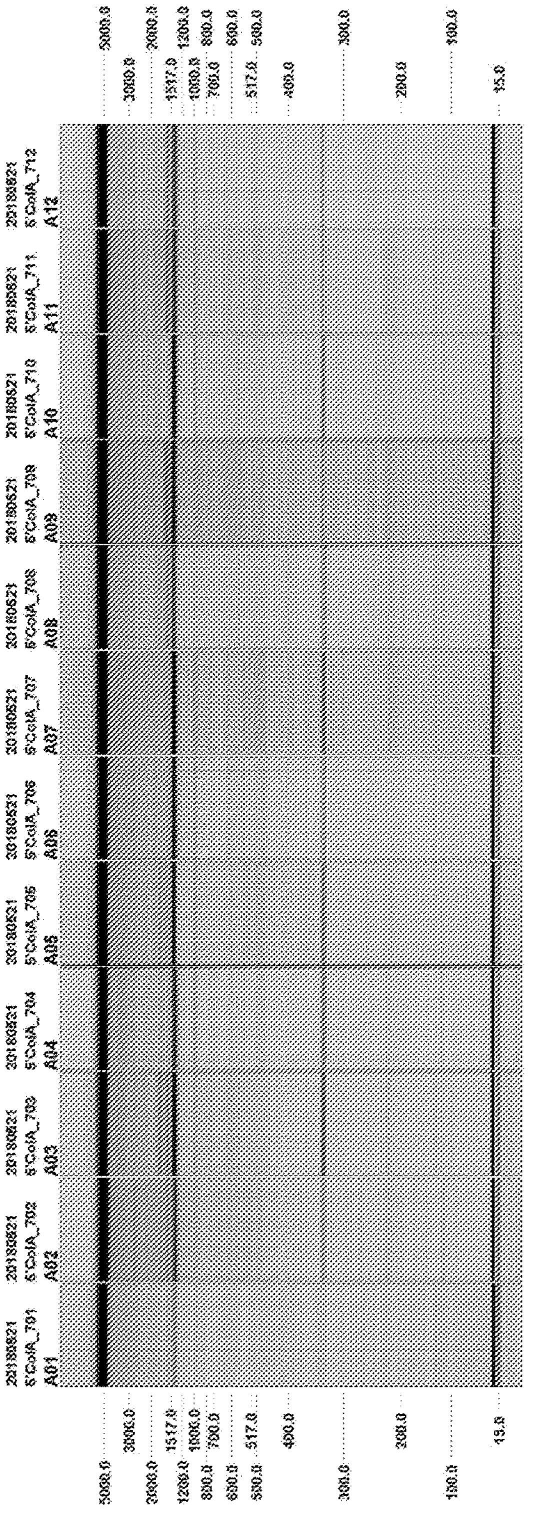
FIGS. 7A-7B are graphs displaying the PCR results for 5' ColA1 #701-724.
Figure 7B:
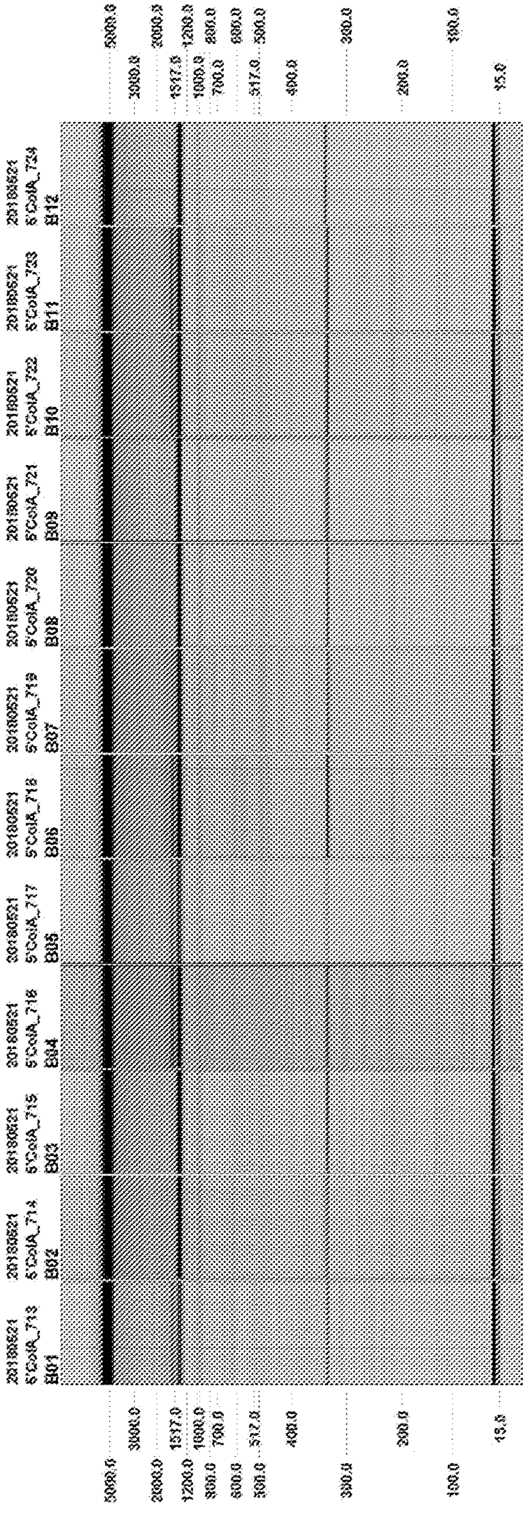
Figure 7C:
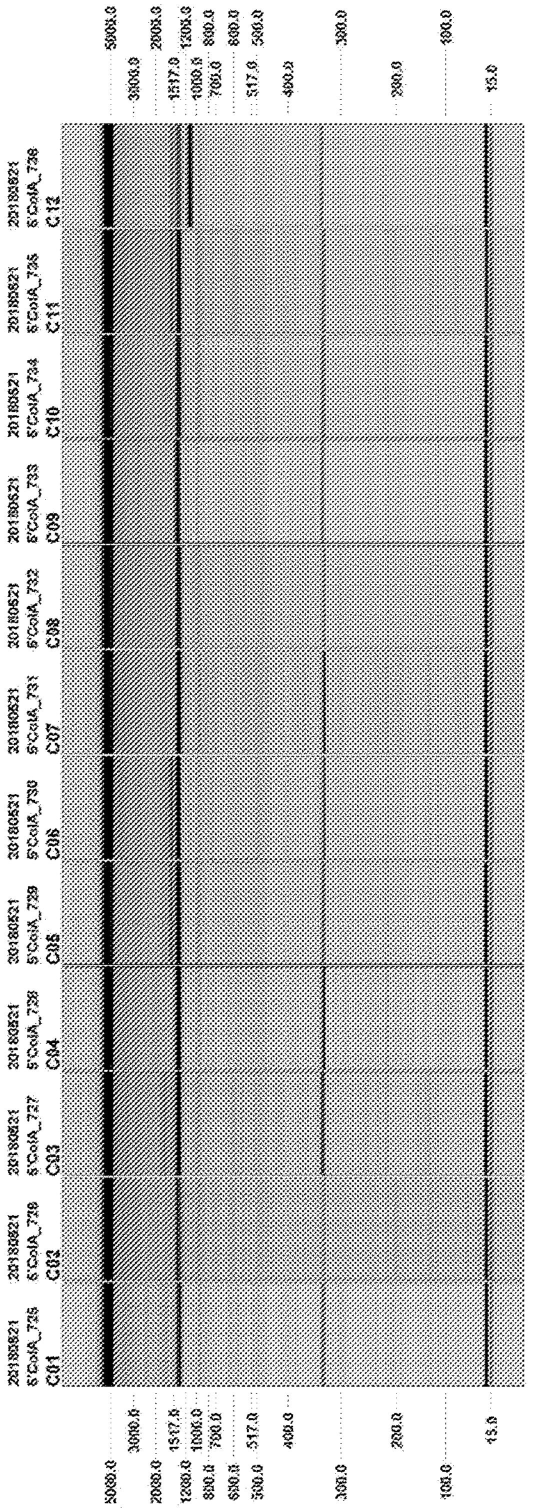
FIGS. 7C-7D are graphs displaying the PCR results for 5' ColA1 #725-748.
Figure 7D:
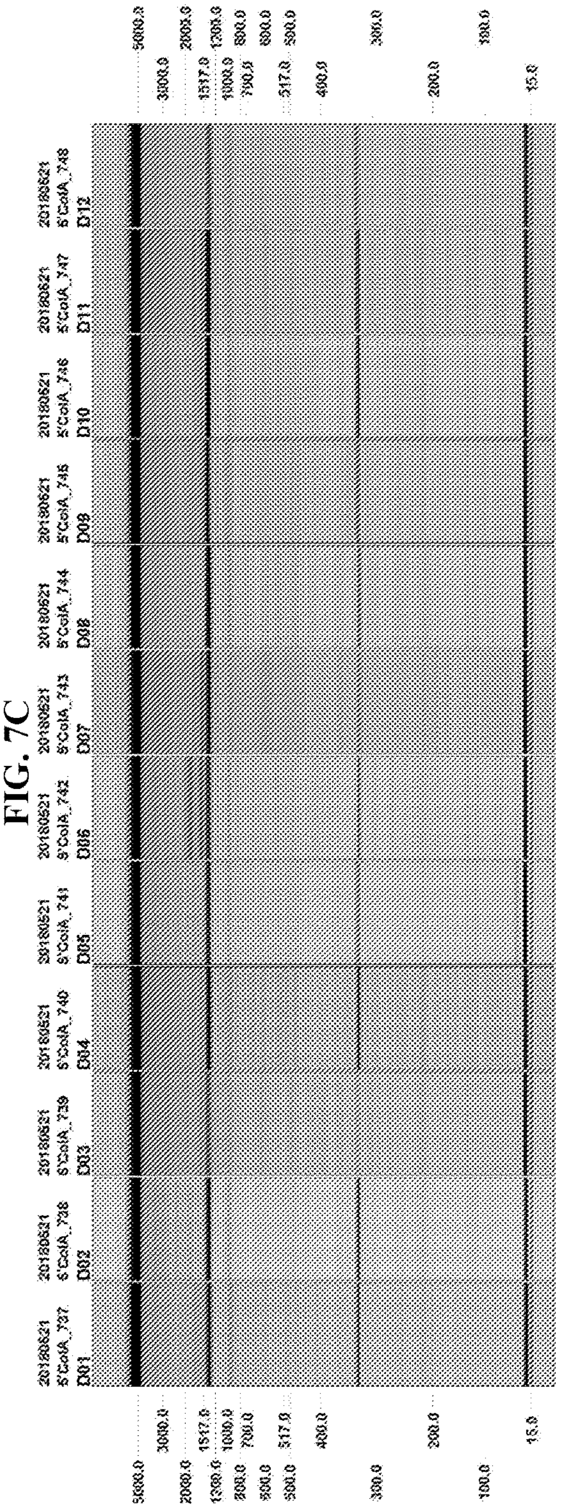
Figure 7E:
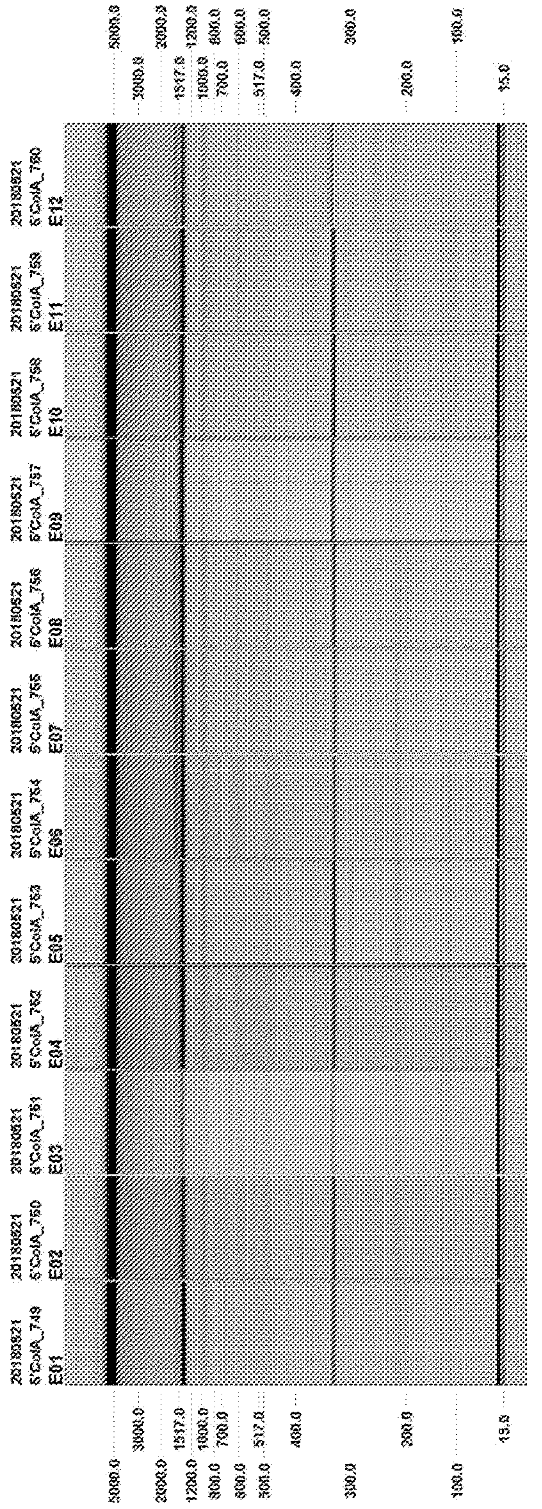
FIGS. 7E-7G are graphs displaying the PCR results for 5' ColA1 #749-773.
Figure 7F:
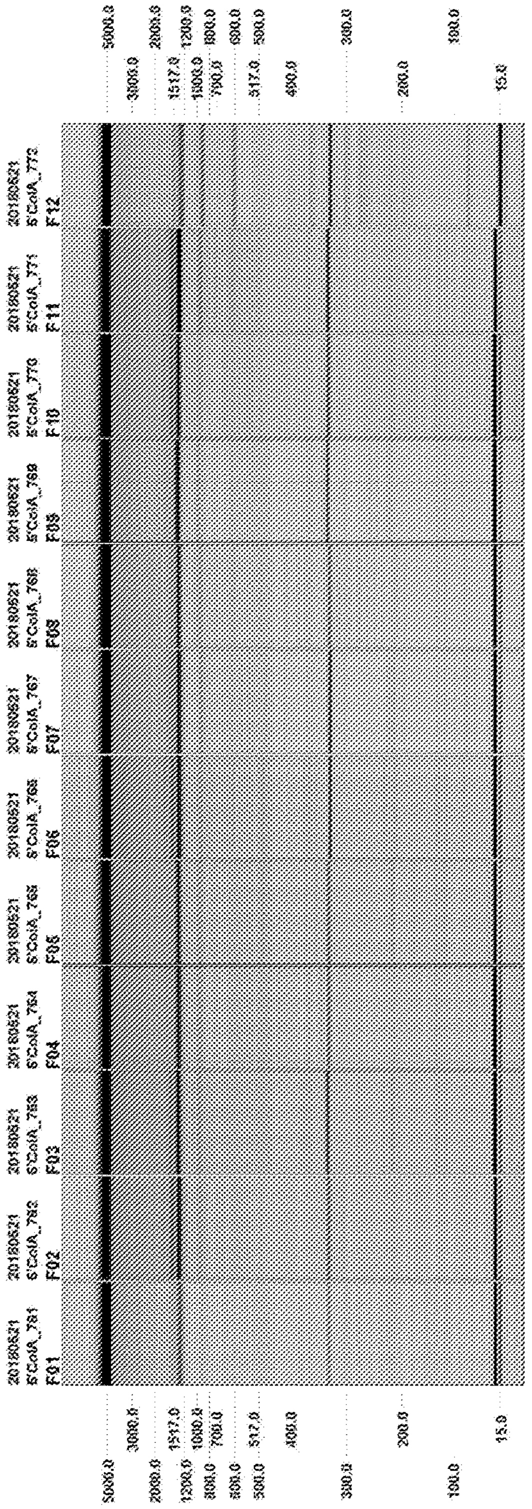
Figure 7G:
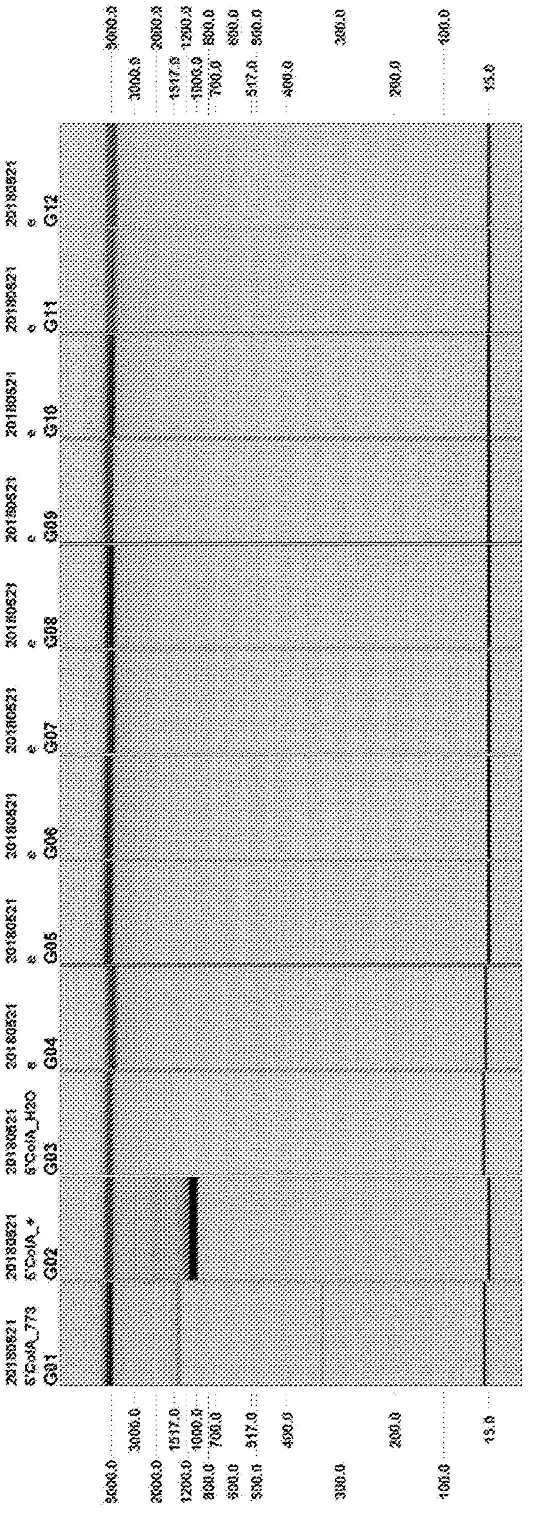
Figure 8A:
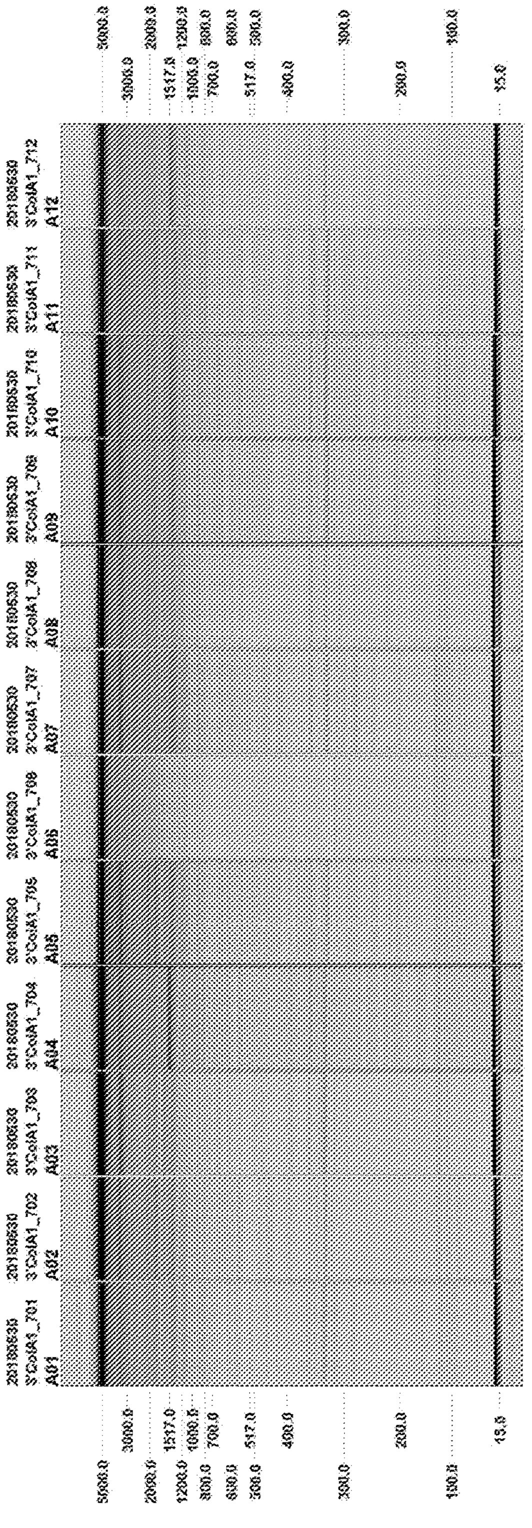
FIGS. 8A-8F are graphs displaying the PCR results for 3' ColA1 #701-773.
Figure 8B:
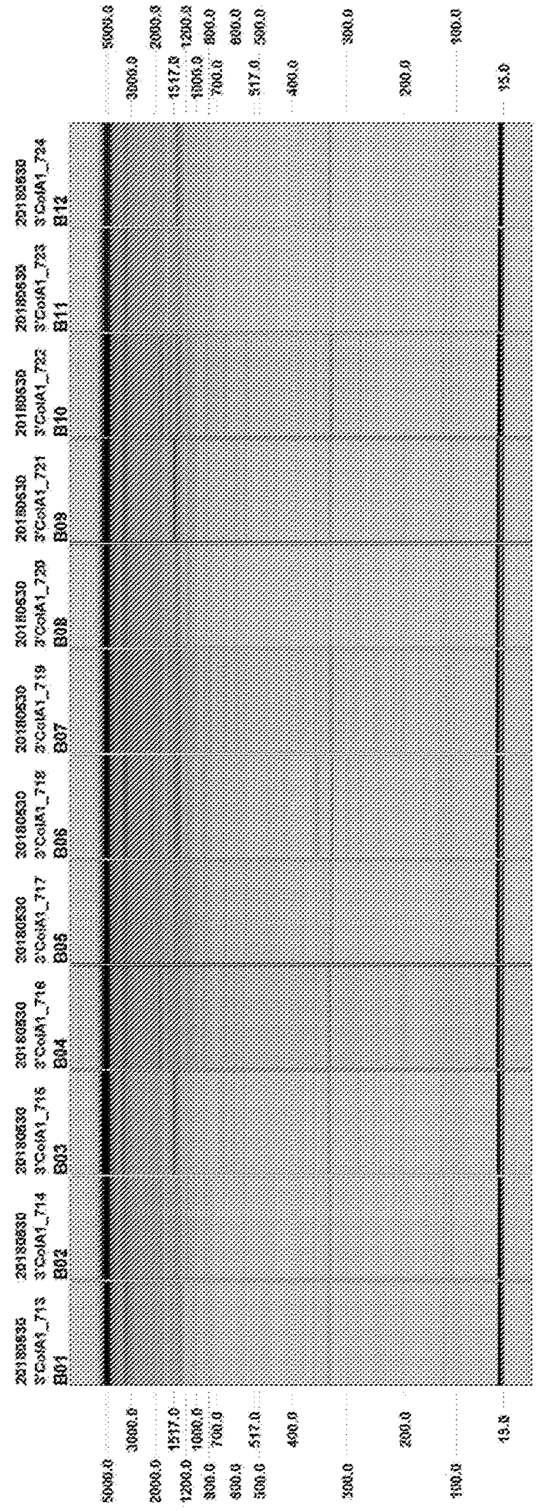
Figure 8C:
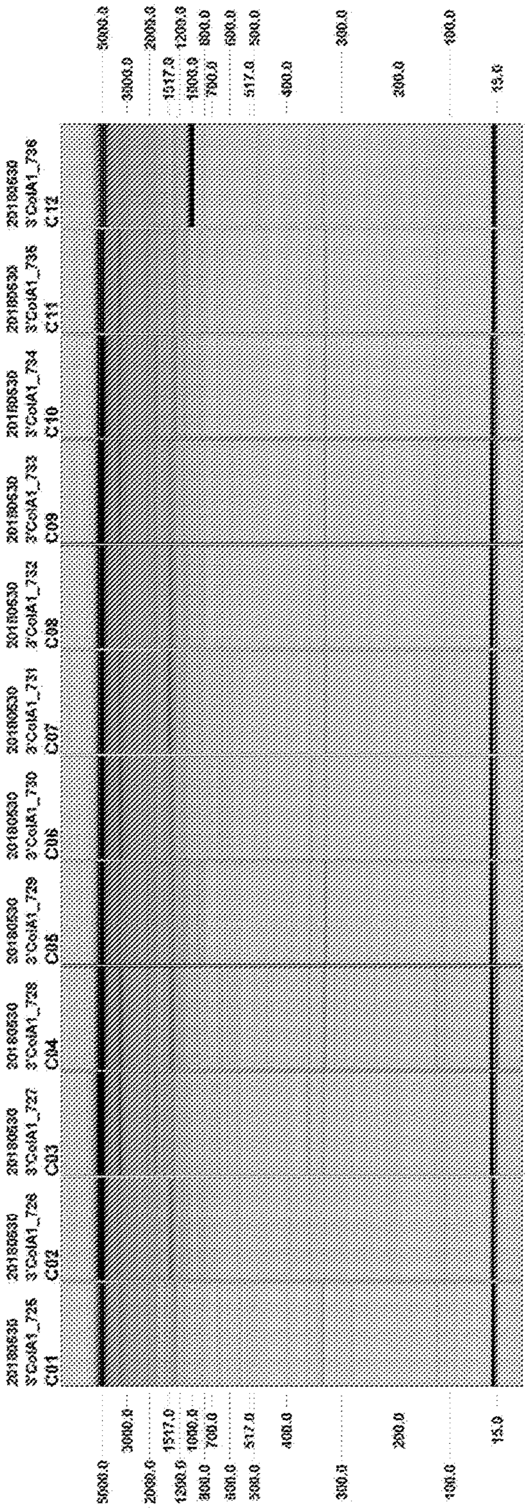
Figure 8D:
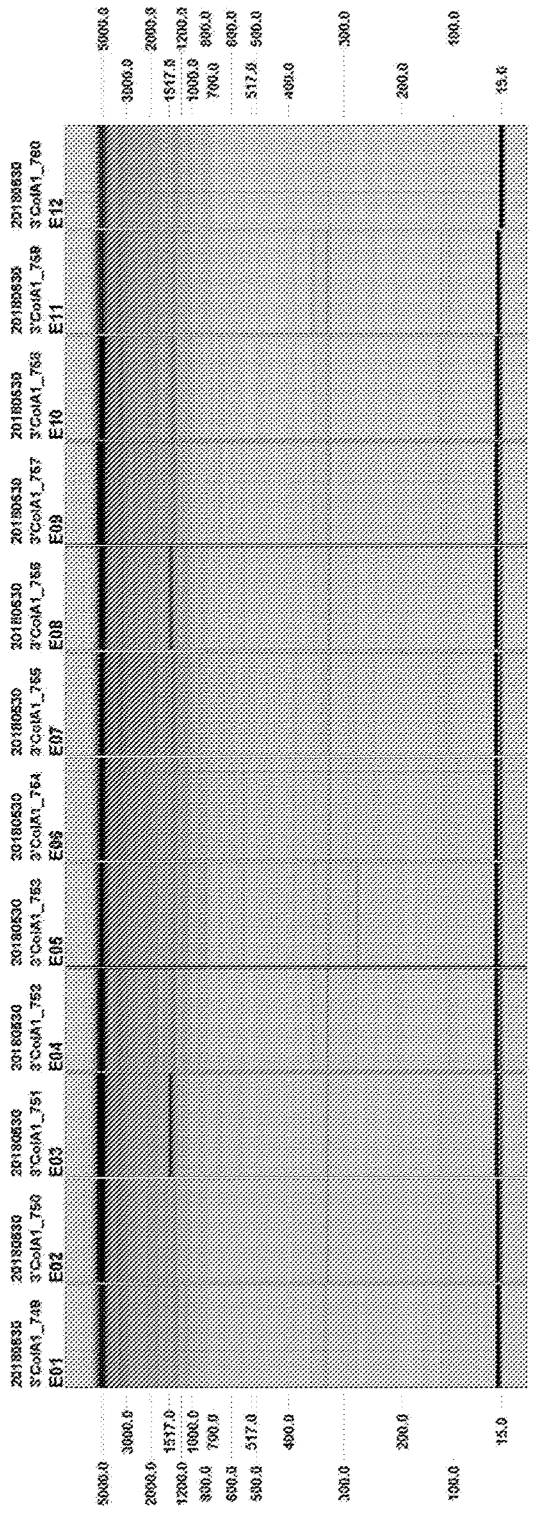
Figure 8E:
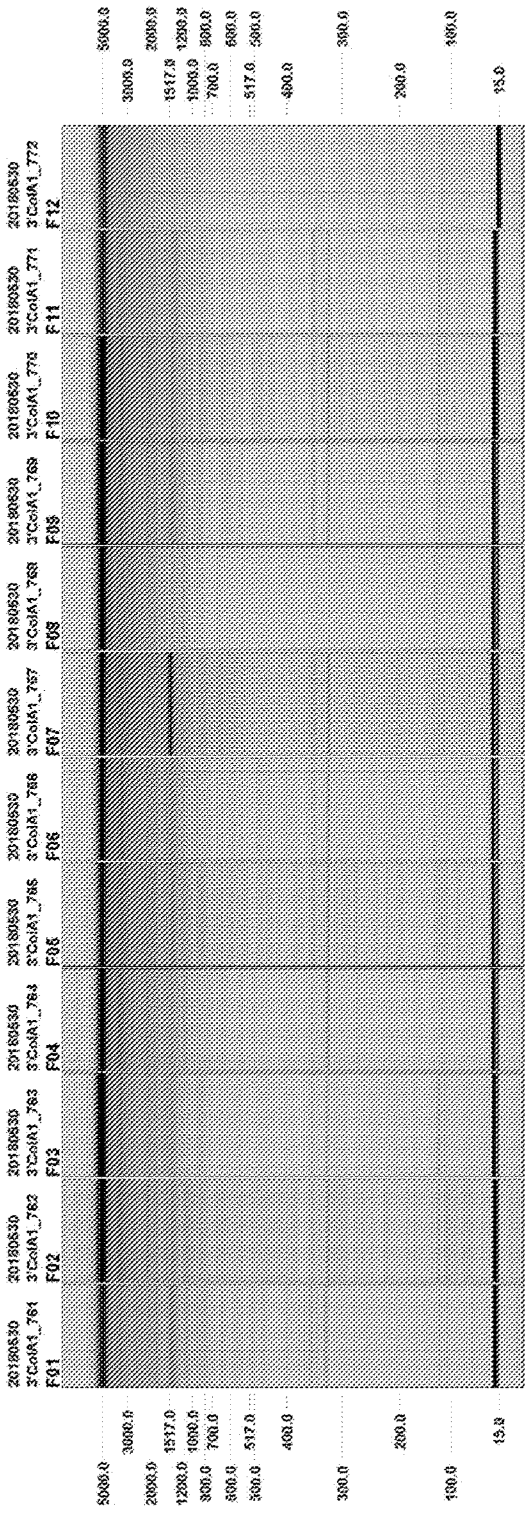
Figure 8F:
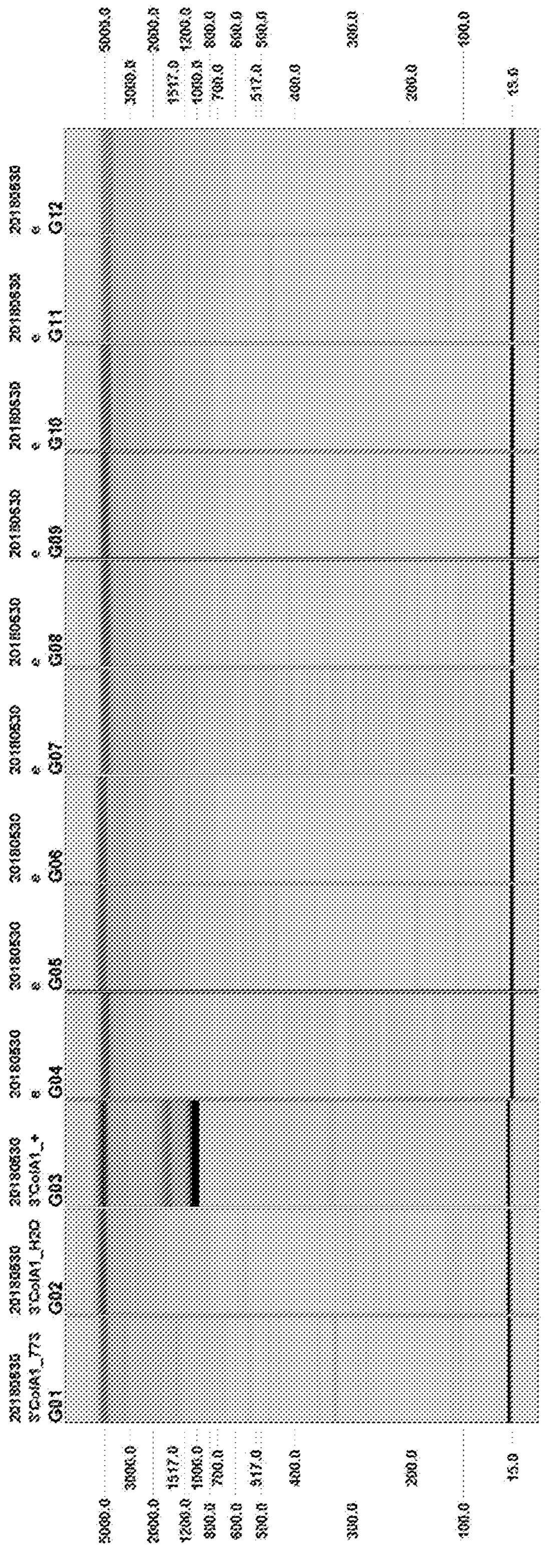

FIGS. 7A-7B displays the PCR results for 5' ColA1 #701-724. FIGS. 7C-7D displays the PCR results for 5' ColA1 #725-748. FIGS. 7E-7G displays the PCR results for 5' ColA1 #749-773.

FIGS. 8A-8F displays the PCR results for 3' ColA1 #701-773.

Off-target cleavage is a common concern with engineered nucleases"; however, several studies have suggested that off-target effects of the CRISPR/Cas system are much lower in animals than in cultured cells, partially because Cas9 and gRNAs are only short-lived RNAs in embryos"'. Despite the recent report of high off-target in vivo mutagenesis 42, many have rebuked such claims and criticize the high concentrations of CRISPR reagents used as the major culprit in this publication, forcing further editorial review over interpretation of the data. Nonetheless, to minimize propagation of founders with off-target cleavage, the present invention comprises whole genome sequencing of at least 2 founder rats from each strain to identify any potential off-target cleavage of Cas9. The present invention comprises propagating only rats without off-target events; however, if mutations arise in all founder animals, we will breed to segregate and remove the mutant allele from our strain.

Assess Efficiency of the UTS Targeting Platform

Figure 4:
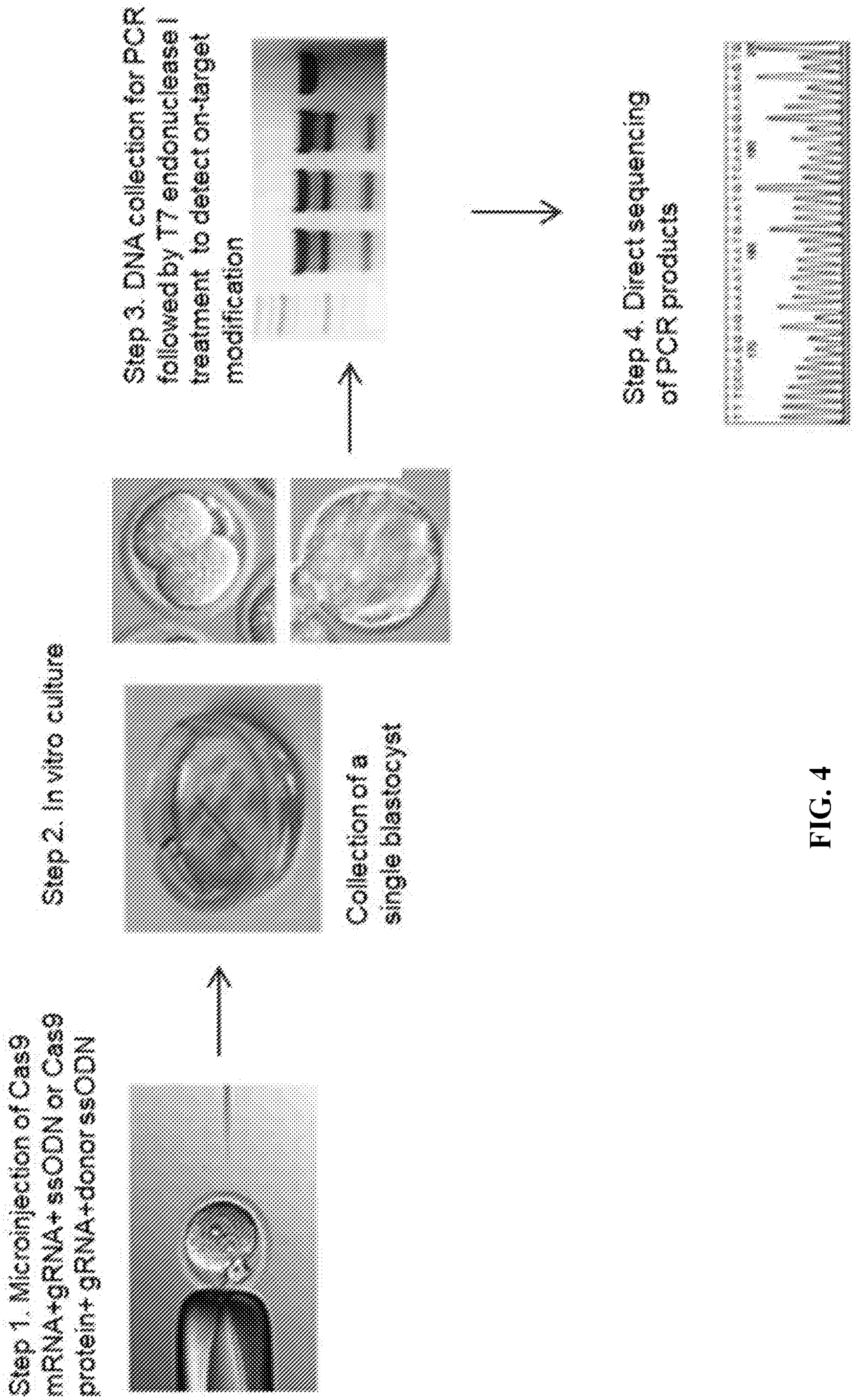
FIG. 4 is a diagram of an assessment of shRNA integration into the UTS, where one cell embryos will be harvested from TRE-GFP-UTS/CAG-rtTA3 crosses. Microinjection of CRISPR reagents+ssODN donor DNA will be performed. Embryos will be cultured for 4-5 days to the blastocyst stage and prepped for DNA for PCR amplification followed by T7 endonuclease I treatment. Positive clones will be further analyzed by direct DNA sequencing.

In the second embodiment, the present invention comprises rapidly modifying and inserting shRNA sequences into an UTS "homing cassette" platform. To do so, the present invention comprises breeding UTS and CAG-rtTA3 rats to obtain one-cell embryos from pregnant donor females. The present invention comprises performing both cytoplasmic and pronuclear injections of Cas9/gRNAs+shRNA ssODN donor cassettes using multiple experimental conditions and thereby establish optimal parameters to maximize the efficacy of CRISPR/Cas9-mediated HDR for our setting (FIG. 4). In one embodiment, the experimental conditions include, but are not limited to: Cas9 mRNA: −100 ng/u1; gRNA −50 ng/u1 (each if more than 1); ssODN or donor DNA (-50 ng/u1). Variations on the concentrations are the conditions to be varied. Although higher concentrations of Cas9 and donor DNA can increase HDR efficiency, it may led to higher viscosity of the injection mixture which requires larger microinjection tips. This may ultimately lead to rupture of the embryos or a decreased viability and/or inability to successfully transfer blastocysts to recipient females. Moreover, use of Cas9 protein pre-complexed with synthetic guides (which are commercially available) has also been reported to yield higher efficiencies than Cas9 mRNA generated by in vitro transcription, similar efficiencies using both methods have been seen in the laboratory. The present invention uses various conditions and reagents to define the optimal methods for systematic generation in the future. Following injection, the present invention comprises culturing embryos up to the blastocyst stage and harvesting them for screening via T7 endonuclease surveyor assay, DNA sequencing and GFP/shRNA induction following doxycycline treatment. Our efficiency rates for each condition will be carefully recorded to identify 'best practices' and establish a protocol suitable for cost-effectively scaling our methods. Given that our unique shRNA ssODNs will remain constant in size, the present invention standardizes the concentrations and Cas9 reagents used for all future production. Finally, by choosing the most effective microinjection conditions, the present invention optimizes the production timeline to establish a rapid platform for RNAi rat production and prove the commercial viability of such an approach to rapidly generate RNAi rats.

The second embodiment comprises: 1) generating RNAi rat embryos by insertion of shRNAs in the form of small single-stranded oligo deoxynucleotides (ssODN); 2) determining the most efficient method and concentrations for CRISPR/Cas9-mediated HDR; 3) establishing the best practices for scalability and rapid production.

The second embodiment assesses the feasibility and efficiency of ssODN insertion into the UTS within our "homing cassette". Although fully RNAi rats using these embryos are not generated, the efficiency of gene editing in embryos will accurately reflect the success rate of producing RNAi rats in the future. This practice of assessing gene editing in cultured embryos is our standard procedure when generating mice via CRISPR/Cas9— which allows the testing of multiple conditions and optimizes the strategies before the investing the time and costs of generating whole animals, and thus decreases the generation and screening of live animals as well as animal waste. By utilizing CRISPR editing in rats, testing numerous conditions and utilizing only a small donor template, the present invention establishes an optimized protocol for successful targeting.

RNAi Platform Validation Using Inducible shBrd4 Rats

The third embodiment comprises an RNAi system that induces potent and reversible gene expression in the rat model. To do this, the present invention crosses the inducible shBrd4 and CAG-rtTA3 strain to generate bitransgenic rats. These rats will be treated with doxycycline for 8 to 14 days and then removed from dox treatment and analyzed both phenotypically and histologically, examining the intestinal stem cell compartment, weight loss/gain, epithelium and myocardium as in previous studies[16,23,24]. The present invention comprises performing western blot analyses on select tissues to quantitate the knockdown levels. In addition, the present invention assesses: (1) GFP induction by whole tissue imaging and fluorescence microscopy on tissue sections at high magnification; (2) knockdown of Brd4 by immunofluorescence and compare with GFP expression (which should be inversely correlated); and (3) comparative phenotypic analyses between rat and mice, using histology of major organ systems, including the intestine, skin, pancreas, liver, spleen, kidney, heart, lungs, muscle and bone marrow. The third embodiment provides a proof-of-concept of RNAi rat models and justification to continue developing the platform for rapid production and commercialization.

The third embodiment comprises 1) Assessing the global GFP expression in all tissues; 2) Demonstrating the potent Brd4 knockdown in rats; 3) Assessing the toxicities in shBrd4 rats and comparing to other previous studies.

By utilizing the Col 1 al and Rosa26 loci for integration, the safe harbor loci working in mice will translate into safe harbors in the rat genome due to their chromosomal homology. In fact, two widely used loci in mice, Rosa26 and Hprt, have been used to generate transgenic rats and do show similar expression patterns as in mice[45,46]. Ultimately, the third embodiment demonstrates the integration of both the shRNA and CAG-rtTA3 at their respective loci and allows for potent and ubiquitous expression throughout the rat. If there is any difficulty in generating the CAG-rtTA3 strain, the third embodiment may use the Rosa26-rtTA2 strain46 for testing.

Future Directions

The present invention generates a rapid, flexible and scalable platform for systematic generation of inducible RNAi rat models with unique capabilities for temporal and reversible suppression of endogenous genes. This high-throughput system used to generate RNAi mice is also applicable to the rat system and, by extension, other mammalian models, including but not limited to Guinea pigs, rabbits, cats, dogs, nonhuman primates, pigs. The present invention will provide an alternative, more rapid and cost-effective approach to traditional gene deletion approaches and assist researchers in their quest to understand the function of specific genes in animal models. Inducible RNAi rat models will undoubtedly be powerful tools that can be used to model human disease, to mimic the action of putative drugs, and to assess the potential of therapeutic targeting strategies in vivo prior to the costly drug development. The present invention may examine the potential toxicities associated with systemic suppression of novel targets, such as STAG147, CMTM648, and FZD549 to help guide clinical treatment. In the day of modern medicine, many injuries from medication induced toxicities can be avoided if we can anticipate the potential harm (for example cytokine release syndrome caused by CAR-T therapy is now effectively managed with co-treatment of tocilizumab, an IL6R antagonise). The improvement in speed and cost at which inducible RNAi rats are produced and the insight they will provide will greatly increase the demand from both commercial and academic laboratories.

Illustrative Uses

A. Methods of Genetic Manipulation and Treatment

In certain aspects, the invention provides methods of creating specific genetic lesions and dampening gene expression in cells that may attenuate disease by way of CRISPR/Cas9-mediated gene engineering and shRNA expression, respectively. In accordance with the methods disclosed herein, the gRNAs, Cas9 and shRNAs may be reliably expressed in vivo in a variety of cell types. In certain embodiments the cells are administered in order to treat a condition. There are a variety of mechanisms by which genetic manipulation combined with shRNA expression in cells may be useful for treating a condition. For example, a condition may be caused in part by a population of cells expressing a combination of undesirable genes, some of which must genetically altered and some which may only be quelled to achieve therapeutic benefits. These cells may be ablated and replaced with administered cells comprising the correct genes and shRNAs to “fix” specific genes and/or decrease expression of other undesirable genes, respectively; alternatively, the diseased cells may be competed away by the administered cells, without need for ablation. As another example, a condition may be caused by a deficiency in a secreted factor. Amelioration of such a disorder may be achieved by administering cells expressing a shRNA that indirectly stimulates production of the secreted factor, e.g., by inhibiting expression of an inhibitor.

CRISPR/Cas9 may be used to alter the genetic makeup on nearly any gene, just as an shRNA may be targeted to essentially any gene, and in some instances, this combination will required to achieve the gene expression profile which may be helpful in treating a condition. For example, in the case of cancer therapeutics, monotherapy is usually ineffective and combination therapy has become the mainstay of effective treatment to provide the best prognosis. The target genes may participate in a disease process in the subject. The target genes may encode a host protein that is co-opted by a virus during viral infection, such as a cell surface receptor to which a virus binds while infecting a cell. HIV binds to several cell surface receptors, including CD4 and CXCR5. The introduction of HSCs or other T cell precursors carrying specific genetic manipulations and a shRNA directed to an HIV receptor or coreceptor is expected to create a pool of resistant T cells, thereby ameliorating the severity of the HIV infection. Similar principles apply to other viral infections.

Immune rejection is mediated by recognition of foreign Major Histocompatibility Complexes. Where heterologous cells are to be administered to a subject, the cells may be genetically altered and transfected with shRNAs that target any MHC components that are likely to be recognized by the host immune system.

In many embodiments, the shRNA transfected cells will achieve beneficial results by partially or wholly replacing a population of diseased cells in the subject. The transfected cells may autologous cells derived from cells of the subject, but carrying a shRNA that confers beneficial effects.

B. A Method for Disease Induction and Treatment in Animals

One utility of the present invention is to generate animal models that have both the potential to initiate a disease process and also carry an shRNA or shRNAs that may be used to treat the disease itself. By incorporating the construct depicted in FIG. 1-? in embryonic stem cells (ESCs), ESC-derived animals can be generated by way of blastocyst injection. At any time point, CRISPR/Cas9-mediated mutagenesis may by induced by treating the animals with doxycycline. Mutagenesis may even be triggered in embryos by treating pregnant mothers with doxycycline as well. These induced mutations by be disease sensitizing and trigger a cascade of events that lead to disease pathogenesis. At different time points during disease development, inversion of the inserted cassette can be induced by treatment with CRE/tamoxifen. Subsequently, following the inversion event, treatment with doxycycline can induce shRNA expression and thus silencing of specific genes that may have therapeutic potential to treat the disease or attenuate the disease process.

The system provides a unique ability to induce multiple genetic manipulations at a specific time point without having to cross the mice to other disease-allele carrying strains. It is distinctive in that shRNAs that suppress gene function may also be used following the onset of disease progression to determine whether the target gene(s) have therapeutic potential or perhaps accelerate disease.

C. Screening Assays

One utility of the present invention is as a method inducing a specific phenotype via CRISPR/Cas9 and identifying gene function in the specific phenotype context of an organism, especially higher eukaryotes, by comprising the use of double-stranded RNA to inhibit the activity of a target gene of previously unknown function. Instead of the time consuming and laborious isolation of mutants by traditional genetic screening, functional genomics would envision determining the function of uncharacterized genes by employing the invention to reduce the amount and/or alter the timing of target gene activity. The invention could be used in determining potential targets for pharmaceuticals, understanding normal and pathological events associated with development, determining signaling pathways responsible for postnatal development/aging, and the like. The increasing speed of acquiring nucleotide sequence information from genomic and expressed gene sources, including total sequences for mammalian genomes, can be coupled with the invention to determine gene function in a cell or in a whole organism. The preference of different organisms to use particular codons, searching sequence databases for related gene products, correlating the linkage map of genetic traits with the physical map from which the nucleotide sequences are derived, and artificial intelligence methods may be used to define putative open reading frames from the nucleotide sequences acquired in such sequencing projects.

A simple assay would be to inhibit gene expression according to the partial sequence available from an expressed sequence tag (EST). Functional alterations in growth, development, metabolism, disease resistance, or other biological processes would be indicative of the normal role of the EST's gene product.

The ease with which the phenotype can be generated and then the dsRNA construct can be activated in the same intact cell/organism containing the target gene allows the present invention to be used in high throughput screening (HTS). For example, duplex RNA can be produced by an amplification reaction using primers flanking the inserts of any gene library derived from the target cell or organism. Inserts may be derived from genomic DNA or mRNA (e.g., cDNA and cRNA). Individual clones from the library can be replicated and then isolated in separate reactions, but preferably the library is maintained in individual reaction vessels (e.g., a 96 well microtiter plate) to minimize the number of steps required to practice the invention and to allow automation of the process.

In an exemplary embodiment, the subject invention provides an arrayed library of RNAi constructs. The array may be in the form of solutions, such as multi-well plates, or may be "printed" on solid substrates upon which cells can be grown. To illustrate, solutions containing duplex RNAs that are capable of inhibiting the different expressed genes can be placed into individual wells positioned on a microtiter plate as an ordered array, and intact cells/organisms in each well can be assayed for any changes or modifications in behavior or development due to inhibition of target gene activity.

In certain aspects, the invention provides methods for evaluating gene function in vivo. A cell containing an shRNA expression construct designed to decrease expression of a target gene may be introduced into an animal and a phenotype may be assessed to determine the effect of the decreased gene expression. An entire animal may be generated from cells (e.g., ES cells) containing an shRNA expression construct designed to decrease expression of a target gene. A phenotype of the transgenic animal may be assessed.

The animal may be essentially any experimentally tractable animal, such as a non-human primate, a rodent (e.g., a mouse), a lagomorph (e.g., a rabbit), a canid (e.g. a domestic dog), a feline (e.g., a domestic cat). In general, animals with complete or near complete genome projects are preferred.

A phenotype to be assessed may be essentially anything of interest. Quantitating the tendency of a stem cell to contribute to a particular tissue or tumor is a powerful method for identifying target genes that participate in stem cell differentiation and in tumorigenic and tumor maintenance processes. Phenotypes that have relevance to a disease state may be observed, such as susceptibility to a viral, bacterial or other infection, insulin production or glucose homeostasis, muscle function, neural regeneration, production of one or more metabolites, behavior patterns, inflammation, production of autoantibodies, obesity, etc.

A panel of shRNAs that affect target gene expression by varying degrees may be used, and phenotypes may be assessed. In particular, it may be useful to measure any correlation between the degree of gene expression decrease and a particular phenotype.

A heterogeneous pool of shRNA constructs may be introduced into cells, and these cells may be introduced into an animal. In an embodiment of this type of experiment, the cells will be subjected to a selective pressure and then it will be possible to identify which shRNAs confer resistance or sensitivity to the selective pressure. The selective pressure may be quite subtle or unintentional, for example, mere engraftment of transfected HSCs may be a selective pressure, with some shRNAs interfering with engraftment and others promoting engraftment. Development and differentiation may be viewed as a "selective pressure", with some shRNAs modulating the tendency of certain stem cells to differentiate into different subsets of progeny. Treatment with a chemotherapeutic agent may be used as selective pressure, as described below. The heterogeneous pool of shRNAs may be obtained from a library, and in certain preferred embodiments, the library is a barcoded library, permitting rapid identification of shRNA species.

In certain aspects, the invention provides methods for identifying genes that affect the sensitivity of tumor cells to a chemotherapeutic agent. The molecular mechanisms that underlie chemoresistance in human cancers remain largely unknown. While various anticancer agents clearly have different mechanisms of action, most ultimately either interfere with DNA synthesis or produce DNA damage. This, in turn, triggers cellular checkpoints that either arrest cell proliferation to allow repair or provoke permanent exit from the cell cycle by apoptosis or senescence.

In certain embodiments, a method comprises introducing into a subject a transfected stem cell comprising a nucleic acid construct encoding an shRNA, wherein the shRNA is complementary to at least a portion of a target gene, wherein the transfected stem cell exhibits decreased expression of the target gene, and wherein the transfected stem cell gives rise to a transfected tumor cell in vivo. For example, the stem cell may be derived from an animal that has a genetic predisposition to tumorigenesis, such as an oncogene overexpressing animal (e.g. Eμ-myc mice) or a tumor suppressor knockout (e.g., p53 −/− animal). Alternatively, an animal comprising the stem cells may be exposed to carcinogenic conditions such that tumors comprising cells derived from the stem cells are generated. An animal having tumors may be treated with a chemotherapeutic or other anti-tumor regimen, and the effect of this regimen on cells expressing the shRNA may be evaluated. An shRNA that is overrepresented following anti-tumor therapy is likely to be targeted against a gene that confers sensitivity. An shRNA that is underrepresented following anti-tumor therapy is likely to be targeted against a gene that confers resistance. An shRNA that is underrepresented may be developed for use as a co-therapeutic to be co-administered with the chemotherapeutic agent in question and suppress resistance.

Overrepresentation and underrepresentation are generally comparative terms, and determination of these parameters will generally involve comparison to a control or benchmark. A comparison may simply be to the same animal prior to chemotherapy administration. A comparison may also be to a control subject that has not received the chemotherapeutic agent. A comparison may be to an average of multiple other shRNA trials. Any control need not be contemporaneous with the experiment, although the protocol should be substantially the same.

This technique may be performed on individual shRNAs (see e.g., BIM shRNA, in the Examples below). The technique may also be adopted for highly parallel screening. For example, a method may comprise introducing into a subject a plurality of transfected stem cells, wherein each transfected stem cell comprises a nucleic acid construct comprising a representative shRNA of an shRNA library, and wherein a representative shRNA of an shRNA library is complementary to at least a portion of a representative target gene, wherein a plurality of the transfected stem cells exhibits decreased expression of a representative target gene, and wherein a plurality of the transfected stem cells gives rise to transfected tumor cells in vivo. Notably, it is not necessary or expected that every shRNA is different or that every transfected cell will become part of a tumor. Once tumors have been generated, a chemotherapeutic or other anti-tumor regimen may be administered, and the overrepresentation or underrepresentation of shRNA species may be evaluated. In certain preferred embodiments, each representative shRNA is associated with a distinguishable tag that permits rapid identification of each shRNA. For example, shRNAs may be obtained from a shRNA library that is barcoded.

Certain methods described herein take advantage of the fact that large numbers of cancer cells (e.g., lymphoma cells) can be isolated from affected mice and transplanted into syngeneic, immunocompetent recipients to create a lymphoma that is virtually indistinguishable from the spontaneous disease. This allows in vitro manipulation of tumor cells to create potentially chemoresistant variants that can be analyzed in vivo. In certain exemplary embodiments, the invention exploits advantages of the Eμ-myc system to undertake an unbiased search for genetic alterations that can confer resistance to chemotherapeutics, such as the widely used alkylating agent, CTX.

The following is an outline of an example of a screen to identify genes that confer resistance to CTX using an unbiased, genetic approach. An overview of the screen is diagrammed in FIG. 19. Populations of isolated lymphoma cells from the Eμ-myc mouse receive pools of sequence verified shRNAs that specifically target murine genes. Engineered cells are introduced into immunocompetent, syngeneic recipient animals. Upon the appearance of tumors, the animals are be treated with CTX. In each case, the time of remission is measured, and, upon relapse, the animals undergo a second round of treatment. After two rounds of therapy, the shRNA resident in resistant populations are identified and transferred into fresh populations of lymphoma cells, which are transplanted into naïve animals. After the appropriate number of selection cycles, individual shRNAs that are capable of conferring drug resistance are obtained.

D. Cell Delivery Systems

In certain embodiments, the invention provides a composition formulated for administration to a patient, such as a human or veterinary patient. A composition so formulated may comprise a stem cell comprising the Cas9 protein and gRNAs to induce specific genetic alterations and a nucleic acid construct encoding an shRNA designed to decrease the expression of a target gene. A composition may also comprise a pharmaceutically acceptable excipient. Essentially any suitable cell may be used, included cells selected from among those disclosed herein. Transfected cells may also be used in the manufacture of a medicament for the treatment of subjects. Examples of pharmaceutically acceptable excipients include matrices, scaffolds or other substrates to which cells may attach (optionally formed as solid or hollow beads, tubes, or membranes), as well as reagents that are useful in facilitating administration (e.g. buffers and salts), preserving the cells (e.g. chelators such as sorbates, EDTA, EGTA, or quaternary amines or other antibiotics), or promoting engraftment.

Cells may be encapsulated in a membrane or in a microcapsule. Cells may be placed in microcapsules composed of alginate or polyacrylates. Aebischer et al. U.S. Pat. No. 4,892,538; Aebischer et al. U.S. Pat. Nos. 5,106,627; 4,391,909; 4,353,888.

The site of implantation of insulin-producing cell compositions may be selected by one of skill in the art depending on the type of cell and the therapeutic objective. Exemplary implantation sites include intravenous or intraarterial administration, administration to the liver (via portal vein injection), the peritoneal cavity, the kidney capsule or the bone marrow.

Other illustrative uses may be found in U.S. Pat. No. 8,697,359, herein incorporated by reference, including for plant genomics and other therapeutic methodologies.

All publications and patents mentioned herein are hereby incorporated by reference in their entirety as if each individual publication or patent was specifically and individually indicated to be incorporated by reference. In case of conflict, the present application, including any definitions herein, will control.

Literature Cited

1 DiMasi, J. A., Grabowski, H. G. & Hansen, R. W. Innovation in the pharmaceutical industry: New estimates of R&D costs. J Health Econ 47, 20-33, doi:10.1016/j.jhealeco.2016.01.012 (2016).
2 Harrison, R. K. Phase II and phase III failures: 2013-2015. Nat Rev Drug Discov 15, 817-818, doi:10.1038/nrd.2016.184 (2016).
3 Abbott, A. Return of the rat. Nature 460, 788, doi:10.1038/460788a (2009).
4 Aitman, T. J. et al. Progress and prospects in rat genetics: a community view. Nat Genet 40, 516-522, doi:10.1038/ng.147 (2008).

5 Gill, T. J., 3rd, Smith, G. J., Wissler, R. W. & Kunz, H. W. The rat as an experimental animal. Science 245, 269-276 (1989).
6 Huang, G., Ashton, C., Kumbhani, D. S. & Ying, Q. L. Genetic manipulations in the rat: progress and prospects. Curr Opin Nephroi Hypertens 20, 391-399, doi:10.1097/MNH.0b013e328347768a (2011).
7 Jacob, H. J., Lazar, J., Dwinell, M. R., Moreno, C. & Geurts, A. M. Gene targeting in the rat: advances and opportunities. Trends Genet 26, 510-518, doi:10.1016/j.tig.2010.08.006 (2010).
8 Dickins, R. A. et al. Tissue-specific and reversible RNA interference in transgenic mice. Nat Genet 39, 914-921, doi:ng2045 [pii] 10.1038/ng2045 (2007).
9 Beard, C., Hochedlinger, K., Plath, K., Wutz, A. & Jaenisch, R. Efficient method to generate single-copy transgenic mice by site-specific integration in embryonic stem cells. Genesis 44, 23-28, doi:10.1002/gene.20180 (2006).
10 Premsrirut, P. K. et al. A rapid and scalable system for studying gene function in mice using conditional RNA interference. Cell 145, 145-158, doi:10.1016/j.cell.2011.03.012 (2011).
11 Dow, L. E. et al. A pipeline for the generation of shRNA transgenic mice. Nat Protoc 7, 374-393, doi:10.1038/nprot.2011.446nprot.2011.446 [pii] (2012).
12 Ebbesen, S. H. et al. Pten loss promotes MAPK pathway dependency in HER2/neu breast carcinomas. Proc Natl Acad Sci USA 113, 3030-3035, doi:10.1073/pnas.1523693113
13 Brondfield, S. et al. Direct and indirect targeting of MYC to treat acute myeloid leukemia. Cancer Chemother Pharmacol 76, 35-46, doi:10.1007/s00280-015-2766-z (2015).
14 Huang, C. H. et al. CDK9-mediated transcription elongation is required for MYC addiction in hepatocellular carcinoma. Genes Dev 28, 1800-1814, doi:10.1101/gad.244368.114 (2014).
15 McJunkin, K. et al. Reversible suppression of an essential gene in adult mice using transgenic RNA interference. Proc Natl Acad Sci USA 108, 7113-7118, doi:10.1073/pnas.1104097108 (2011).
16 Bolden, J. E. et al. Inducible in vivo silencing of Brd4 identifies potential toxicities of sustained BET protein inhibition. Cell Rep 8, 1919-1929, doi:10.1016/j.celrep.2014.08.025 (2014).
17 Zaiss, A. K. et al. Reversible suppression of cyclooxygenase 2 (COX-2) expression in vivo by inducible RNA interference. PLoS One 9, e101263, doi:10.1371/journal-.pone.0101263 (2014).
18 Lin, C. J. et al. Targeting synthetic lethal interactions between myc and the eIF4F complex impedes tumorigenesis. Cell Reports (2012).
19 Lee, T., Paquet, M., Larsson, 0. & Pelletier, J. Tumor cell survival dependence on the DHX9 DExH-box helicase. Oncogene 35, 5093-5105, doi:10.1038/onc.2016.52 (2016).
20 Mullenders, J. et al. Cohesin loss alters adult hematopoietic stem cell homeostasis, leading to myeloproliferative neoplasms. J Exp Med 212, 1833-1850, doi:10.1084/jem.20151323 (2015).
21 Sakamaki, J. I. et al. Bromodomain Protein BRD4 Is a Transcriptional Repressor of Autophagy and Lysosomal Function. Mol Cell 66, 517-532 e519, doi: 10.1016/j.molcel.2017.04.027 (2017).
22 Strikoudis, A., Lazaris, C., Ntziachristos, P., Tsirigos, A. & Aifantis, I. Opposing functions of H2BK120 ubiquitylation and H3K79 methylation in the regulation of pluripotency by the Pafl complex. Cell Cycle, 0, doi: 10.1080/15384101.2017.1295194 (2017).
23 Nakagawa, A. et al. Selective and reversible suppression of intestinal stem cell differentiation by pharmacological inhibition of BET bromodomains. Sci Rep 6, 20390, doi:10.1038/srep20390 (2016).
24 Sun, Y., Huang, J. & Song, K. BET protein inhibition mitigates acute myocardial infarction damage in rats via the TLR4/TRAF6/NF-kappaB pathway. Exp Ther Med 10, 2319-2324, doi:10.3892/etm.2015.2789 (2015).
25 Wang, B. et al. BET Bromodomain Blockade Mitigates Intimal Hyperplasia in Rat Carotid Arteries. EBioMedicine 2, 1650-1661, doi:10.1016/j.ebiom.2015.09.045 (2015).
26 Pelossof, R. et al. Prediction of potent shRNAs with a sequential classification algorithm. Nat Biotechnol 35, 350-353, doi:10.1038/nbt.3807 (2017).
27 Fellmann, C. et al. Functional identification of optimized RNAi triggers using a massively parallel sensor assay. Mol Cell 41, 733-746, doi:10.1016/j.molcel.2011.02.008 (2011).
28 Fellmann, C. et al. An optimized microRNA backbone for effective single-copy RNAi. Cell Rep 5, 1704-1713, doi: 10.1016/j.celrep.2013.11.020 (2013).
29 Watanabe, C., Cuellar, T. L. & Haley, B. Quantitative evaluation of first, second, and third generation hairpin systems reveals the limit of mammalian vector-based RNAi. RNA Biol 13, 25-33, doi:10.1080/15476286.2015.1128062 (2016).
30 van der Meer, R., Song, H. Y., Park, S. H., Abdulkadir, S. A. & Roh, M. RNAi screen identifies a synthetic lethal interaction between PIM1 overexpression and PLK1 inhibition. Clin Cancer Res 20, 3211-3221, doi:10.1158/1078-0432.CCR-13-3116 (2014).
31 Singleton, K. R. et al. Kinome RNAi Screens Reveal Synergistic Targeting of MTOR and FGFR1 Pathways for Treatment of Lung Cancer and HNSCC. Cancer Res 75, 4398-4406, doi:10.1158/0008-5472.CAN-15-0509 (2015).
32 Luo, M. L., Mullis, A. S., Leenay, R. T. & Beisel, C. L. Repurposing endogenous type I CRISPR-Cas systems for programmable gene repression. Nucleic Acids Res 43, 674-681, doi:10.1093/nar/gku971 gku971 [pii] (2015).
33 Qi, L. S. et al. Repurposing CRISPR as an RNA-guided platform for sequence-specific control of gene expression. Cell 152, 1173-1183, doi:10.1016/j.cell.2013.02.022 (2013).
34 Cheng, A. W. et al. Multiplexed activation of endogenous genes by CRISPR-on, an RNA-guided transcriptional activator system. Cell Res 23, 1163-1171, doi:10.1038/cr.2013.122 (2013).
35 Gilbert, L. A. et al. CRISPR-mediated modular RNA-guided regulation of transcription in eukaryotes. Cell 154, 442-451, doi:10.1016/j.cell.2013.06.044 (2013).
36 Andrieu, G., Belkina, A. C. & Denis, G. V. Clinical trials for BET inhibitors run ahead of the science. Drug Discov Today Technol 19, 45-50, doi:10.1016/j.ddtec.2016.06.004 (2016).
37 Boi, M. et al. The BET Bromodomain Inhibitor OTX015 Affects Pathogenetic Pathways in Preclinical B-cell Tumor Models and Synergizes with Targeted Drugs. Clin Cancer Res 21, 1628-1638, doi:10.1158/1078-0432.CCR-14-1561 (2015).
38 Henssen, A. et al. Targeting MYCN-Driven Transcription By BET-Bromodomain Inhibition. Clin Cancer Res 22, 2470-2481, doi:10.1158/1078-0432.CCR-15-1449 (2016).

39 Li, D. et al. Heritable gene targeting in the mouse and rat using a CRISPR-Cas system. Nat Biotechnol 31, 681-683, doi:10.1038/nbt.2661 (2013).
40 Wang, H. et al. One-step generation of mice carrying mutations in multiple genes by CRISPR/Cas-mediated genome engineering. Cell 153, 910-918, doi:10.1016/j.ce11.2013.04.025 (2013).
41 Yang, H. et al. One-step generation of mice carrying reporter and conditional alleles by CRISPR/Cas-mediated genome engineering. Cell 154, 1370-1379, doi: 10.1016/j.ce11.2013 0.08.022 (2013).
42 Schaefer, K. A. et al. Unexpected mutations after CRISPR-Cas9 editing in vivo. Nat Methods 14, 547-548, doi:10.1038/nmeth.4293 (2017).
43 Hsu, P. D. et al. DNA targeting specificity of RNA-guided Cas9 nucleases. Nat Biotechnol 31, 827-832, doi: 10.1038/nbt.2647 (2013).
44 Pattanayak, V. et al. High-throughput profiling of off-target DNA cleavage reveals RNA-programmed Cas9 nuclease specificity. Nat Biotechnol 31, 839-843, doi: 10.1038/nbt.2673 (2013).
45 Remy, S. et al. Efficient gene targeting by homology-directed repair in rat zygotes using TALE nucleases. Genome Res 24, 1371-1383, doi:10.1101/gr.171538.113 (2014).
46 Sheng, Y. et al. Generation and characterization of a Tet-On (rtTA-M2) transgenic rat. BMC Dev Blot 10, 17, doi:10.1186/1471-213X-10-17 (2010).
47 van der Lelij, P. et al. Synthetic lethality between the cohesin subunits STAG1 and STAG2 in diverse cancer contexts. Elife 6, doi:10.7554/eLife.26980 (2017).
48 Burr, M. L. et al. CMTM6 maintains the expression of PD-Ll and regulates anti-tumour immunity. Nature, doi: 10.1038/nature23643 (2017).
49 Steinhart, Z. et al. Genome-wide CRISPR screens reveal a Wnt-FZDS signaling circuit as a druggable vulnerability of RNF43-mutant pancreatic tumors. Nat Med 23, 60-68, doi:10.1038/nm.4219 (2017).
50 Maude, S. L., Barrett, D., Teachey, D. T. & Grupp, S. A. Managing cytokine release syndrome associated with novel T cell-engaging therapies. Cancer J 20, 119-122, doi:10.1097/PP0.0000000000000035 (2014).

What is claimed is:

1. A method of using founder knock-in strains comprising:

a. creating a founder strain with a nucleotide sequence comprising a promoter and a miRNA backbone by i. using a CRISPR/Cas9 system to insert a nucleotide sequence comprising promoter sequence operably linked to a miRNA backbone sequence and a reporter sequence downstream of the Col1a1 gene on chromosome 10 of rat embryo and producing a founder strain rat whose genome comprises said promoter sequence operably linked to a miRNA backbone sequence and a reporter sequence downstream of the Col1a1 gene on chromosome 10; and ii. obtaining an embryo or a cell that is produced using the founder strain rat in step (i) and transducing the embryo or cell with a CRISPR/Cas9 system that comprises a Cas9 protein, a gRNA that is targeted to the miRNA backbone sequence, and a donor template that includes a shRNA sequence, thereby inserting said shRNA sequence into said miRNA backbone sequence of the embryo or cell and producing a subsequent founder knock-in strain rat or cell wherein the miRNA backbone sequence comprises the integrated shRNA sequence; and b. using the founder strain to knockin a variable shRNA sequence for a subsequent strain to be produced.

2. The method of claim 1, wherein creating the founder strain comprises using a genome editing system to insert common sequences used for each subsequent RNAi strain; and wherein using the founder strain to knockin a variable shRNA sequence comprises generating the subsequent strain harboring a shRNA targeting an endogenous gene; and generating each strain by transduction of reagents into embryos or cells.

3. The method of claim 2, wherein the nucleotide sequence further comprises a reporter sequence.

4. The method of claim 3, wherein the gene editing system is selected from the group consisting of a CRISPR/Cas9 system, zinc finger nucleases (ZFNs), and transcription activator-like effector nucleases (TALENs).

5. The method of claim 4, wherein the CRISPR/Cas9 system includes a Cas9 protein, a gRNA, and a donor template.

6. The method of claim 4, wherein the promoter driving expression of the miRNA-based shRNA is selected from the group consisting of: a tet-inducible, the PolIII human or murine U6 and H1 systems, the cytomegalovirus (CMV) promoter/enhancer, the human β-actin promoter, the glucocorticoid-inducible promoter present in the rat and mouse mammary tumor virus long terminal repeat (MMTV LTR), the long terminal repeat sequences of Moloney murine leukemia virus (MuLV LTR), the SV40 early or late region promoter, the promoter contained in the 3' long terminal repeat of Rous sarcoma virus (RSV), the herpes simplex virus (HSV) thymidine kinase promoter/enhancer, the herpes simplex virus LAT promoter, polyoma virus, fowlpox virus, adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, an immunoglobulin promoter, and from heat-shock promoters, provided such promoters are compatible with the host cell systems, and inducible systems, including Tet promoters.

7. The method of claim 6, wherein the embryos or cells are from the rat species.

* * * * *

UNITED STATES PATENT AND TRADEMARK OFFICE

CERTIFICATE OF CORRECTION

PATENT NO. : 11,957,114 B2
APPLICATION NO. : 16/955521
DATED : April 16, 2024
INVENTOR(S) : Prem Premsrirut It is certified that error appears in the above-identified patent and that said Letters Patent is hereby corrected as shown below:

In the Specification

Column 1, Line 13:
Please insert the following section before the SEQUENCE LISTING section:
--GOVERNMENT LICENSE RIGHTS
This invention was made with government support under OD026184 awarded by National Institutes of Health (NIH). The government has certain rights in the invention.--

Signed and Sealed this
Twenty-seventh Day of August, 2024

Katherine Kelly Vidal

Katherine Kelly Vidal
*Director of the United States Patent and Trademark Office*